United States Patent
Zakelj et al.

(10) Patent No.: US 11,166,707 B2
(45) Date of Patent: Nov. 9, 2021

(54) RETRACTOR WITH MODULAR TAP ASSEMBLIES

(71) Applicant: Life Spine, Inc., Huntley, IL (US)

(72) Inventors: Paul Christopher Zakelj, Chicago, IL (US); Daniel Predick, West Lafayette, IN (US); Michael S. Butler, St. Charles, IL (US)

(73) Assignee: LIFE SPINE, INC., Huntley, IL (US)

( * ) Notice: Subject to any disclaimer, the term of this patent is extended or adjusted under 35 U.S.C. 154(b) by 282 days.

(21) Appl. No.: 16/366,259

(22) Filed: Mar. 27, 2019

(65) Prior Publication Data

US 2019/0216453 A1 Jul. 18, 2019

Related U.S. Application Data

(63) Continuation-in-part of application No. 15/448,010, filed on Mar. 2, 2017, now Pat. No. 10,245,015, which is a continuation-in-part of application No. 15/207,026, filed on Jul. 11, 2016, now Pat. No. 10,149,671, which is a continuation-in-part of application No. 14/874,073, filed on Oct. 2, 2015, now Pat. No. 10,178,987, which is a
(Continued)

(51) Int. Cl.
*A61B 17/02* (2006.01)
*A61B 17/70* (2006.01)
*A61F 2/46* (2006.01)
*A61B 1/32* (2006.01)

(52) U.S. Cl.
CPC ........ *A61B 17/0206* (2013.01); *A61B 17/025* (2013.01); *A61B 17/7077* (2013.01); *A61B 17/7082* (2013.01); *A61B 1/32* (2013.01); *A61B 2017/0256* (2013.01); *A61F 2/4611* (2013.01)

(58) Field of Classification Search
CPC ..... A61B 17/0206; A61B 17/025; A61B 1/32; A61B 2017/0256
See application file for complete search history.

(56) References Cited

U.S. PATENT DOCUMENTS 530,728 A   12/1894 Sherbrook
3,509,873 A   5/1970 Karlin
(Continued)

FOREIGN PATENT DOCUMENTS

WO  WO-2015/134367 A1   9/2015
WO  WO-2015/160343 A1   10/2015

*Primary Examiner* — Samuel S Hanna
(74) *Attorney, Agent, or Firm* — Foley & Lardner LLP

(57) ABSTRACT

A retractor assembly includes a base, a first side assembly, a second side assembly, and a medial arm assembly. The first side assembly is coupled to a first side of the base and translates relative to the base along a first direction. The second side assembly is coupled to a second side of the base and configured to translate relative to the base along the first direction. The medial arm assembly is coupled to the base and can extend in an extension direction and retract in a retraction direction. The extension direction is opposite the retraction direction. The extension direction and the retraction direction are perpendicular to the first direction. The medial arm assembly includes a body, and a blade assembly. The blade assembly includes a receiving portion and a medial blade. The receiving portion and the medial blade are rotatably interfaced via a ball and a socket.

20 Claims, 41 Drawing Sheets

Related U.S. Application Data continuation-in-part of application No. 13/720,800, filed on Dec. 19, 2012, now Pat. No. 9,386,916.

(60) Provisional application No. 61/577,857, filed on Dec. 20, 2011.

(56) References Cited

U.S. PATENT DOCUMENTS

| | | |
|---|---|---|
| 4,065,941 A | 1/1978 | Aoki |
| 7,335,207 B1 | 2/2008 | Smith |
| 2004/0049101 A1 | 3/2004 | Phillips et al. |
| 2005/0137461 A1* | 6/2005 | Marchek ............ A61B 17/025 600/220 |
| 2005/0215866 A1 | 9/2005 | Kim |
| 2007/0049930 A1 | 3/2007 | Hearn et al. |
| 2007/0203399 A1 | 8/2007 | Gephart et al. |
| 2007/0238932 A1 | 10/2007 | Jones et al. |
| 2010/0154604 A1 | 6/2010 | Su |
| 2010/0222644 A1 | 9/2010 | Sebastian et al. |
| 2011/0130793 A1* | 6/2011 | Woolley ............ A61B 17/7077 606/279 |
| 2011/0301423 A1 | 12/2011 | Koros et al. |
| 2014/0024900 A1 | 1/2014 | Capote et al. |
| 2015/0230787 A1 | 8/2015 | Friedrich et al. |
| 2015/0250467 A1 | 9/2015 | Higgins |
| 2015/0305731 A1 | 10/2015 | Friedrich et al. |
| 2015/0313585 A1* | 11/2015 | Abidin ............ A61B 17/0206 600/213 |

\* cited by examiner

RETRACTOR WITH MODULAR TAP ASSEMBLIES

CROSS-REFERENCE TO RELATED PATENT APPLICATIONS

This application is a continuation-in-part of application Ser. No. 15/448,010, filed Mar. 2, 2017, which is a continuation-in-part of application Ser. No. 15/207,026, filed Jul. 11, 2016, which is a continuation in part of application Ser. No. 14/874,073, filed Oct. 2, 2015, which is a continuation-in-part of application Ser. No. 13/720,800, filed Dec. 19, 2012, now U.S. Pat. No. 9,386,916, which claims the benefit of Provisional Application No. 61/577,857 filed Dec. 20, 2011. The entire contents of all of these applications are incorporated herein by reference.

BACKGROUND

The present invention relates to surgical devices for retracting anatomy to provide exposure of an operating site, and more particularly, to retraction apparatus providing improved access to a surgical site for a spine procedure.

Surgical procedures typically require the use of a retractor to hold anatomies and/or tissues out of the way from the incision down to the actual surgical site. In the case of posterior spinal surgery for implanting various spine fixation components and/or other spinal orthopedic devices, it is necessary to retract different tissue types including large and strong paraspinal muscles in order to get to the actual surgical site. In order to accomplish this goal, spinal retractors have been developed that hold back the desired anatomy of a spinal surgical site and is fixed relative to the patient either directly or indirectly.

Many different types of spinal retractors are currently available many of which use retractor blades—a part of the distraction mechanism of the spinal retractor that enters the site of the incision and physically holds the anatomy apart. The retractor blades can be attached to a frame at an angle such as about 90 degrees from horizontal (i.e. generally vertical) or as to have a variable angle. However, current spinal retractors have various deficiencies. For instance, fixed angle retractor blade configurations limit flexibility of the spinal retractor, including loss of surgical site precision and overall stabilization. The variable angle retractor blade configurations lack preciseness and flexibility in retractor blade positioning.

It is therefore evident from the above that there is a need for an improved spinal retractor that can overcome the deficiencies of current spinal retractors. It is also evident from the above that there is a need for an improved spinal retractor which provides enhanced preciseness and flexibility in retractor blade positioning. It is furthermore evident that there is a need for an improved spinal retractor as aforementioned which also allows for instrument and/or component retention and positioning by the retractor blade assembly.

SUMMARY

The present disclosure relates to a retractor assembly, according to an exemplary embodiment. The retractor assembly includes a base, a first side assembly, a second side assembly, and a medial arm assembly. The first side assembly is coupled to a first side of the base and is configured to translate relative to the base along a first direction. The second side assembly is coupled to a second side of the base and is configured to translate relative to the base along the first direction. The medial arm assembly is coupled to the base and is configured to extend in an extension direction and retract in a retraction direction. The extension direction is opposite the retraction direction. The extension direction and the retraction direction are perpendicular to the first direction. The medial arm assembly includes a body and a blade assembly. The blade assembly includes a receiving portion and a medial blade. The receiving portion and the medial blade are configured to rotatably interface via a ball and a socket.

The medial arm assembly includes a frame configured to translate relative to the body, according to an exemplary embodiment. The blade assembly is coupled to the frame.

The blade assembly is configured to rotatably interface with the frame via a hinge and pivot about a first axis extending through a center of the hinge, according to an exemplary embodiment.

The medial blade is configured to rotatably interface with the receiving portion about a rotational axis extending outwards from a center of the receiving portion, according to an exemplary embodiment.

The medial blade includes the ball and the receiving portion includes the socket, according to an exemplary embodiment. The socket is configured to receive the ball.

The receiving portion includes a locking member configured to selectably engage the ball to restrict rotation of the blade about the rotational axis, according to an exemplary embodiment.

The locking member includes a set screw, according to an exemplary embodiment. The set screw is configured to threadingly interface with an aperture of the receiving portion, engage a pin, and drive the pin into engagement with a corresponding surface of the ball. The pin has a surface at one end configured to interface with an end of the set screw and a surface at a second end configured to interface with the corresponding surface of the ball.

The body includes a locking mechanism configured to selectably transition between a locked mode and an unlocked mode, according to an exemplary embodiment. The locked mode restricts translation of the frame relative to the body. The unlocked mode allows translation of the frame relative to the body.

The body includes a releasable ratcheting mechanism, according to an exemplary embodiment. The releasable ratcheting mechanism is configured to restrict translation of the frame in at least one of the extension direction and the retraction direction.

Another implementation of the present disclosure relates to a retractor assembly, according to an exemplary embodiment. The retractor assembly includes a base, a first side assembly, a second side assembly, and a medial arm assembly. The medial arm assembly is coupled to the base and includes a medial arm body, a frame, and a medial blade assembly. The frame is configured to translate relative to the medial arm body through an aperture of the medial arm body. The medial blade assembly includes a receiving member, a medial blade, and a body. The receiving member is configured to hingedly interface at an end of the frame. The body is configured to rotatably interface with the receiving member. The medial blade includes a first member configured to slidably interface with a channel of the body, and a second member configured to selectably deflect relative to the first member to enable repositioning of the blade along the channel.

The second member includes one or more tabs configured to interface with one or more notches of the body and at least a portion of the first member is configured to slidably interface within the channel of the body, according to an exemplary embodiment.

The notches are disposed along an exterior surface of the body and define predefined positions of the medial blade with respect to the body, according to an exemplary embodiment.

The second member is configured to selectably deflect between an engaged state and a disengaged state, according to an exemplary embodiment. The engaged state locks the medial blade at a current position relative to the body. The disengaged state allows translation of the medial blade relative to the body. In the engaged state, at least one of the one or more tabs is engaged with at least one of the notches. In the disengaged state the one or more tabs are disengaged from the notches.

The one or more tabs are disposed at an end of the second member, according to an exemplary embodiment. The first member and the second member are disposed a distance apart to define a space therebetween for receiving an adjustment member to transition the second member between the engaged state and the disengaged state.

The blade assembly is configured to receive the adjustment member, according to an exemplary embodiment. The second member is configured to deflect to transition between the engaged state and the disengaged state in response to a rotation of the adjustment member.

The medial blade is configured to releasably interface with a modular tap assembly including a driver, a hoop, a sleeve, and a tap, according to an exemplary embodiment.

Another implementation of the present disclosure relates to a method of operating a retractor, according to an exemplary embodiment. The method includes inserting a blade adjustment member into an opening defined between a first engagement member and a second engagement member of a medial blade of the retractor. The method further includes rotating the blade adjustment member in a first direction to an adjustment position to cause the second engagement member to deflect relative to the first engagement member. The method further includes translating the medial blade to a desired location by translating the blade adjustment member while the blade adjustment member is in the adjustment position.

The method further includes rotating the blade adjustment member in a first direction, according to an exemplary embodiment. Rotating the blade adjustment member in the first direction includes rotating the blade adjustment member a predetermined angular amount, according to an exemplary embodiment.

The method further includes rotating the blade adjustment member in a second direction the predetermined angular amount, according to an exemplary embodiment. The second direction is opposite the first direction.

Rotating the blade adjustment member in the first direction so that the second protrusion of the blade adjustment member causes the second engagement member to deflect causes one or more protrusions of the elongated member to disengage a set of notches, according to an exemplary embodiment.

Further aspects of the present disclosure will become apparent from consideration of the drawings and the following description of various embodiments. A person skilled in the art will realize that other embodiments are possible and that the details can be modified in a number of respects without departing from the inventive concepts disclosed herein. The following drawings and description are to be regarded as illustrative in nature and not restrictive.

BRIEF DESCRIPTION OF THE DRAWINGS

The features of the present disclosure will be better understood by reference to the accompanying drawings which illustrate various embodiments, wherein.

Like reference numbers indicate the same or similar parts throughout the several figures.

Figure 1:
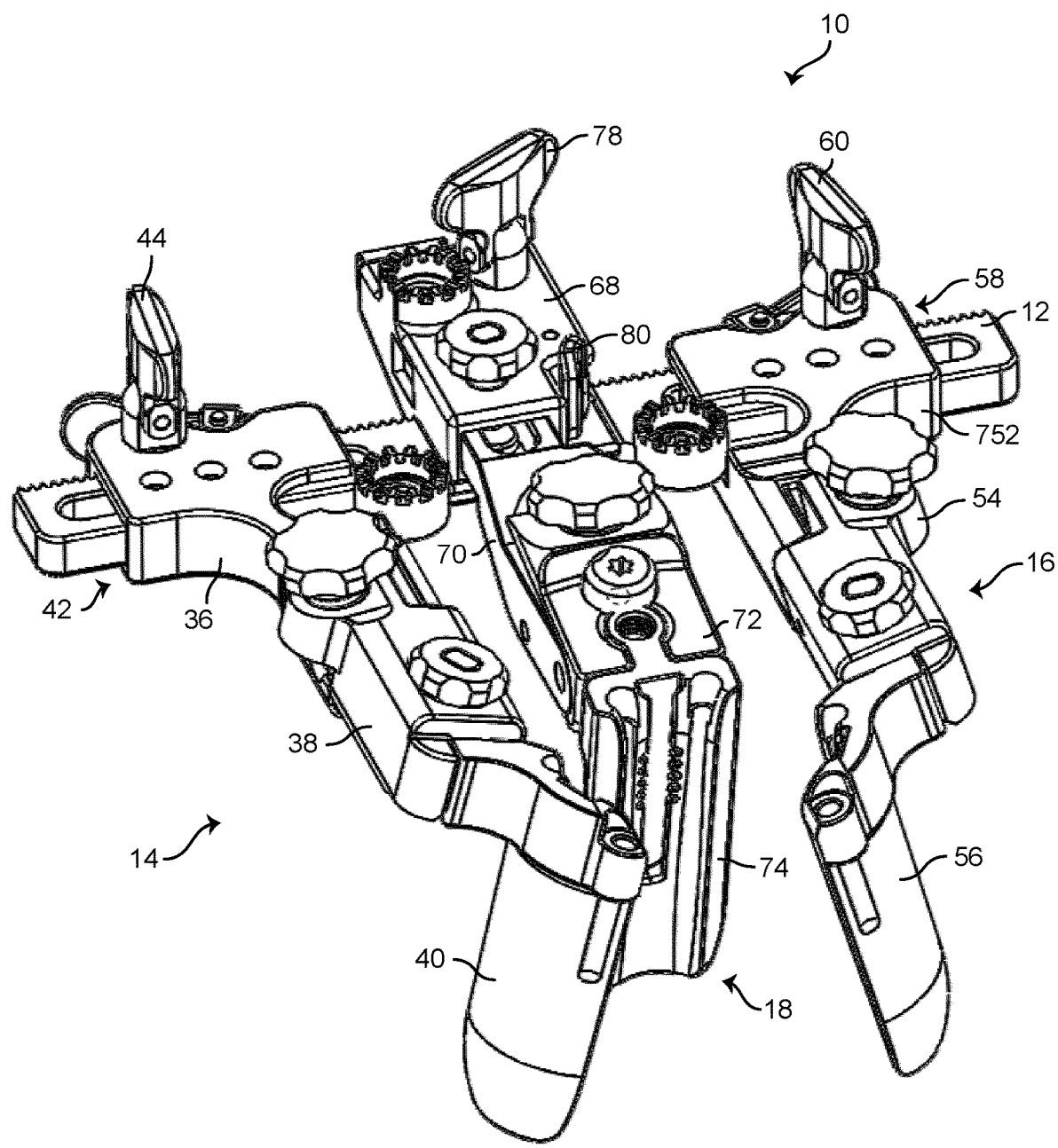
FIG. 1 is a perspective view of a spinal retractor.

A description of the features, functions and/or configurations of the components depicted in the various figures will now be presented. It should be appreciated that not all of the features of the components of the figures are necessarily described. Some of these non-discussed features as well as discussed features are inherent from the figures. Other non-discussed features may be inherent in component geometry and/or configuration.

DETAILED DESCRIPTION

Referring generally to the FIGURES, a spinal retractor is shown. The spinal retractor can include a medial arm configured to extend or retract. The medial arm can include a releasable ratcheting mechanism configured to allow translation of the medial arm in a first direction and restrict translation of the medial arm in a second, opposite, direction. The ratcheting mechanism can be released such that the medial arm can be translated in either direction (e.g., extended or retracted). The medial arm may also include a locking mechanism configured to lock the translation of the medial arm at a current location. The medial arm also includes a ball and socket interface configured to facilitate rotation of a medial blade of the medial arm about a first axis, and a hinge configured to facilitate hinged rotation of the medial blade of the medial arm about a second axis. The socket interface can be locked at a current angular position about the first axis by tightening a set screw. The set screw is configured to engage a pin. The pin can be driven by the set screw to engage a ball of the ball and socket interface to prevent rotation of the medial blade about the first axis. The medial blade of the medial arm can be extended or retracted. A blade extension adjuster can be inserted into an opening of the medial blade and turned ninety degrees to transition the medial blade from a locked configuration to an extension configuration. The medial blade is configured to translate along a track or channel of a body member of the medial arm. The medial blade may be configured to interface with one or more notches along at least part of the length of the channel. The blade extension adjuster can be used to transition the medial blade into a disengaged or extension configuration such that the medial blade does not engage the notches and can be extended or retracted. Once a desired location of the medial blade along the channel is achieved, the blade extension adjuster can be rotated back ninety degrees to transition the medial blade into the locked configuration. A modular tap assembly can be coupled to the medial blade. Advantageously, the medial arm facilitates extension and retraction of the medial blade and/or the modular tap assembly along a first axis, rotation about a first axis and a second axis, and extension or retraction of the medial blade and/or the modular tap assembly in a second direction.

Referring to FIGS. 1-22, a spinal retractor 10 is shown according to another alternative embodiment. The spinal retractor 10 shown in FIGS. 1-22 shares many of the features of the spinal retractors shown in FIGS. 1-5, 6-21, and 22-32 of U.S. application Ser. No. 15/448,010, filed Mar. 2, 2017, the entirety of which is incorporated by reference herein, and all such features are understood to be part of the embodiment shown in FIGS. 1-22.

Referring to FIGS. 1-6, the spinal retractor 10 includes a frame or base 12, a first side assembly 14, a second side assembly 16, and a center assembly 18. The first side assembly 14, the second side assembly 16, and the center assembly 18 are coupled to the frame 12 to enable translating movement of the assemblies 14, 16, and 18 (or portions thereof) relative to the frame 12 to provide retraction of tissue, etc. during surgical procedures involving the spine, etc. The first side assembly 14 and the second side assembly 16 translate relative to the frame 12 in a medial-lateral direction (e.g., along a first axis or direction), and the center assembly 18 translates relative to the frame 12 in a cephalad-caudal direction (e.g., along a second axis or direction) in a generally perpendicular fashion relative to the first and second side assemblies. In one embodiment, each of the assemblies 14, 16, 18 may be adjusted (e.g., translated) relative to the frame 12 independently (e.g., such that each of the first side assembly 14, the second side assembly 16, and the center assembly 18 may be adjusted individually).

Figure 14:
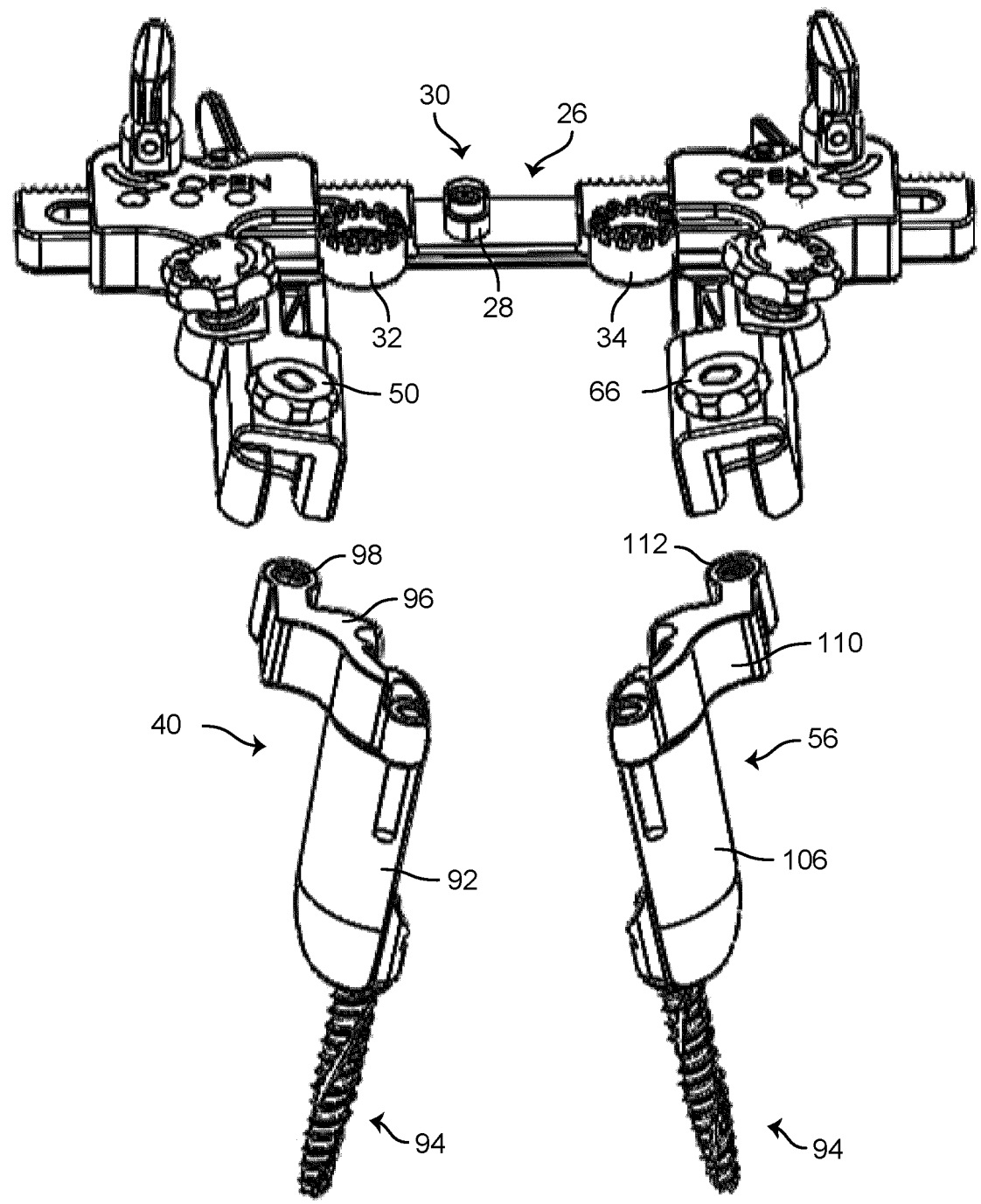
FIG. 14 is a perspective view of first and second blade assemblies decoupled from a spinal retractor according to one embodiment.

The frame 12 is in one embodiment a generally elongated member (e.g., a rail, etc.) including a first side slot 20 and a second side slot 22 extending along the longitudinal direction of the frame 12. Frame teeth 24 extend along all or a part of the frame 12 and facilitate adjustment of the first and second side assemblies 14, 16 along the frame 12. As shown in FIG. 14, in one embodiment, the frame 12 includes a frame recess 26 defining an area of reduced thickness for the frame 12. The frame recess 26 is configured to receive the center assembly 18. In one embodiment, a central boss 28 extends up from a portion of the frame 12 in the area of the frame recess 26, and may include a boss aperture 30 configured to receive a threaded member of the center assembly 18 to secure the center assembly 18 relative to the frame 12. Mounting members 32, 34 extend from the frame 12 and enable securement of retractor 10 via one or more table mount assemblies, etc. The mounting members 32, 34 may be at least partially received in correspondingly shaped recesses in the first and second side assemblies 14, 16 when the retractor 10 is in a closed position as shown in FIG. 3.

According to one embodiment, the first side assembly 14 includes a first arm portion 36 and a second arm portion 38. The first arm portion 36 translates along the frame 12, and the second arm portion 38 rotates, or pivots, relative to the first arm portion 36 to provide angulation for a first side blade assembly 40. The first arm portion 36 includes a first side cavity 42 that receives the frame 12, and a first side adjustment knob 44 that engages the frame teeth 24 to move the first arm portion 36, and therefore the first side assembly 14, along the frame 12. The first side adjustment knob 44 is rotatable in opposite directions and engages the frame teeth 24 to provide more or less retraction at a desired site. A first side ratchet mechanism 46 (see FIG. 2) is biased into engagement with the frame teeth 24 to prevent inward movement of the first arm portion 36, and therefore the first side assembly 14, relative to the frame 12 when a user releases the first side adjustment knob 44. The first side ratchet mechanism 46 includes a depressible tab portion that enables a user to release the first side ratchet mechanism 46 and permit free movement of the first side assembly 14 along the frame 12.

Figure 17:
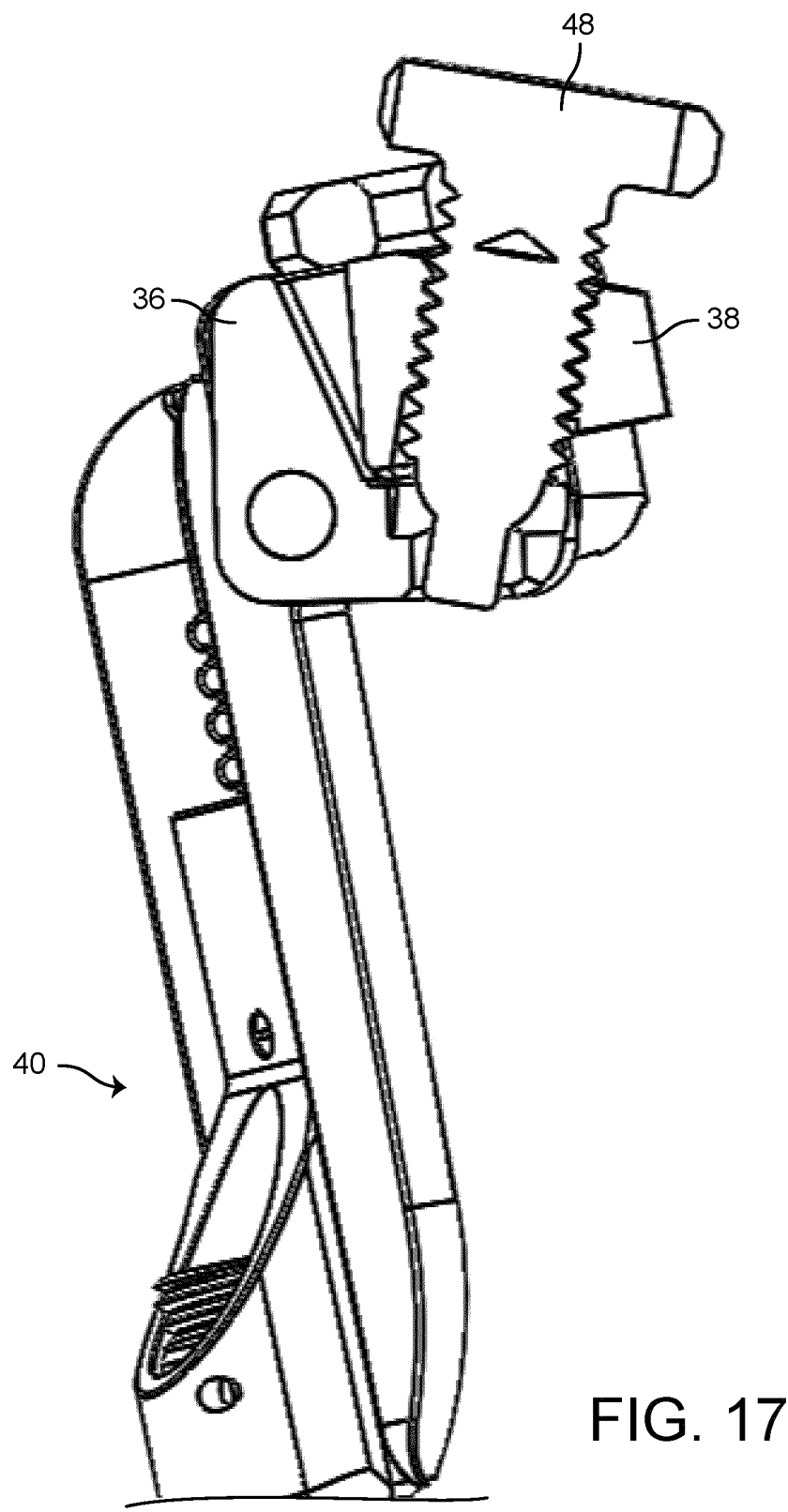

In some embodiments, a first side angulation knob 48 enables pivotal adjustment of the second arm portion 38 relative to the first arm portion 36 between a normal position (see FIG. 5) and an angulated position (see FIG. 1). As also shown in FIG. 17, rotation of the first side angulation knob 48 cause the second arm portion 38 to pivot relative to the first arm portion 36, providing a desired degree of angulation to a particular retraction site.

Figure 3:
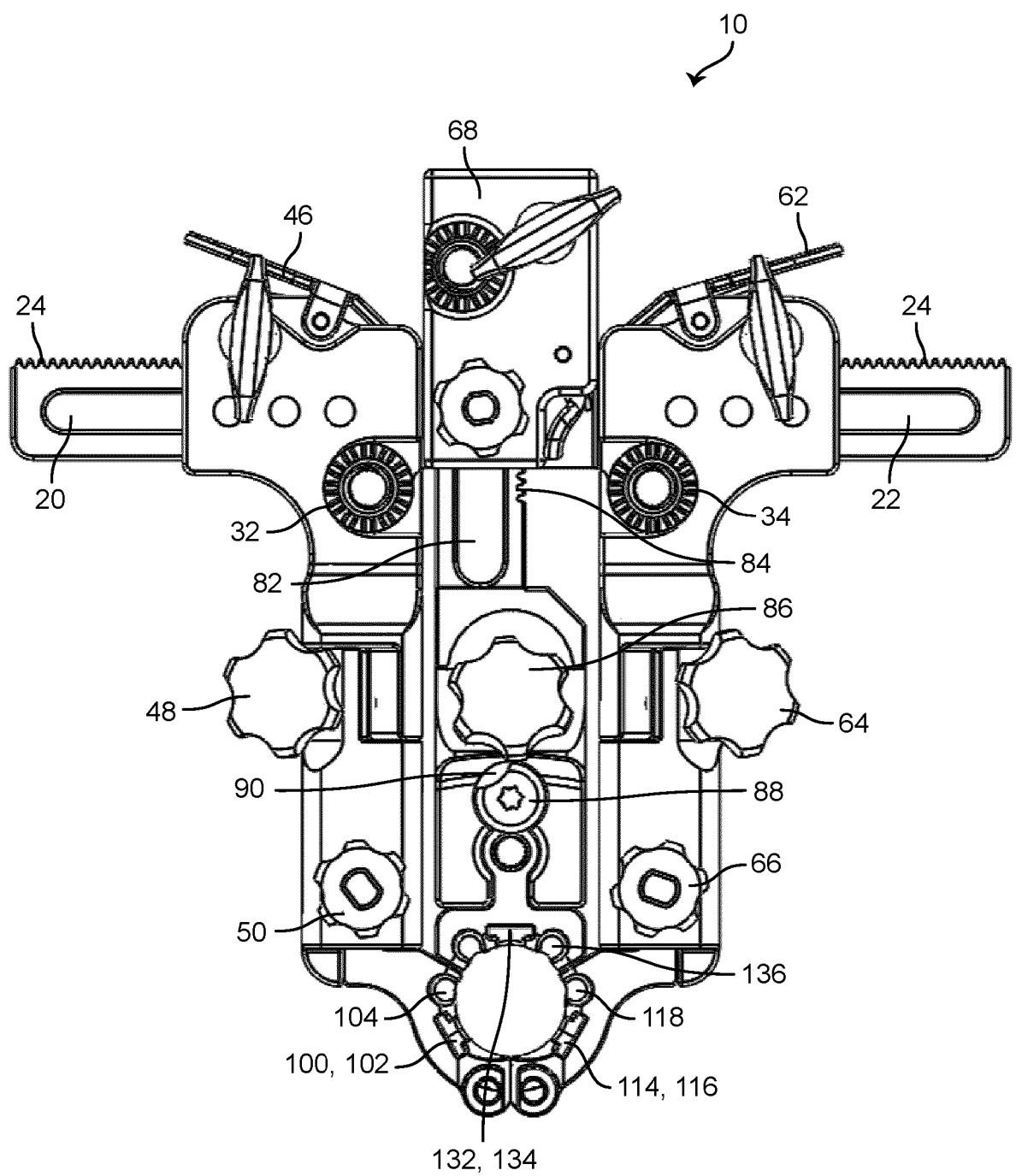
FIG. 3 is a top view of the spinal retractor of FIG. 1 according to one embodiment.

The first side blade assembly 40 is secured to the second arm portion 38 by way of a first side locking knob 50 (see FIG. 3). As shown in greater detail in FIG. 16, the first side locking knob 50 extends through the second arm portion 38 and threadingly engages the first side blade assembly 40. In one embodiment, the first side blade assembly 40 is received by the second arm portion 38 from a bottom direction. In other embodiments, the first side blade assembly 40 may be received from a top direction. Other configurations are possible according to various alternative embodiments.

According to one embodiment, the second side assembly 16 includes a first arm portion 52 and a second arm portion 54. The first arm portion 52 translates along the frame 12, and the second arm portion 54 rotates, or pivots, relative to the first arm portion 52 to provide angulation for a second side blade assembly 56. The first arm portion 52 includes a second side cavity 58 that receives the frame 12, and a second side adjustment knob 60 that engages the frame teeth 24 to move the first arm portion 52, and therefore the second side assembly 16, along the frame 12. The second side adjustment knob 60 is rotatable in opposite directions and engages the frame teeth 24 to provide more or less retraction at a desired site. A second side ratchet mechanism 62 (see FIG. 2) is biased into engagement with the frame teeth 24 to prevent inward movement of the first arm portion 52, and therefore the second side assembly 16, relative to the frame 12 when a user releases the second side adjustment knob 60. The second side ratchet mechanism 62 includes a depressible tab portion that enables a user to release the second side ratchet mechanism 62 and permit free movement of the second side arm assembly 16 along the frame 12.

In some embodiments, a second side angulation knob 64 enables pivotal adjustment of the second arm portion 54 relative to the first arm portion 52 between a normal position (see FIG. 5) and an angulated position (see FIG. 1). As also shown in FIG. 17 with respect to the first side assembly 14, rotation of the second side angulation knob 64 causes the second arm portion 54 to pivot relative to the first arm portion 52, providing a desired degree of angulation to a particular retraction site.

The second side blade assembly 56 is secured to the second arm portion 54 by way of a second side locking knob 66. As shown in greater detail in FIG. 16 with respect to the first side assembly 14, the second side locking knob 66 extends through the second arm portion 54 and threadingly engages the second side blade assembly 56. In one embodiment, the second side blade assembly 56 is received by the second arm portion 54 from a bottom direction. In other embodiments, the second side blade assembly 56 may be received from a top direction. Other configurations are possible according to various alternative embodiments.

The center assembly 18 includes a center housing 68, a first arm portion 70, a second arm portion 72, and a center blade assembly 74. The first arm portion 70 includes a center slot 82 and translates relative to the center housing 68. The second arm portion 72 is pivotally coupled to the first arm portion 70. The center blade assembly 74 is removably secured to the second arm portion 72.

Figure 2:
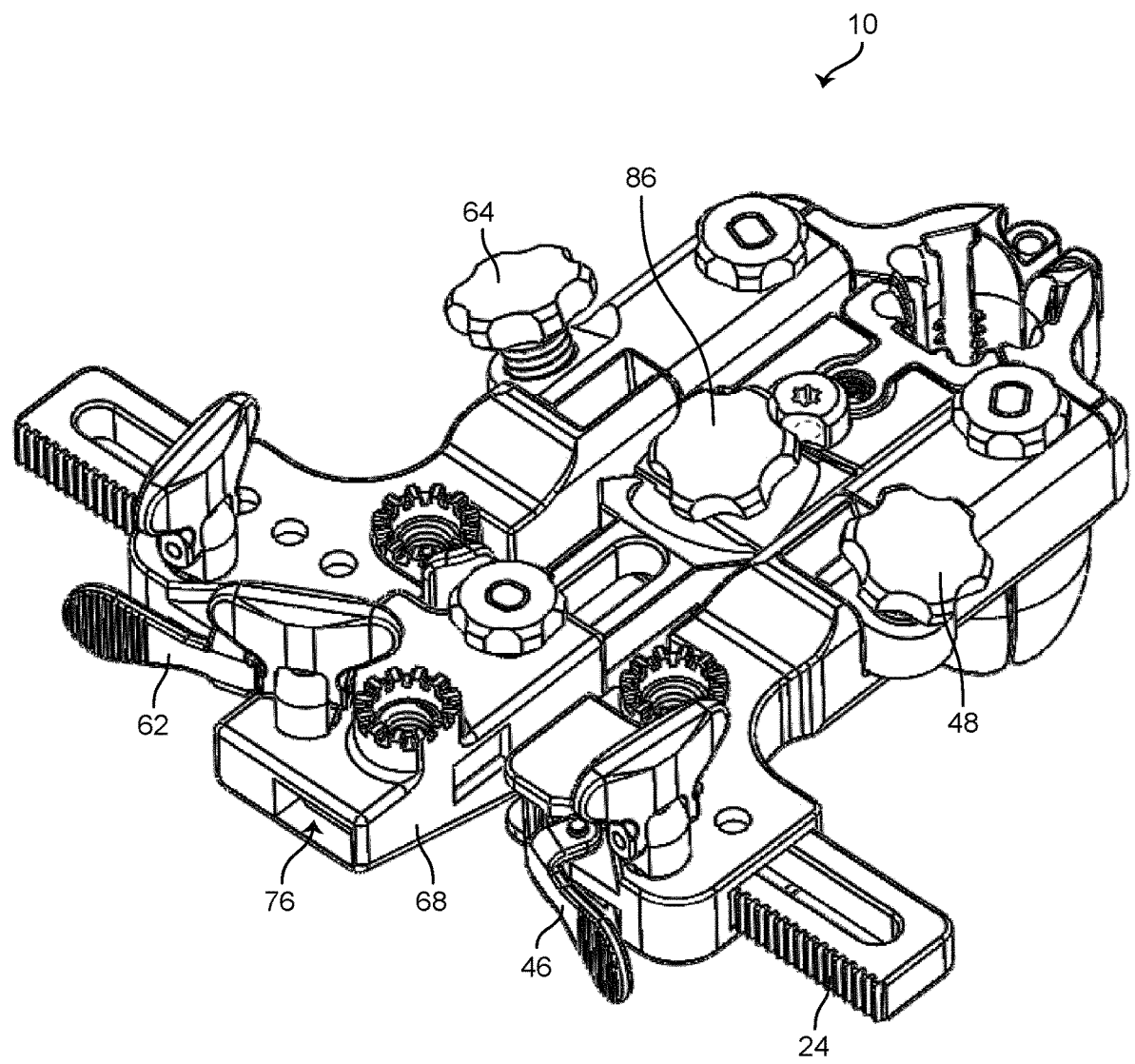
FIG. 2 is another perspective view of the spinal retractor of FIG. 1 according to one embodiment.

Referring further to FIGS. 1-3, the center housing 68 includes a housing cavity 76 that receives the first arm portion 70 and enables translational movement of the first arm portion 70 relative to the center housing 68. A center adjustment knob 78 extends through the center housing 68 and into the housing cavity 76 to engage center teeth 84 provided on the first arm portion 70, such that rotation of the center adjustment knob 78 causes the first arm portion 70 to move into and out of the housing cavity 76. A center ratchet mechanism 80 is biased into engagement with the center teeth 84 to prevent inward movement of the first arm portion 70, and therefore the center assembly 18, relative to the center housing 68 and frame 12 when a user releases the center adjustment knob 78. The center ratchet mechanism 80 includes a depressible tab portion that enables a user to release the center ratchet mechanism 80 and permit free movement of the first arm portion 70 within the housing cavity 76.

In some embodiments, a center angulation knob 86 enables pivotal adjustment of the second arm portion 72 relative to the first arm portion 70 between a normal position (see FIG. 5) and an angulated position (see FIG. 1). Rotation of the center angulation knob 86 causes the second arm portion 72 to pivot relative to the first arm portion 70, providing a desired degree of angulation to a particular retraction site.

The center blade assembly 74 is secured to the second arm portion 72 by way of a center locking screw 88. The center locking screw 88 extends into the second arm portion 72 and locks the center blade assembly 74 into position. In one embodiment, the center blade assembly 74 is received by the second arm portion 72 from a top direction. As shown in FIG. 3, the center locking screw 88 includes a head having a cutout 90 that enables a user to insert and remove the center blade assembly 74 from a top direction relative to the second arm portion 72. When the center blade assembly 74 is in an inserted position, the center locking screw 88 is rotated to move the cutout 90 in the head of the center locking screw 88 such that the center locking screw 88 maintains the center blade assembly 74 in position. Other configurations are possible according to various alternative embodiments.

Figure 4:
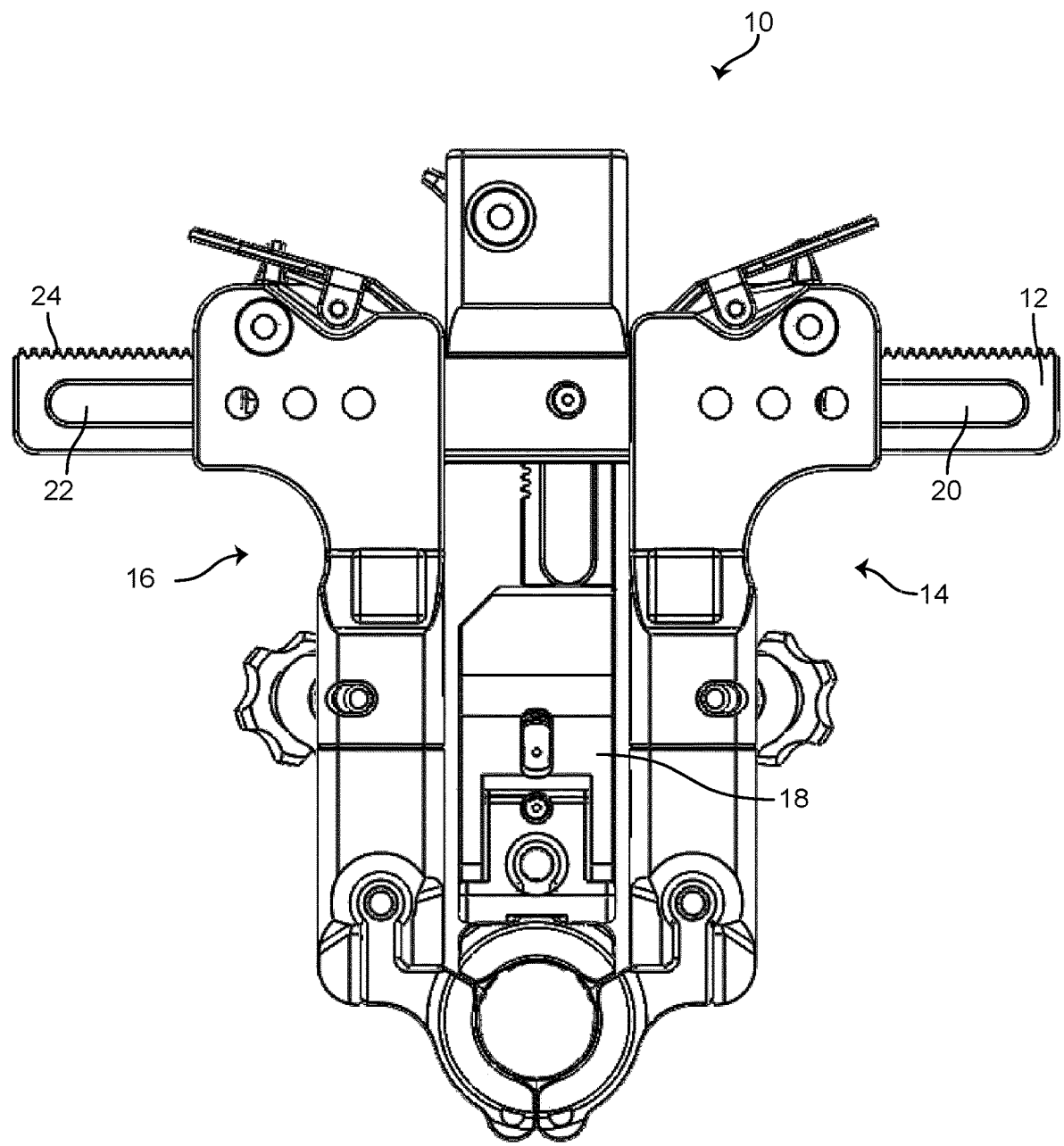
FIG. 4 is a bottom view of the spinal retractor of FIG. 1 according to one embodiment.
Figure 5:
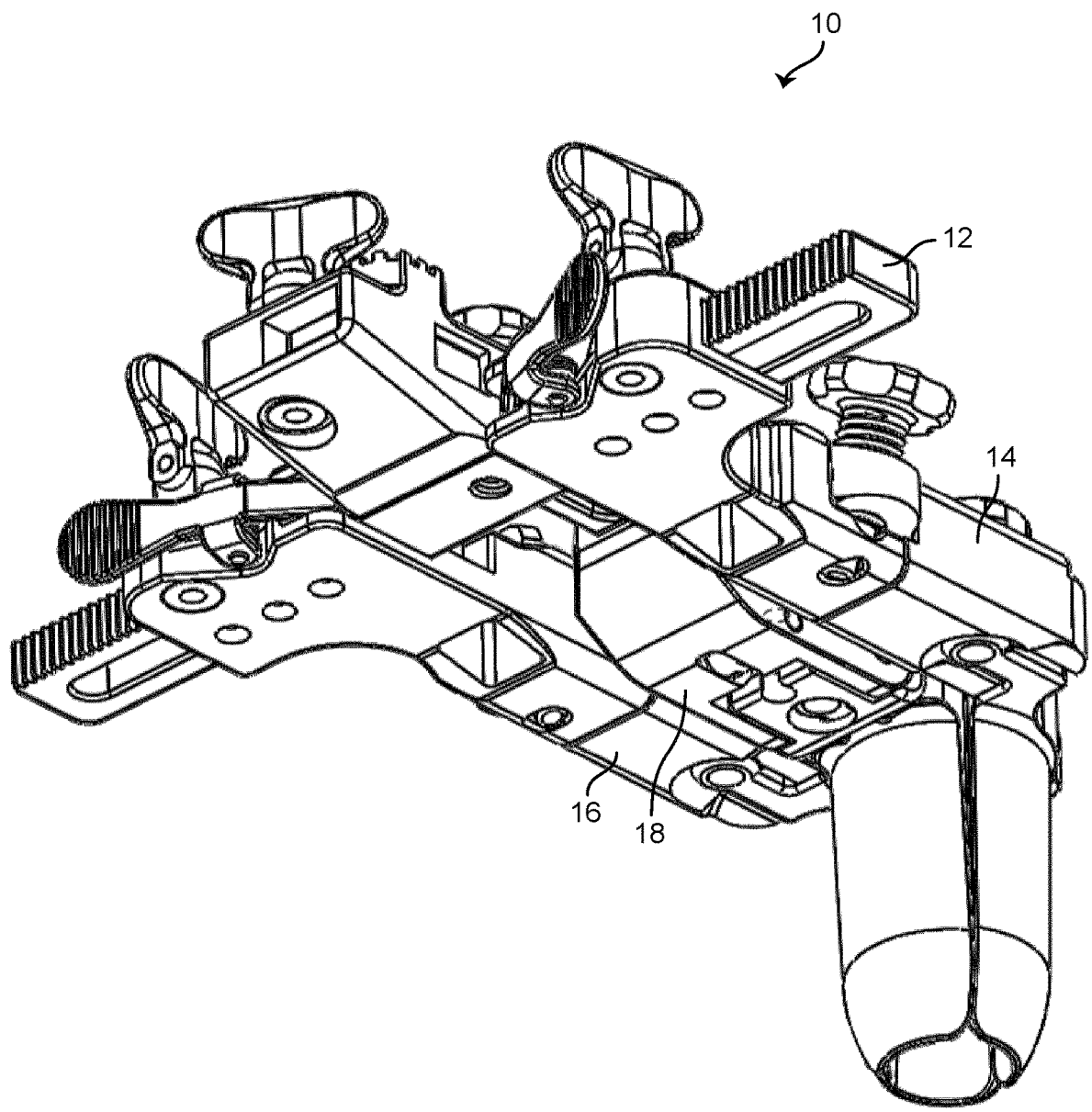
FIG. 5 is another perspective view of the spinal retractor of FIG. 1 according to one embodiment.
Figure 6:
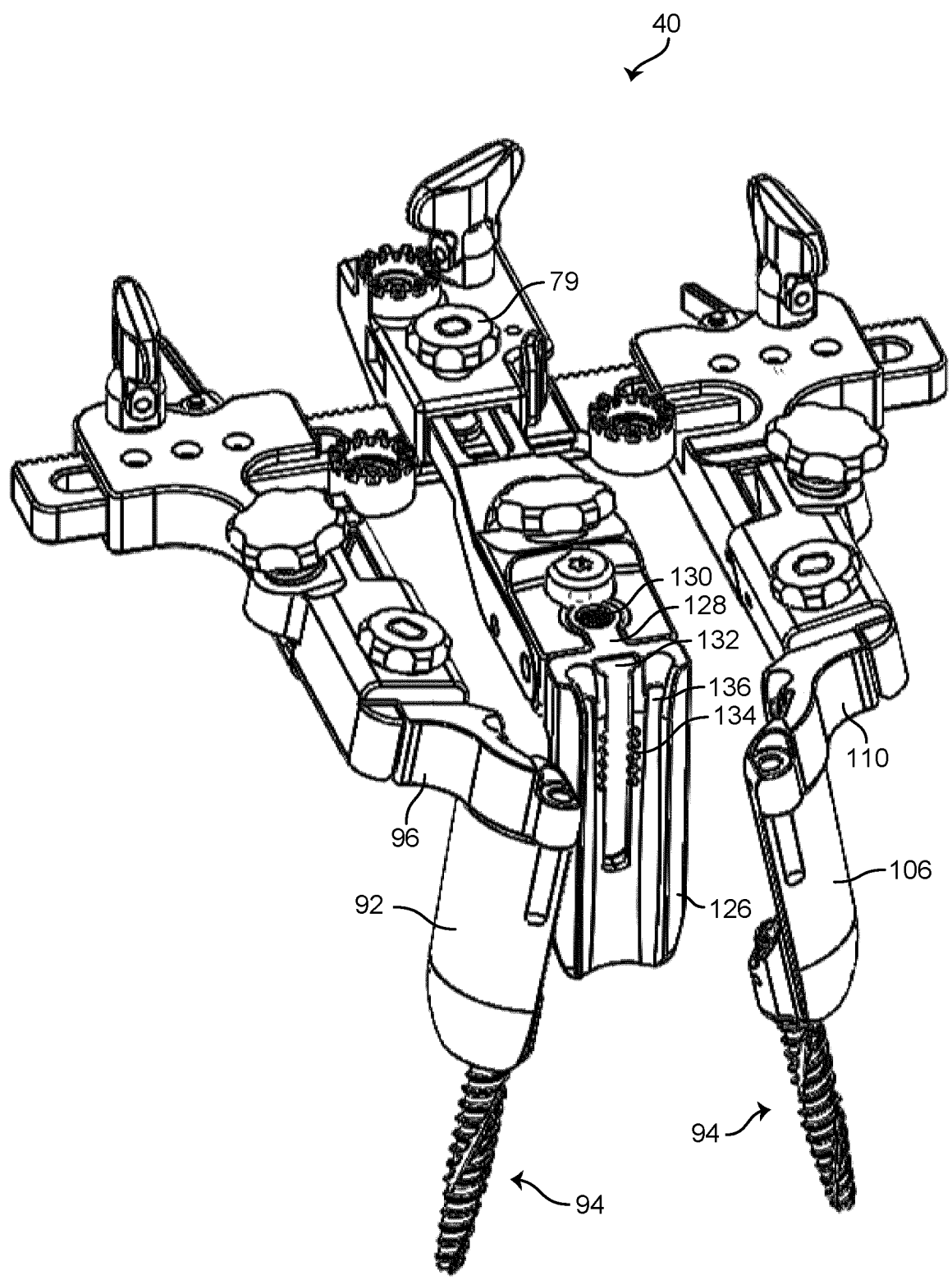
FIG. 6 is a perspective view of the spinal retractor of FIG. 1 including modular tap assemblies according to one embodiment.
Figure 7:
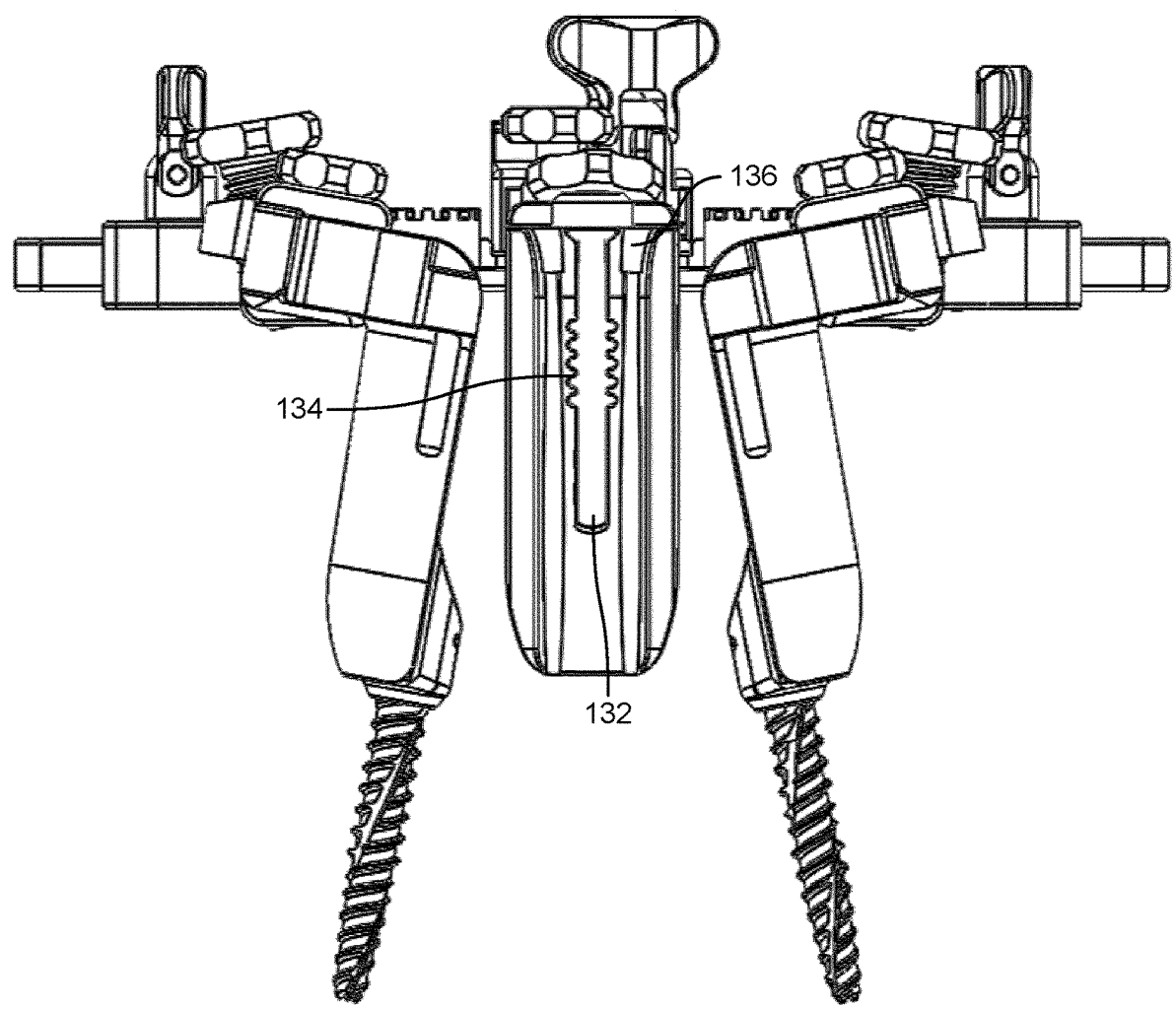
FIG. 7 is a front view of the spinal retractor of FIG. 6 according to one embodiment.
Figure 8:
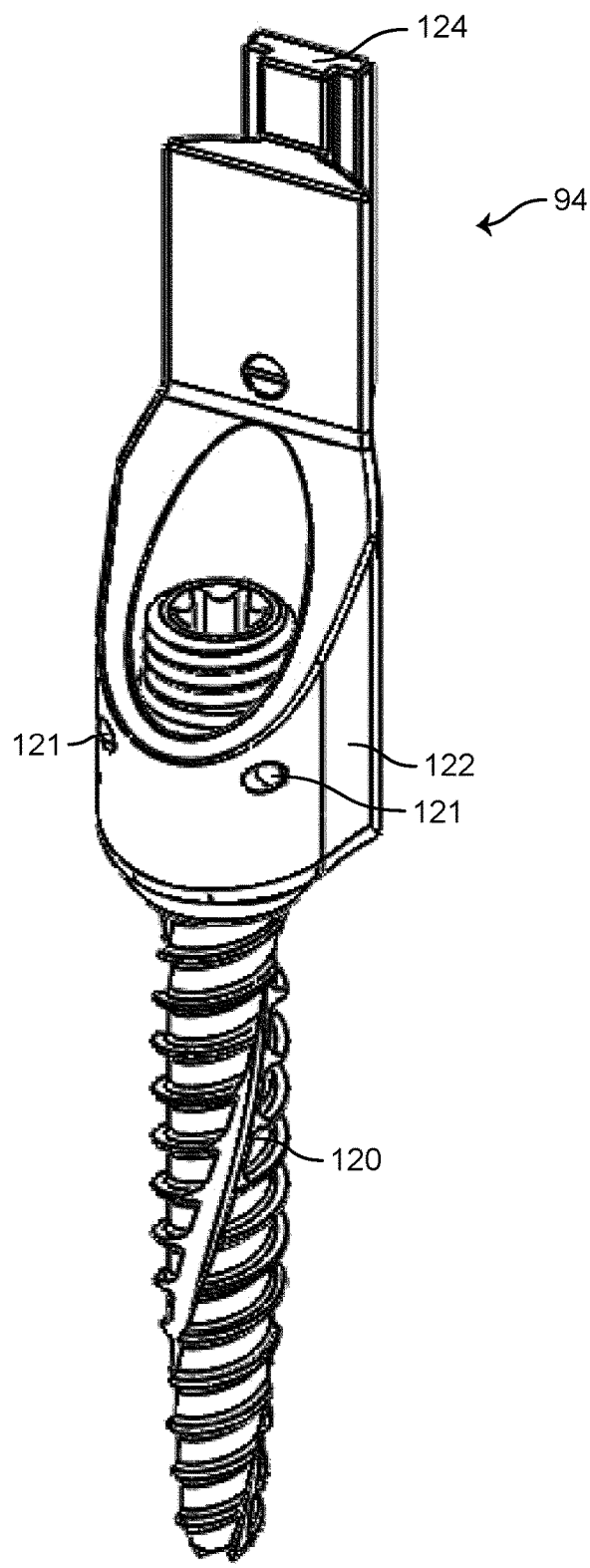
FIGS. 8-11 are views of a modular tap assembly according to one embodiment.
Figure 9:
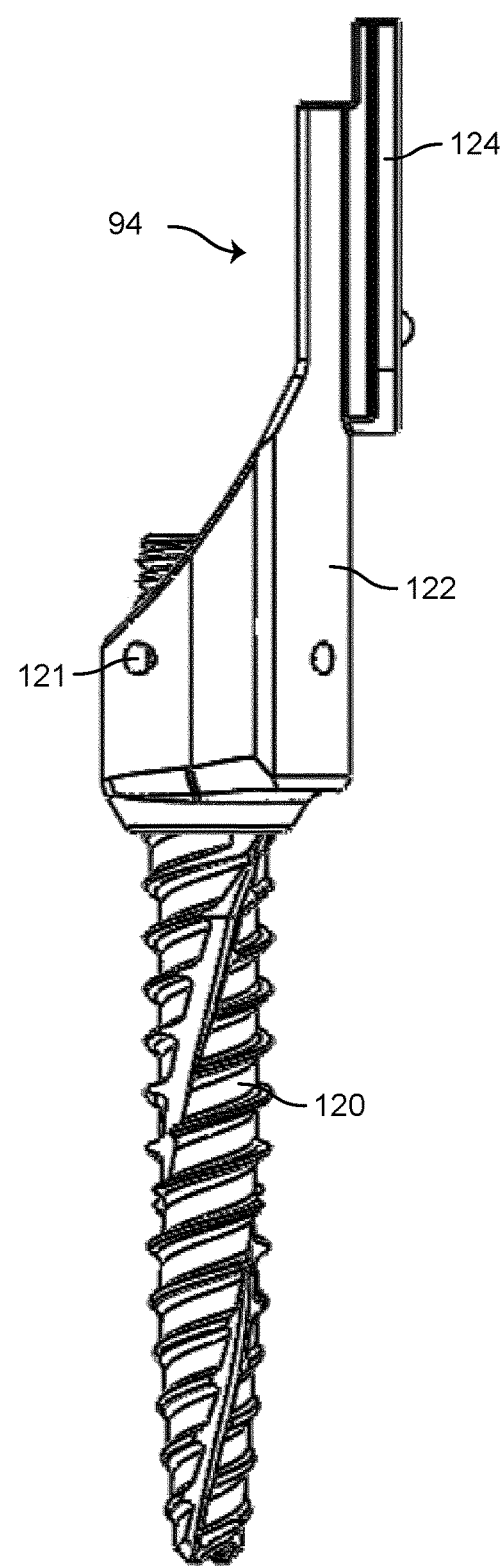
Figure 10:
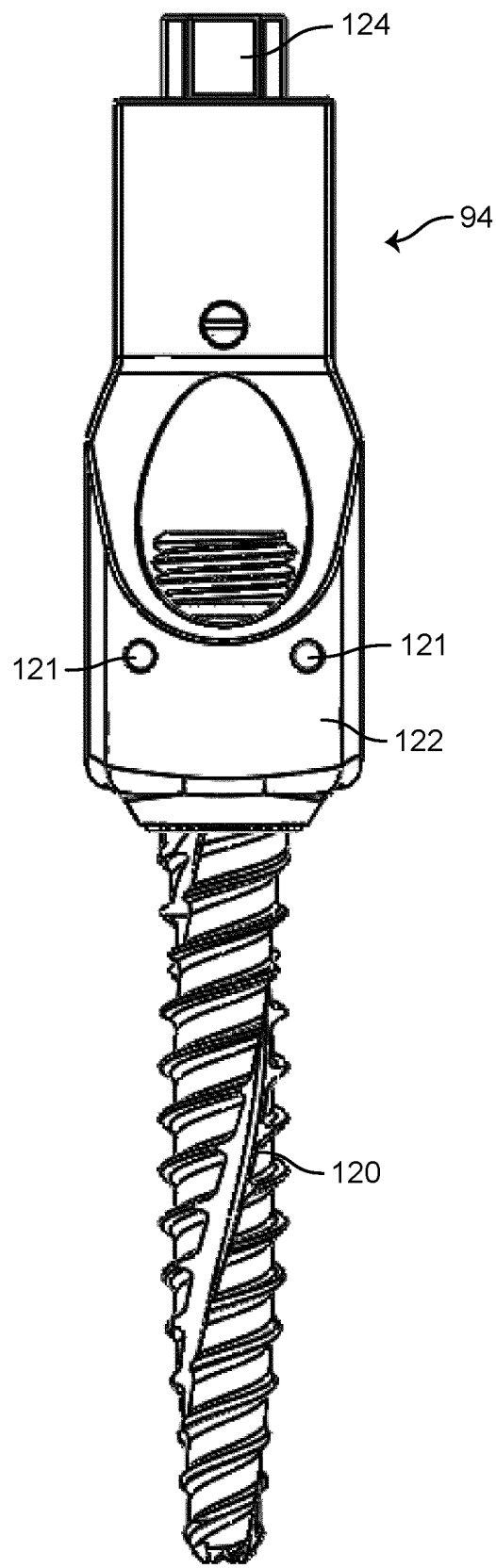
Figure 11:
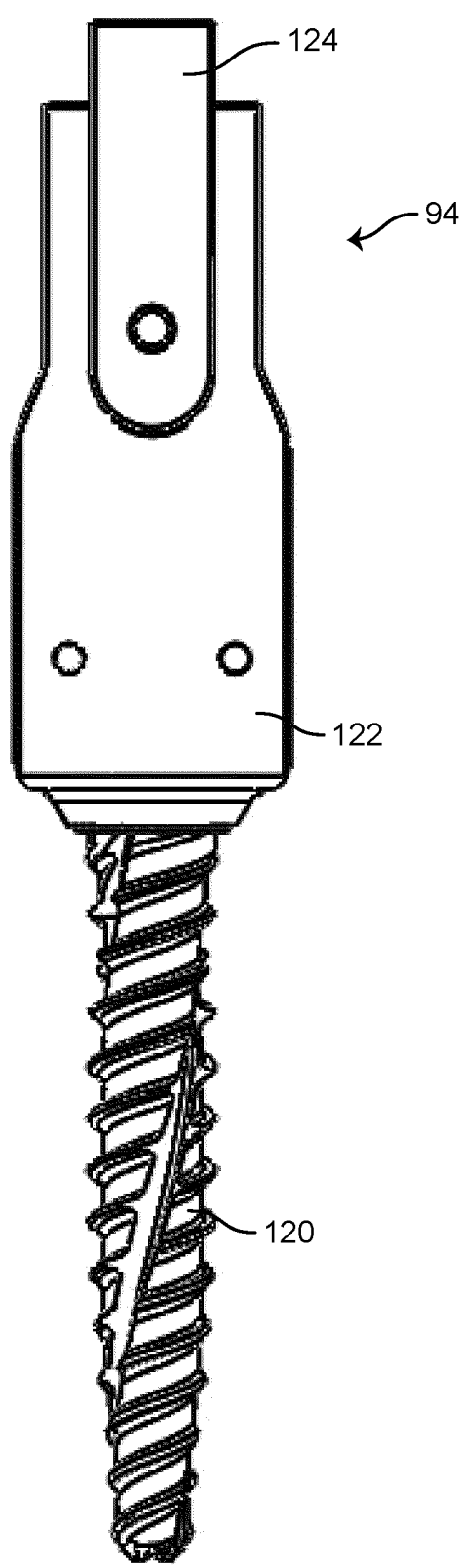

The spinal retractor 10 is movable between an open configuration, shown in FIG. 1, to a closed configuration, shown in FIGS. 2-4, through translation of the first side assembly 14 and the second side assembly 16 and/or the center assembly 18 relative to the frame 12. Furthermore, the first side assembly 14, the second side assembly 16, and the center assembly 18 receive the first side, second side, and center blade assemblies 40, 56, 74, which are configured to hold tissue apart during various procedures. The blade assemblies 40, 56, 74 may be angulated (e.g., moved from a generally vertical, parallel orientation to one or more non-vertical, or angled, orientations) to suit a particular procedure.

Referring now to FIGS. 6-13, in one embodiment, the first side blade assembly 40 includes a first side blade 92, a modular tap assembly 94, and a first side attachment arm 96. The first side attachment arm 96 includes a first side locking aperture 98 that receives the first side locking knob 50. The first side blade 92 extends downward from the first side attachment arm 96, and the modular tap assembly 94 is removably received by the first side blade 92. The second side blade assembly 56 includes a second side blade 106, a modular tap assembly 94, and a second side attachment arm 110. The second side attachment arm 110 includes a second side locking aperture 112 that receives the second side locking knob 66. The second side blade 106 extends downward from the second side attachment arm 110, and the modular tap assembly 94 is removably received by the second side blade 106. The center blade assembly 74 includes a center blade 126 and a center attachment arm 128. The center blade 126 extends downward from the center attachment arm 128. A center aperture 130 receives the center locking knob to secure the center blade assembly in place.

Figure 12:
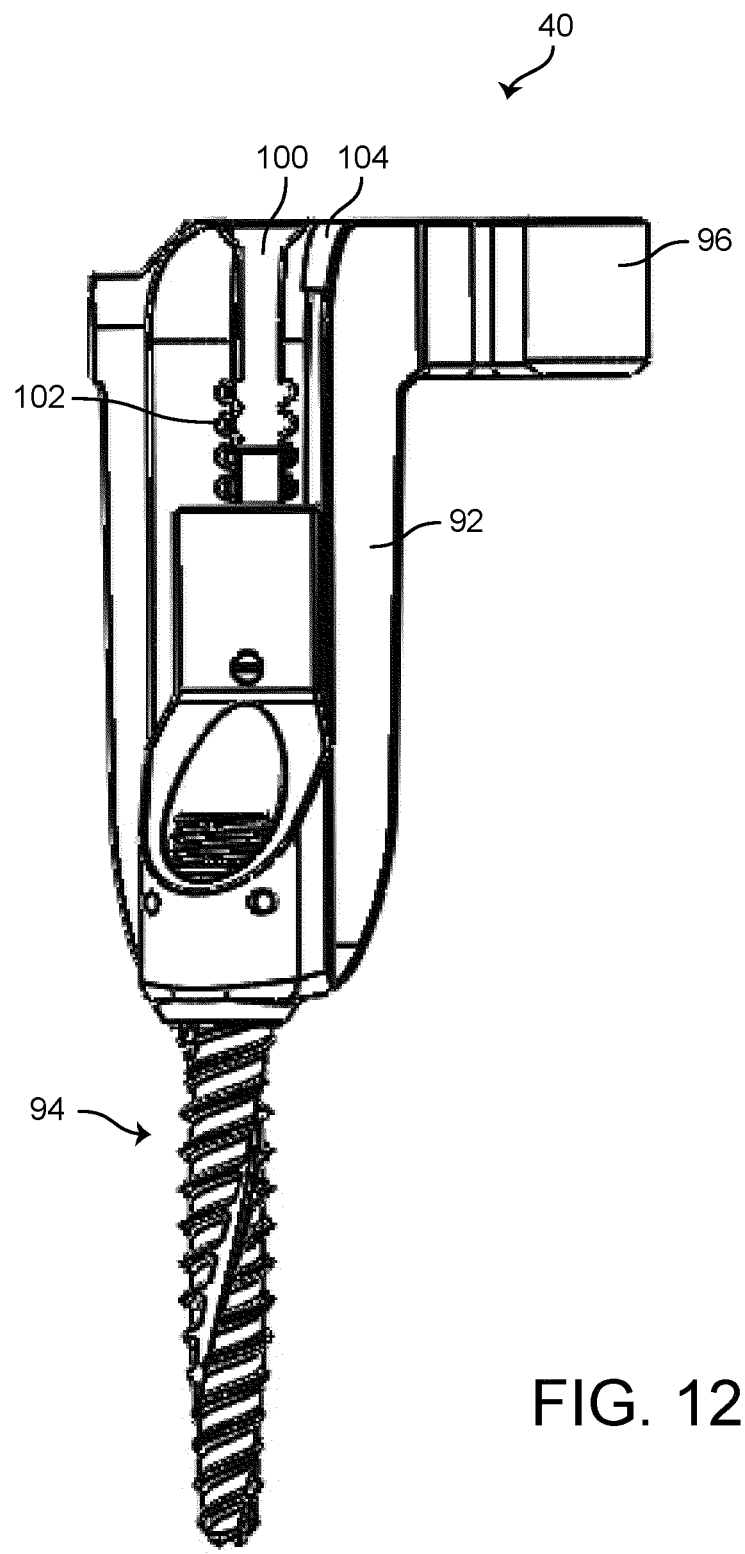
FIG. 12 is a side view of a blade assembly according to one embodiment.

Referring to FIGS. 3 and 12, in one embodiment, the first side blade 92 includes a first side channel 100 and a one or more blade channels 104. The first side channel 100 includes a plurality of notches 102 configured to enable selective positioning of the modular tap assembly 94 within the first side channel 100. The second side blade 106 includes a second side channel 114 and a one or more blade channels 118. The second side channel 114 includes a plurality of notches 116 configured to enable selective positioning of the modular tap assembly 94 within the second side channel 114. The blade channels 118 enable placement of additional positioning pins, lighting devices, etc., via the second side blade 106. The center blade 126 includes a center channel 132 and one or more blade channels 136. The center channel 132 includes one or more notches 138 configured to enable selective positioning of secondary blade 148 within center channel 132. Alternatively, center channel 132 may be configured to receive a modular tap assembly such as modular tap assembly 94.

Referring to FIGS. 8-11, in one embodiment, the modular tap assembly 94 includes a tap or screw 120, a sleeve 122, and a rail 124. The screw 120 is retained within the sleeve 122, and rotates freely relative to the sleeve 122. In some embodiments, the screw 120 is retained in position by pins 121 that extend through sleeve 122 and are received in a slot or groove in the head of the screw 120, such that the screw 120 is free to rotate but is translationally fixed relative to the sleeve 122. The rail 124 extends along a length of the sleeve 122, and is configured to engage the first side channel 100 and the second side channel 114 of the first side blade assembly 40 and the second side blade assembly 56, respectively. As shown in FIGS. 44-45, the modular tap assembly 94 may be slid from a bottom direction to couple with the first side blade assembly 40 and the second side blade assembly 56. The rail 124 may include projections or other features configured to engage the notches 102, 116 in the first side channel 100 and the second side channel 114 to enable selective placement of the modular tap assemblies 94 within the first and second side blade assemblies 40, 56.

Figure 13:
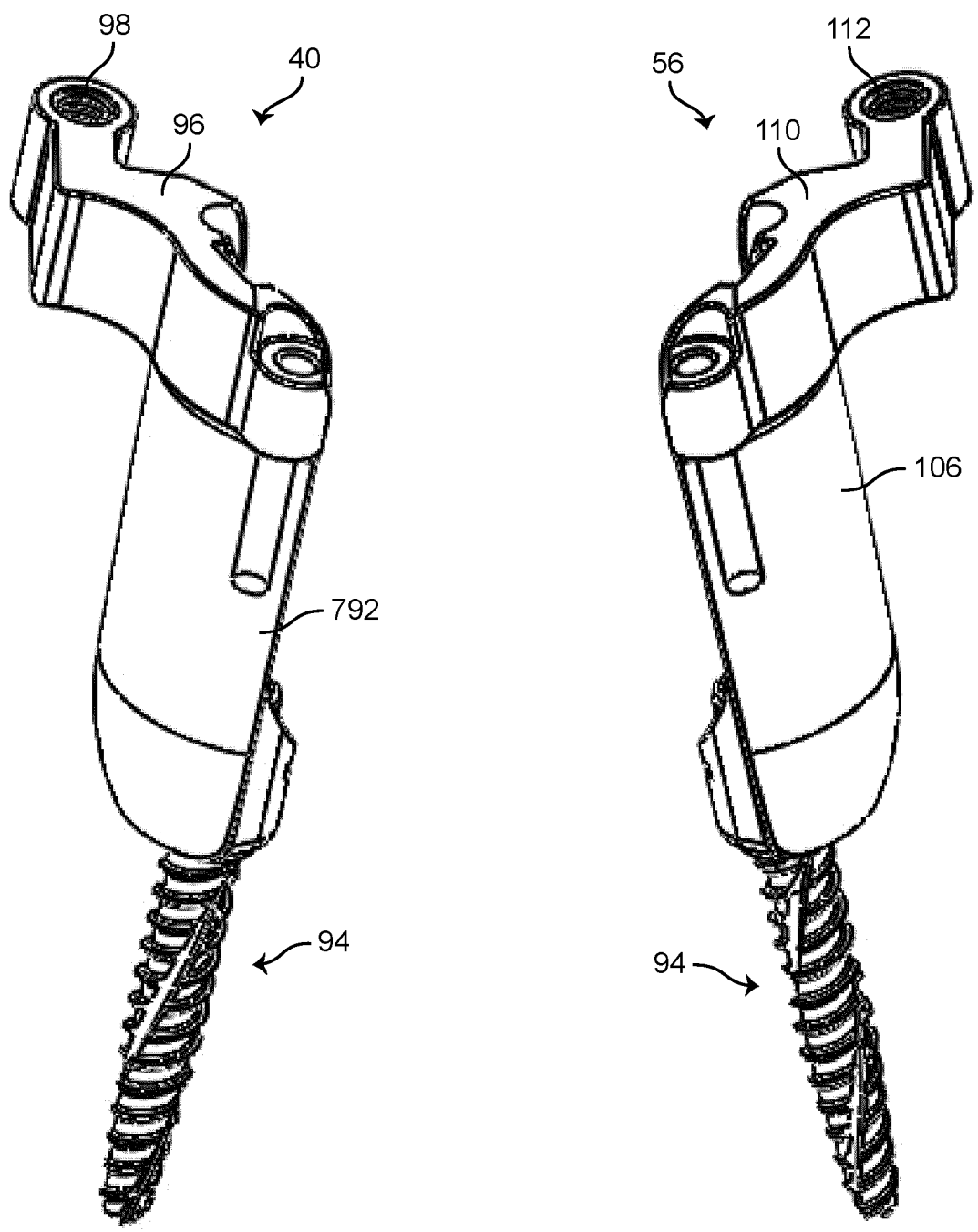
FIG. 13 is a perspective view of first and second blade assemblies according to one embodiment.
Figure 15:
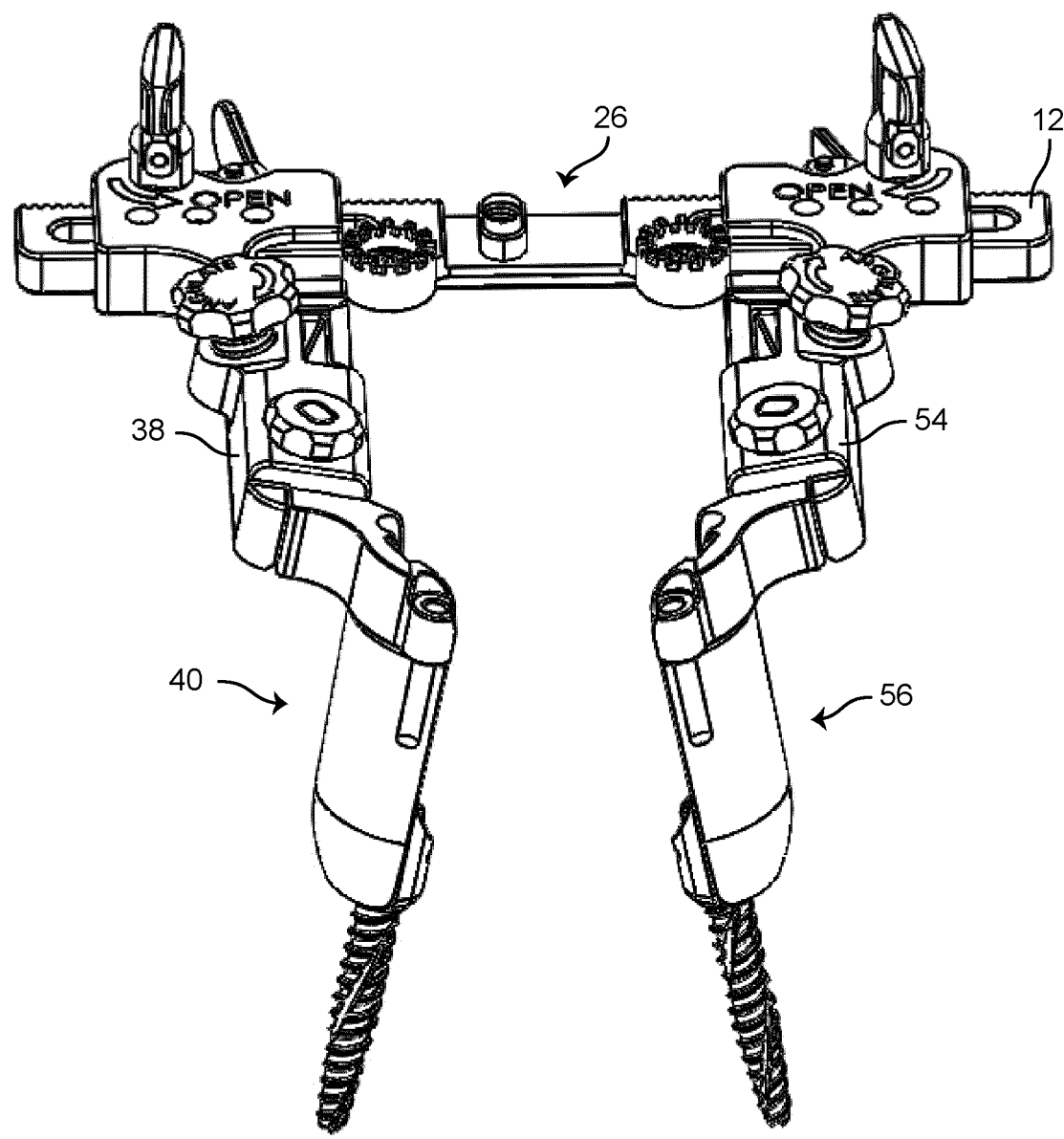
FIG. 15 is a perspective view of a spinal retractor with a center assembly decoupled according to one embodiment.
Figure 16:
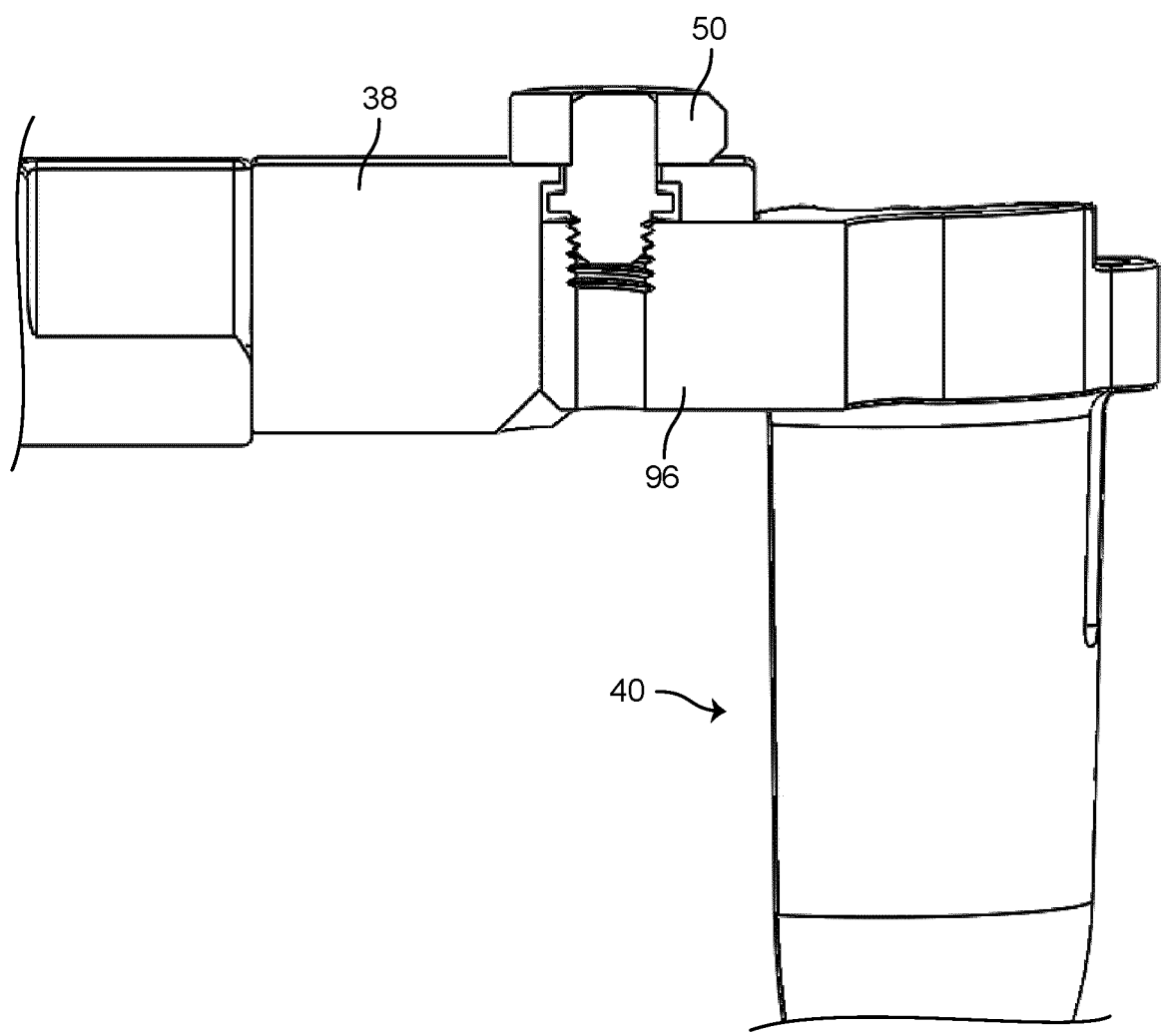
FIGS. 16-17 are partial cross-sectional views of the retractor assembly of FIG. 1 according to one embodiment.

In use, the first and second side blade assemblies 40, 56 are coupled to the modular tap assemblies 94, as shown in FIGS. 12-13. The modular tap assemblies 94 are then secured in desired positions, for example, by threading the screw 120 into one or more desired bone structures. Once the modular tap assemblies 94 are properly positioned, the first and second side blade assemblies 40, 56 are coupled to the second arm portions 38, 54 of the first and second side assemblies 14, 16, as shown in FIGS. 14-15 (e.g., from a bottom direction). Once the first and second side blade assemblies 40,56 are secured in position, the center assembly 18 is secured in position, as shown in FIG. 18 (e.g., from a top direction), by positioning the center housing 68 within the frame recess 26, and threading the center locking knob 79 into the boss aperture 30 of the central boss 28.

Figure 18:
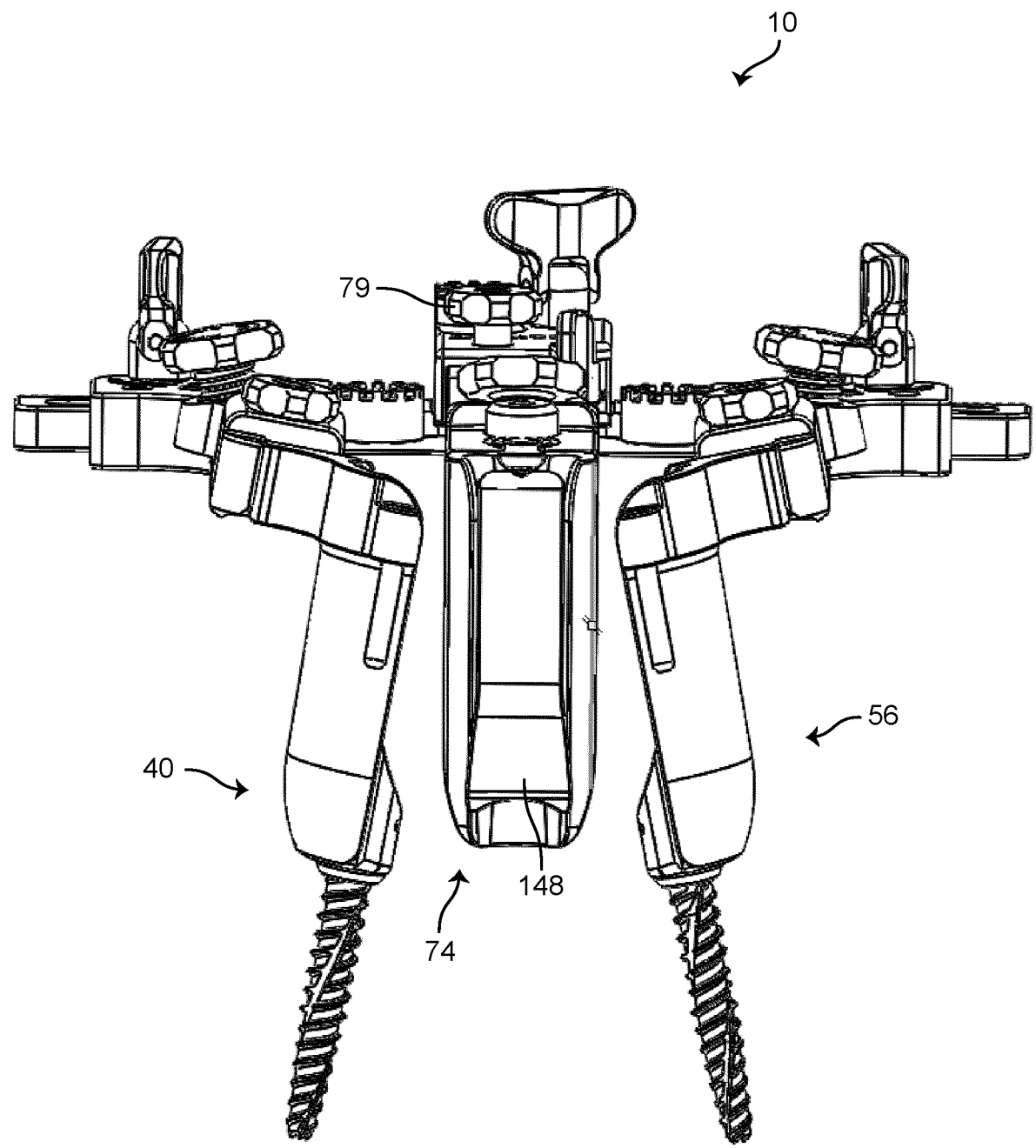
FIGS. 18-19 are views of a spinal retractor with a secondary blade according to one embodiment.
Figure 19:
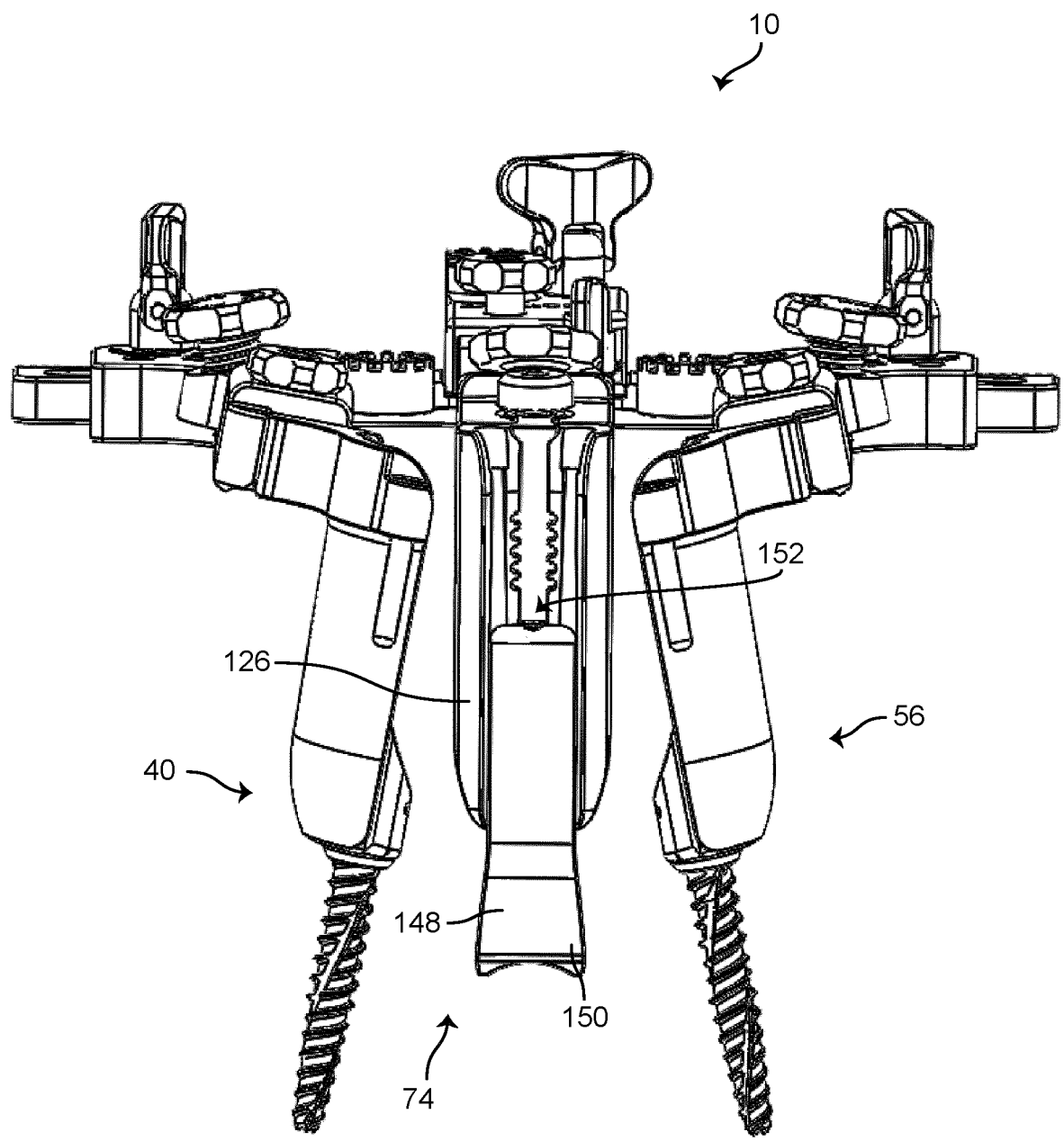

Referring to FIGS. 18-19, if desired, the secondary blade 148 may be slid into the center blade 126 by way of the center channel 132. The secondary blade 148 includes a flared portion 150 and a rail 153 received within the center channel 132. The rail 153 of the secondary blade 148 may include projections or other features to enable selective engagement with the notches 134 of the center channel 132 and positioning of the secondary blade 148.

Figure 20:
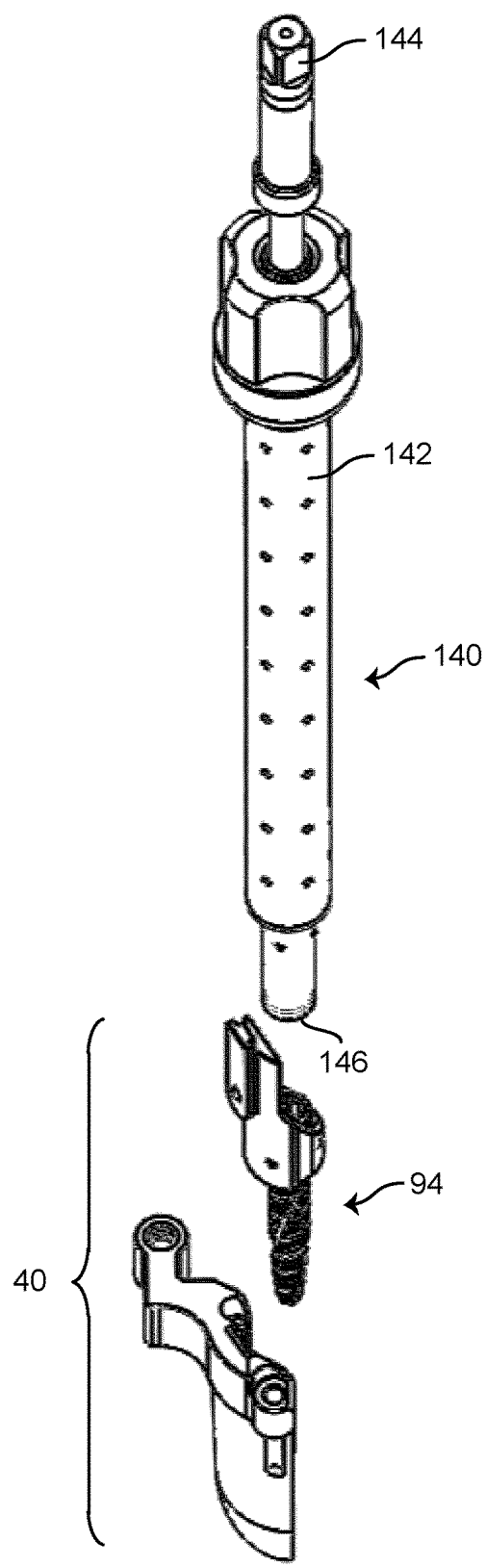
FIGS. 20-22 are views of a driver assembly usable with a spinal retractor according to one embodiment.
Figure 21:
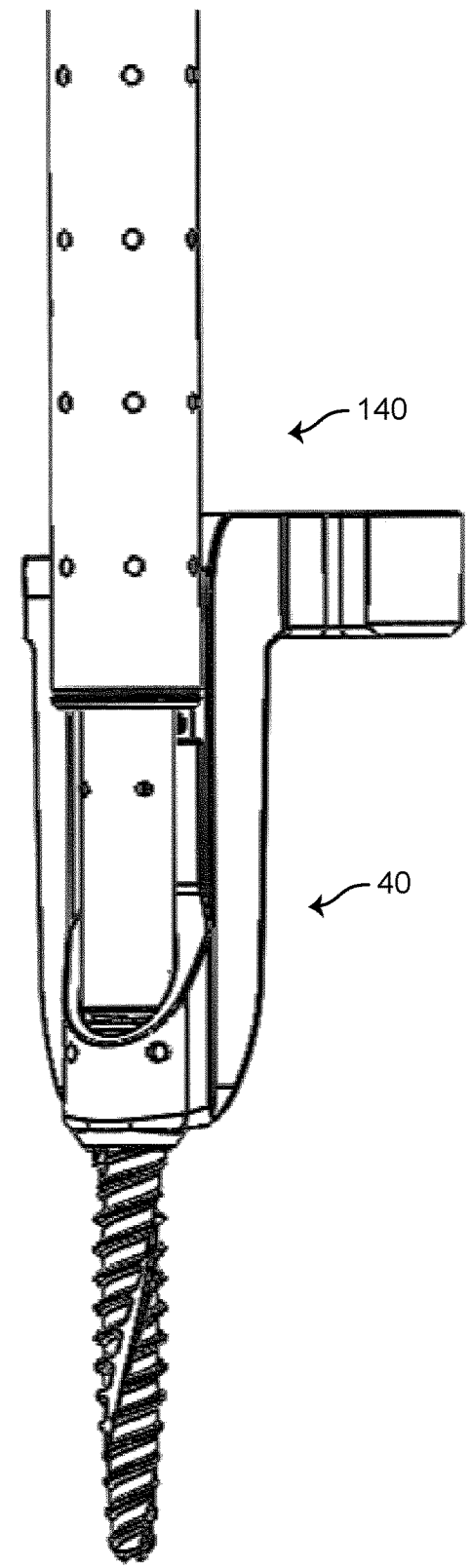
Figure 22:
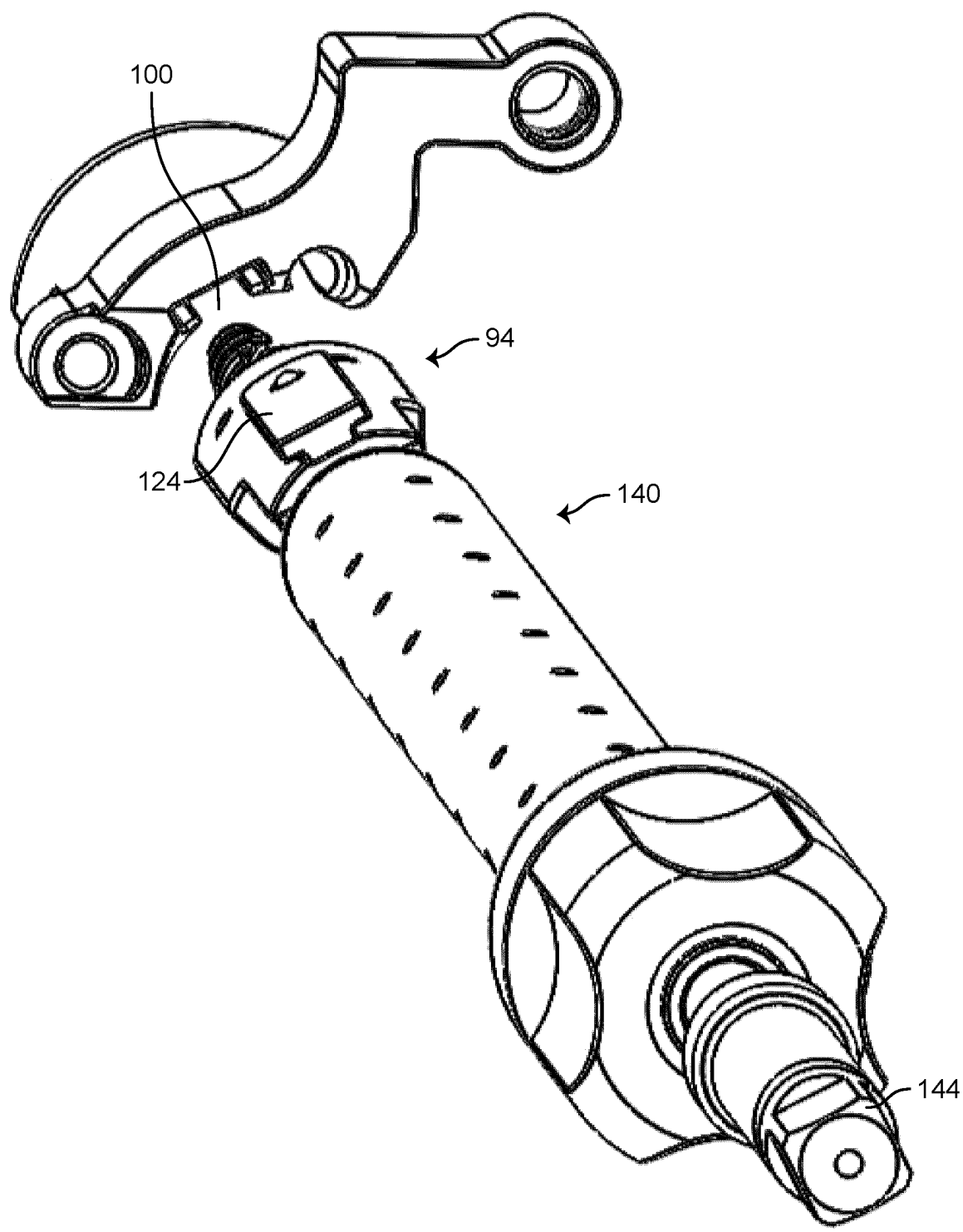

Referring now to FIGS. 20-22, a driver assembly 140 usable to install a blade assembly such as the first side blade assembly 40 is shown according to one embodiment. The driver assembly 140 includes an outer housing 142, a top drive member 144, and a bottom drive member 146. The bottom drive member 146 is configured to mate with the screw 120 of the modular tap assembly 94, and the top drive member 144 is configured to mate with an appropriate tool (e.g., a driver, etc.), such that rotation of the top drive member 144 results in a corresponding rotation of the bottom drive member 146 and the screw 120. In some embodiments, as shown in FIGS. 21-22, the driver assembly 140 is usable when the modular tap assembly 94 is coupled to a blade assembly such as the first side blade assembly 40 or the second side blade assembly 56.

Figures 23, 24:
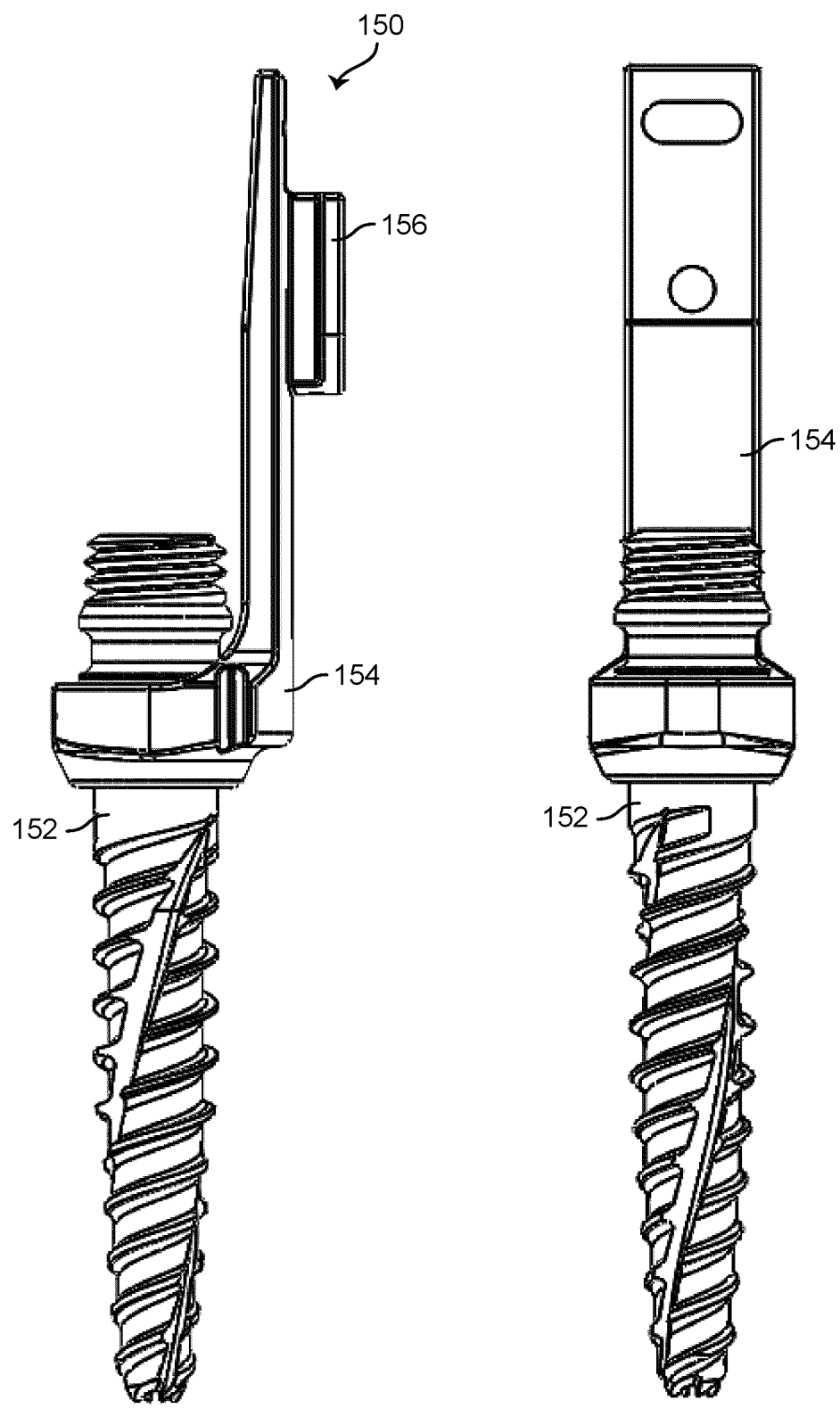
FIGS. 23-25 are views of a modular tap assembly according to an alternative embodiment.
Figure 25:
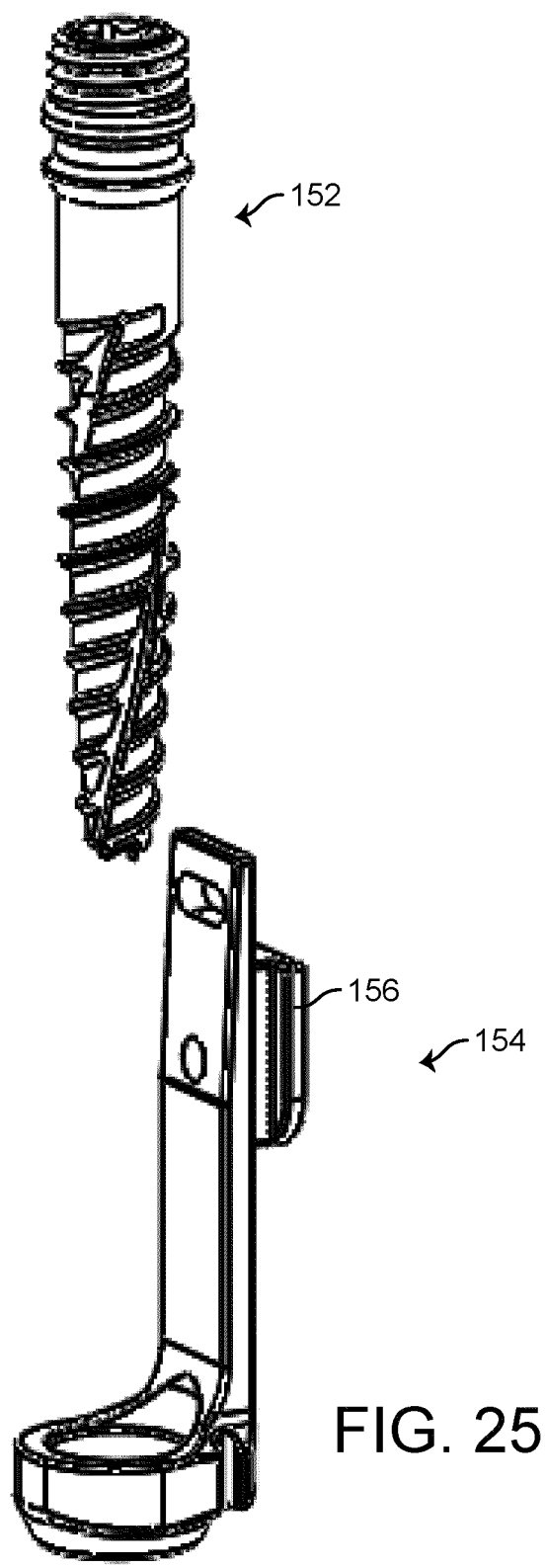
Figure 26:
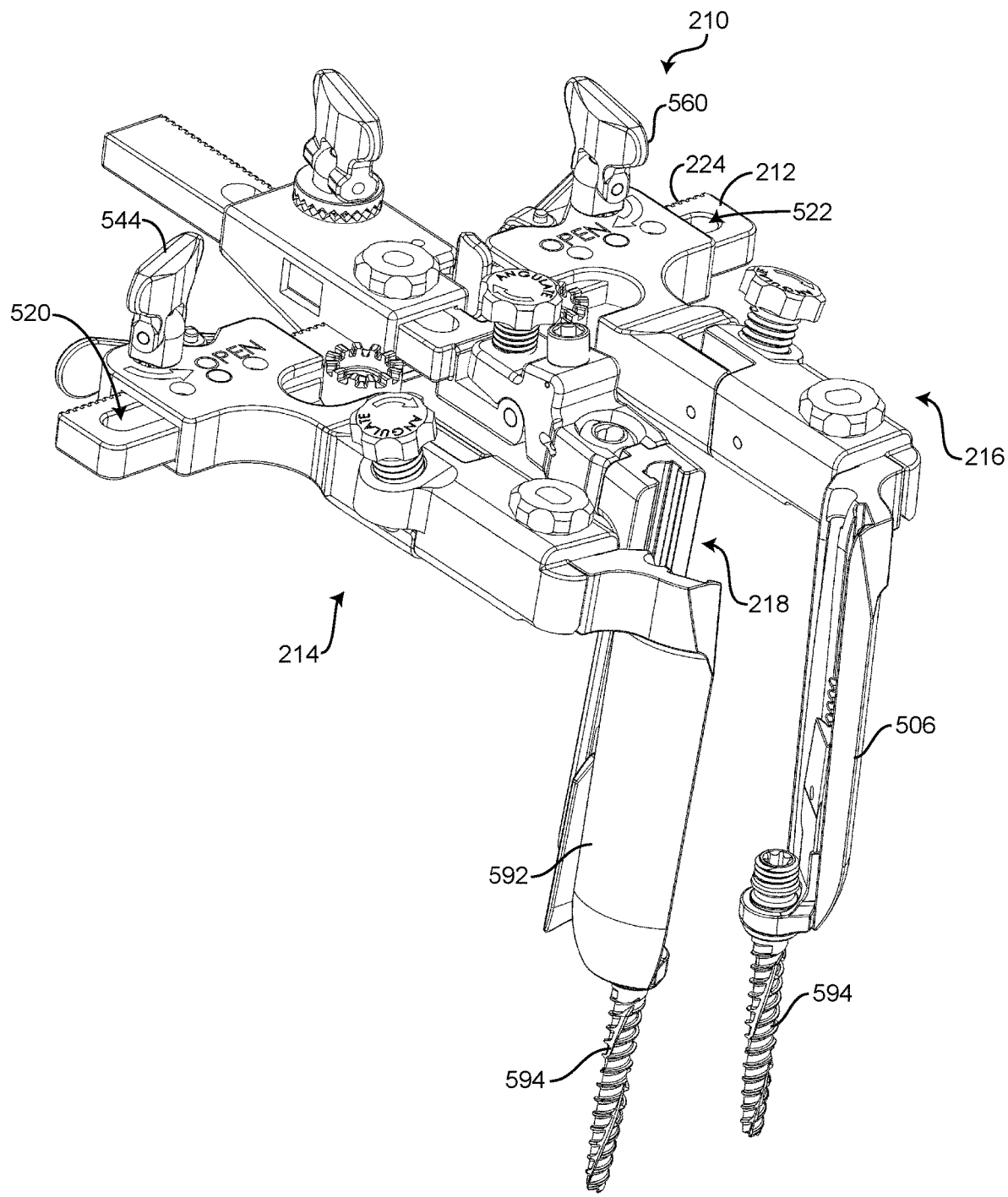
FIGS. 26-27 are a perspective view of a spinal retractor, according to an alternative embodiment.
Figure 27:
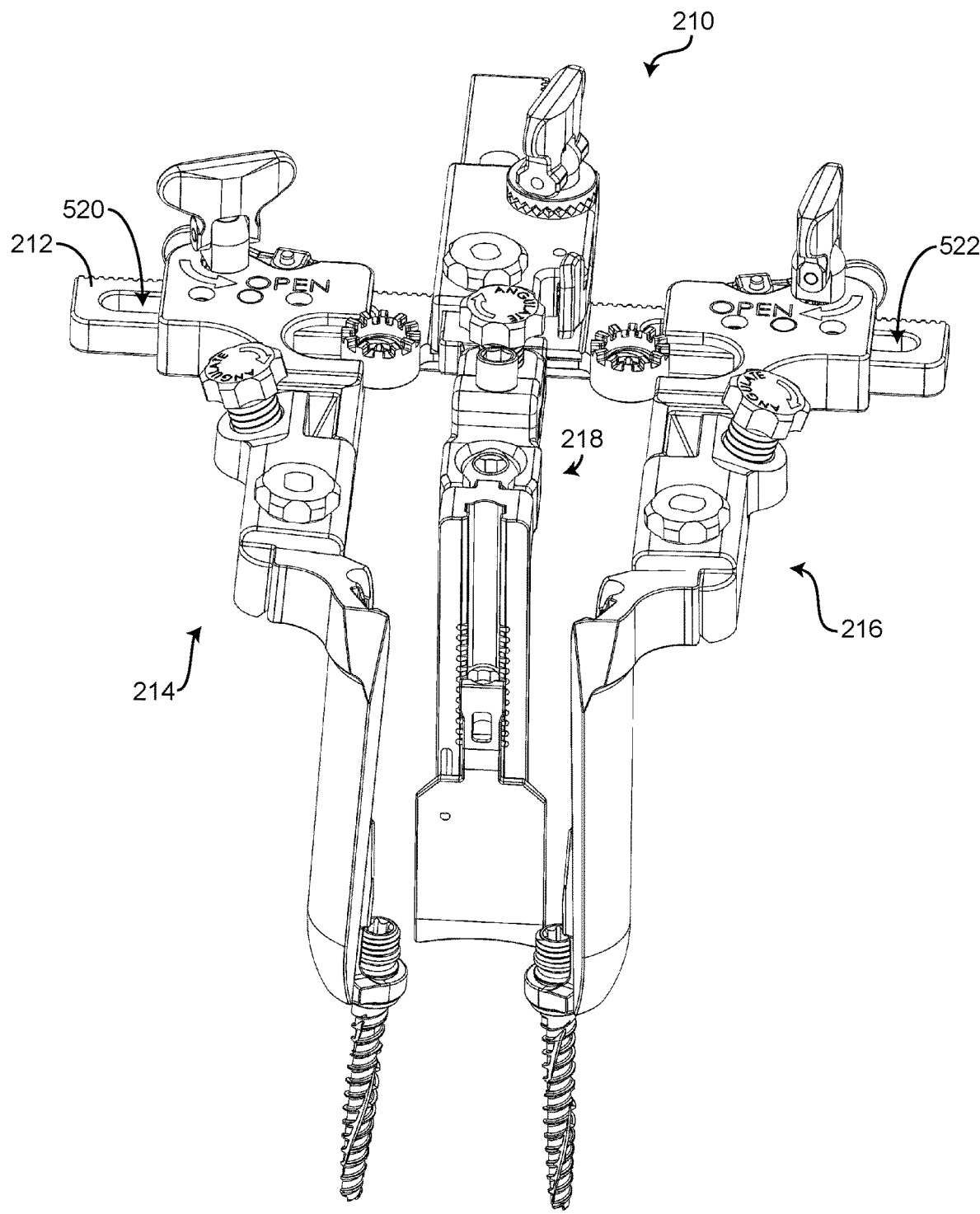
Figure 28:
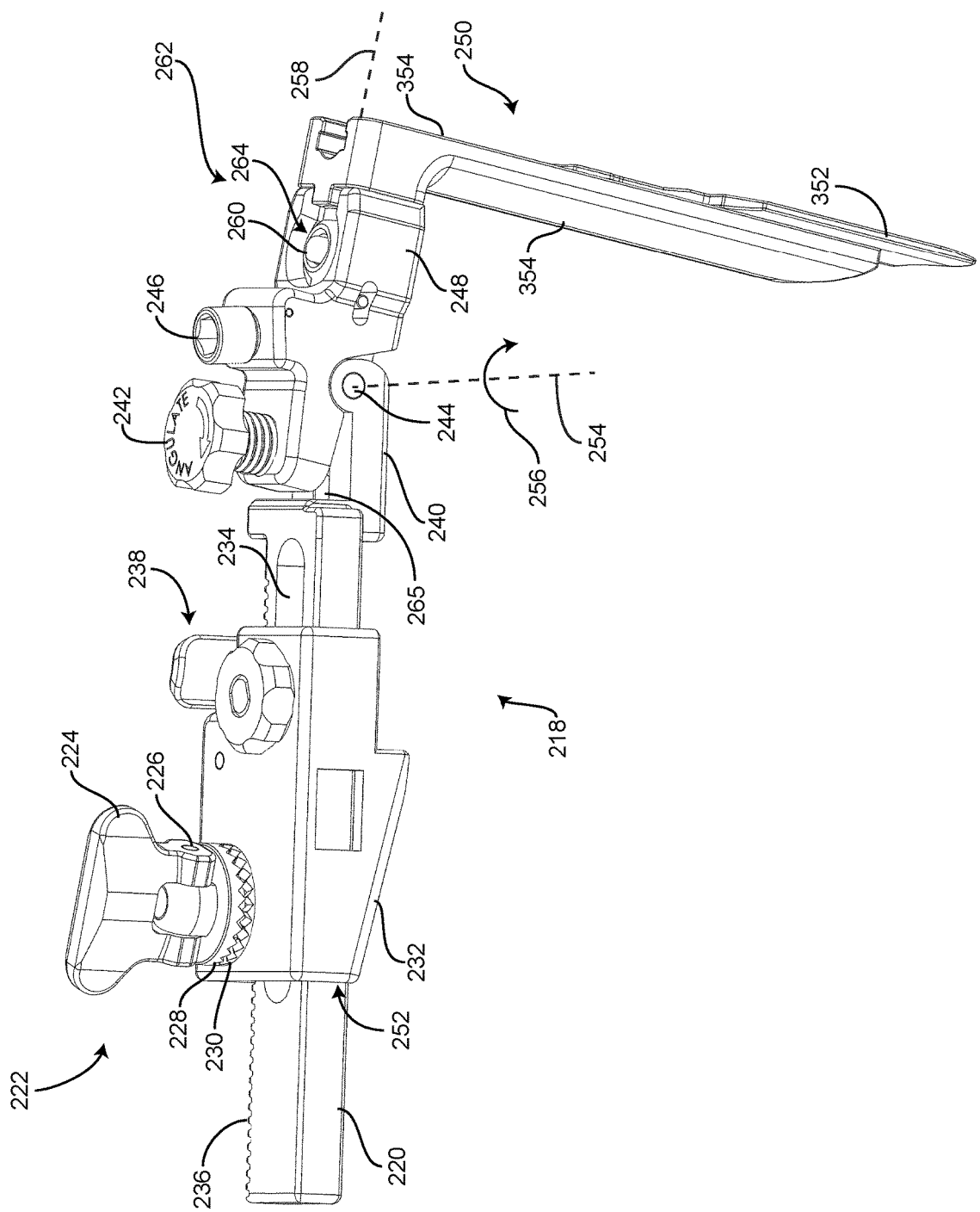
FIGS. 28-33 are perspective views of a medial arm of the spinal retractor of FIGS. 26-27, configured to pivot or rotate about multiple axes, according one embodiment.

In some embodiments, an alternative modular tap assembly may be used in place of or in combination with the modular tap assembly 94. For example, as shown in FIGS. 23-25, a modular tap assembly 150 includes a tap or screw 152, a sleeve 154, and a rail 156. The modular tap assembly 150 interfaces with the other components described herein in a similar manner as the modular tap assembly 94, and has similar structural features, with the exception that the screw 152 is not translationally fixed relative to the sleeve 154, but rather engages the sleeve 154 as shown in FIG. 25. As such, the screw 152 is slid into sleeve 154 prior to being secured to any bone material.

Referring now to FIGS. 26-46, a spinal retractor 210 is shown according to another embodiment. Spinal retractor 210 includes frame 212 and first and second side assemblies 214 and 216 configured to translate along frame 212. First and second side assemblies 214 and 216 may include any features of first and second side assemblies 14 and 16 to facilitate movement along frame 212 described in greater detail above with reference to FIGS. 1-25. For example, first and second side assemblies 214 and 216 are shown to include first side adjustment knob 544 and second side adjustment knob 560. First side adjustment knob 544 and second side adjustment knob 560 may be the same or similar to first side adjustment knob 44 and second side adjustment knob 60, respectively, as described in greater detail above with reference to FIGS. 1-25. Likewise, frame 212 may include any or all features of frame 12 as described in greater detail above with reference to FIGS. 1-25, or may include features similar to the features of frame 12 as described in greater detail above with reference to FIGS. 1-25. For example, frame 212 is shown to include first side slot 520 and second side slot 522. First side slot 520 may be the same as or similar to first side slot 20, and second side slot 522 may be the same as or similar to second side slot 22 as described in greater detail above with reference to FIGS. 1-25. First and second side assemblies 214 and 216 are configured to selectably actuate along frame 212 and may include first side blade 592, second side blade 506, respectively, and modular tap assembly 594. First side blade 592 may be the same as or share any of the features of first side blade 92 as described in greater detail above with reference to FIGS. 1-25. Likewise, second side blade 506 may be the same as or share any of the features of second side blade 106 as described in greater detail above with reference to FIGS. 1-25. Modular tap assembly 594 may be the same as or share any of the features of modular tap assembly 94 as described in greater detail above with reference to FIGS. 1-25. Spinal retractor 210 includes medial arm 218. Medial arm 218 may include any of the features described in greater detail above with reference to center assembly 18. In some embodiments, spinal retractor 210 is the same as spinal retractor 10, except for the additional and/or different features described in greater detail below with reference to FIGS. 26-46.

Referring now to FIGS. 28-36, medial arm 218 is shown in greater detail, according to an exemplary embodiment. Medial arm 218 is configured to translate in a cephalad direction. The direction which medial arm 218 translates along may be perpendicular to a direction along frame 212 which first side assembly 214 and second side assembly 216 translate along.

Medial arm 218 includes frame 220. Frame 220 includes teeth 236 along at least a portion of frame 220. Frame 220 includes a slot 234 configured to facilitate extension and retraction of medial arm 218. Medial arm 218 includes a body 232. Body 232 may be attached (e.g., welded, removably attached with fasteners, etc.) to frame 212.

Body 232 is configured to remain fixed relative to frame 212. Frame 220 is configured to actuate (e.g., translate in a first and second direction) relative to body 232. Body 232 includes an aperture (e.g., a bore, a hole, a slot, etc.), shown as aperture 252, configured to receive frame 220 therewithin. Frame 220 may translate within aperture 252 of body 232 to selectably extend and retract medial arm 218.

Medial arm 218 includes a ratcheting mechanism 238 configured to maintain a current position of frame 220 relative to body 232 or to restrict translation of frame 220 relative to body 232 in one direction (e.g., an extension direction or a retraction direction). Ratcheting mechanism 238 may be a releasable ratcheting mechanism such that a user can release ratcheting mechanism 238 to enable translation of frame 220 relative to body 232 in both directions (e.g., in both an extension direction and a retraction direction). When in a locked configuration, ratcheting mechanism 238 restricts the translation of frame 220 relative to body 232 in at least one direction. When in an unlocked position, ratcheting mechanism 238 allows translation of frame 220 relative to body 232. When in a locked position, ratcheting mechanism 238 may be configured to allow translation of frame 220 relative to body 232 in a first direction (e.g., an extension direction) and restrict translation of frame 220 relative to body 232 in an opposite direction (e.g., a retraction direction). Ratcheting mechanism 238 may include one or more components configured to interface with teeth 236 of frame 220 to selectably lock or restrict translation of frame 220 relative to body 232.

Medial arm 218 includes an end portion 240. End portion 240 may be integrally formed with frame 220. In other embodiments, end portion 240 is fixedly connected to frame 220 at an end of frame 220. End portion 240 is configured to facilitate rotation of medial blade assembly 250 about axis 254 in either direction 256 or a direction opposite direction 256. End portion 240 is rotatably coupled with receiver portion 248 via pin 244. Receiver portion 248 is configured to rotate about pin 244 to retract tissue or to angulate medial blade assembly 250. Receiver portion 248 and end portion 240 are configured to rotate relative to each other about axis 254 extending substantially through pin 244. Since end portion 240 is fixedly coupled (e.g., removably, integrally formed, welded, etc.) to frame 220, rotation of receiver portion 248 about pin 244 is also rotation relative to frame 220. End portion 240 and receiver portion 248 are hingedly interfaced at pin 244. In some embodiments, pin 244 is a hinge element (e.g., a piano hinge, a barrel hinge, a butterfly hinge, etc.) configured to facilitate rotation (e.g., hinged rotation) of receiver portion 248 relative to end portion 240. In other embodiments, pin 244 is a component of a hinged interface between receiver portion 248 and end portion 240. In other embodiments, the hinged interface between receiver portion 248 and end portion 240 is a spring hinge configured to return receiver portion 248 to a predetermined rotational position relative to end portion 240. Pin 244 is configured to extend through corresponding apertures (e.g., co-linear apertures) of end portion 240 and receiver portion 248 to facilitate rotation of receiver portion 248 about axis 254.

In an exemplary embodiment, receiver portion 248 is configured to rotate (e.g., hingedly rotate) relative to end portion 240 in response to an actuation of rotational control member 242. Rotational control member 242 may be a threaded bolt configured to cause receiver portion 248 to rotate in direction 256 about axis 254 in response to rotational control member 242 being rotated in a first direction (e.g., a clockwise direction) and to cause receiver portion 248 to rotate in a direction opposite direction 256 about axis 254 in response to rotational control member 242 being rotated in a second direction (e.g., a counter-clockwise direction). In this way, a user may adjust rotational control member 242 to rotate (e.g., hingedly pivot) receiver portion 248 with respect to end portion 240 about axis 254 to angulate medial blade assembly 250. Likewise, the user may adjust rotational control member 242 to pivot receiver portion 248 about axis 254 in a direction opposite direction 256.

End portion 240 may include a track (e.g., an aperture, a recess, a groove, a slot, a channel, etc.), shown as channel or track 265. Channel/track 265 extends along an exterior surface of end portion 240 and is configured to interface with a portion of rotational control member 242 to facilitate hinged rotation of receiver portion 248 relative to end portion 240. In an exemplary embodiment, channel/track 265 is configured to slidably interface with a portion of rotational control member 242 to facilitate hinged rotation of receiver portion 248 relative to end portion 240.

Receiver portion 248 is configured to interface (e.g., removably, fixedly, rotationally, etc.) with medial blade assembly 250, according to an exemplary embodiment. Receiver portion 248 and medial blade assembly 250 are configured to rotatably interface at rotational interface 262. Rotational interface 262 may be a ball and socket interface configured to facilitate rotation about axis 258, as described hereinbelow. Rotational interface 262 includes a receiving portion (e.g., a receiving aperture, a receiving socket, a female receiving portion, etc.), shown as socket 264. Socket 264 is defined by receiver portion 248 and is configured to rotatably interface with a corresponding interfacing member of medial arm 218, shown as ball 260. Ball 260 is configured to correspondingly interface with socket 264 to facilitate rotation of ball 260 about axis 258. Axis 258 may be perpendicular to axis 254 and extend generally outwards from a center of receiver portion 248. Receiver portion 248 includes a locking member, shown as set screw 246. Set screw 246 is configured to lock medial blade assembly 250 at a current angular position about axis 258 relative to receiver portion 248. For example, a user may loosen (e.g., turn counter clockwise) set screw 246 until medial blade assembly 250 can rotate freely about axis 258 via rotational interface 262. The user may then rotate medial blade assembly 250 to a desired angular position of axis 258 and then lock the present angular position by tightening (e.g., turning clockwise) set screw 246. Set screw 246 is configured to interface with a cup or pin 274 (see FIG. 34) to lock the angular position of medial blade assembly 250 relative to receiver portion 248 about axis 258.

Medial blade assembly 250 includes a blade 352 and a body 354, according to an exemplary embodiment. Blade 352 is configured to translate relative to body 354 to extend or retract. Blade 352 is configured to interface with a track, channel, groove, etc., of body 354 to selectably translate relative to body 354. In an exemplary embodiment, blade 352 is configured to receive blade extension adjuster 251. Blade extension adjuster 251 is configured to transition blade 352 between an extension or adjustment configuration and a locked or fixed configuration. When blade 352 is in the extension configuration, blade 352 can translate (e.g., extend) relative to body 354. When blade 352 is in the locked configuration, blade 352 is prevented from translating along body 354. Blade extension adjuster 251 may include a handle or grasping portion 410. Grasping portion 410 facilitates easy use of blade extension adjuster 251 for any of the purposes described herein with reference to blade extension adjuster 251.

Figure 34:
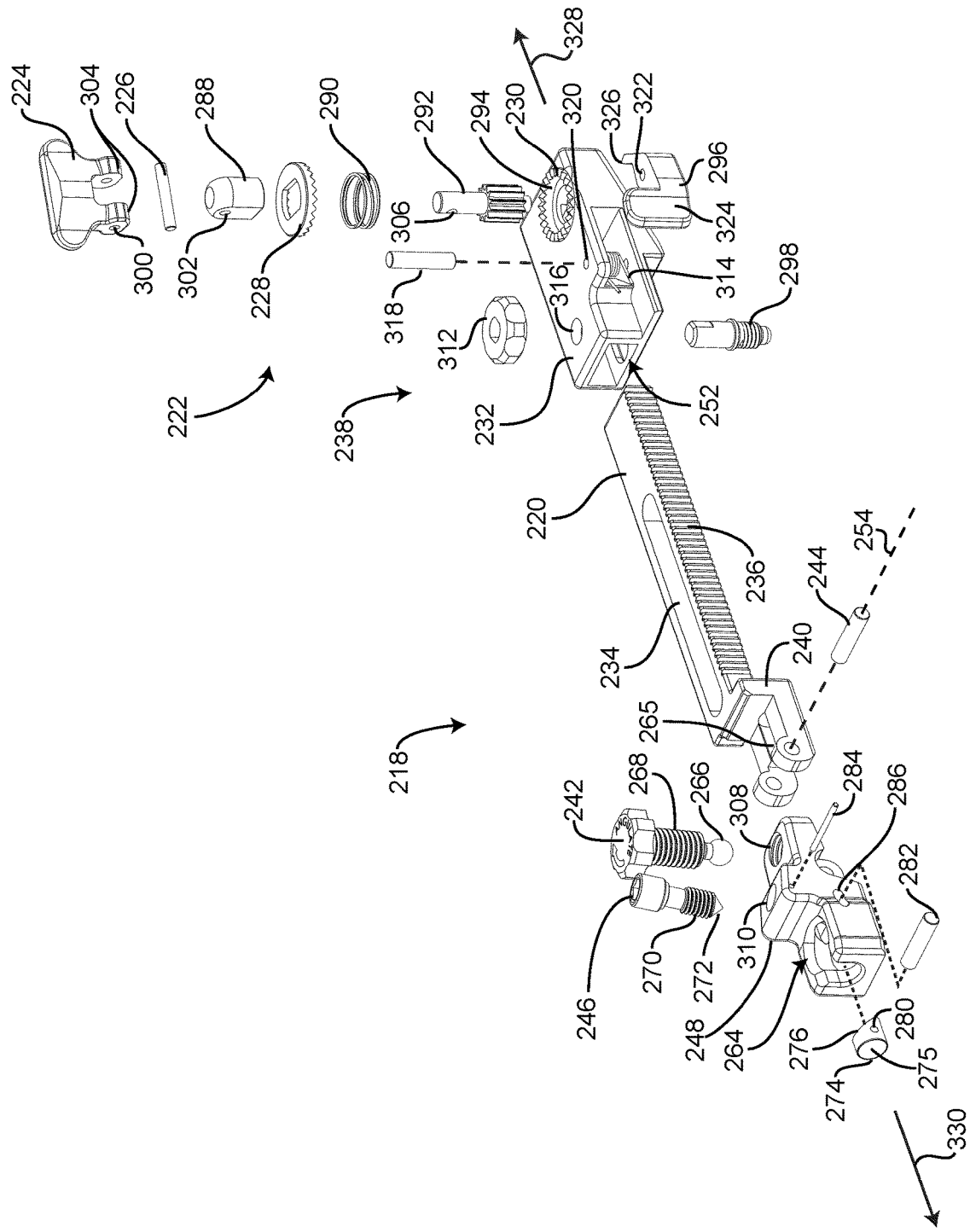
FIG. 34 is an exploded view of the medial arm of the spinal retractor of FIGS. 26-27, according to one embodiment.

Referring now to FIG. 34, medial arm 218 is shown in an exploded view. Medial arm 218 includes body 232 having aperture 252 configured to receive frame 220. Frame 220 is configured to translate within aperture 252 to adjust an overall length of medial arm 218 (e.g., to extend or retract). Body 232 includes selectable locking mechanism 222, shown in an exploded view. Locking mechanism 222 is configured to selectably lock translation of frame 220 with respect to body 232 at a current location (e.g., at a current amount of extension of medial arm 218 or a current amount of retraction of medial arm 218). Locking mechanism 222 includes a handle, shown as locking lever 224, a pin 226, a receiver 288, a toothed disc 228, a compression spring 290, and a toothed shaft 292. Locking lever 224 includes a pair of tabs 304 and an aperture (e.g., a bore, a hole, etc.), shown as aperture 300 extending therein. Aperture 300 extends through both tabs 304.

Aperture 300 is configured to receive pin 226 therewithin. Receiver 288 includes an aperture 302 configured to receive pin 226 therewithin. When assembled, aperture 302 and aperture 300 may be substantially collinear such that pin 226 extends through both aperture 302 and apertures 300 to pivotally couple locking lever 224 to receiver 288. Receiver 288 is configured to be positioned between tabs 304 such that the space defined between tabs 304 receives receiver 288 therewithin and positions aperture 302 of receiver 288 coaxially with aperture 300 of locking lever 224. Receiver 288 may be hollow having an inner volume configured to receive at least a portion of an upper end of toothed shaft 292. Toothed shaft 292 includes an aperture (e.g., a bore, a hole, etc.), shown as aperture 306. Toothed shaft 292 is configured to be received within the hollow portion of receiver 288 such that aperture 306 of toothed shaft 292 is coaxial with aperture 302 of receiver 288, as well as being coaxial with apertures 300 of locking lever 224. Pin 226 is configured to extend through aperture 300 of locking lever 224, aperture 302 of receiver 288, and aperture 306 of toothed shaft 292, when locking mechanism 222 is assembled.

Toothed disc 228 includes a central aperture defined therewithin configured to receive receiver 288. For example, the aperture of toothed disc 228 may substantially match or be slightly greater than a maximum outer perimeter of receiver 288 or a perimeter of receiver 288 at a corresponding location along a height of receiver 288. Compression spring 290 is configured to be assembled between toothed shaft 292 and toothed disc 228. Compression spring 290 is configured to provide an expansive force when locking mechanism 222 is transitioned into a locked state. When locking mechanism 222 is put in the locked state, the compressive force may prevent locking mechanism 222 from accidentally transitioning out of the locked state.

Toothed disc 228 is configured to interface with corresponding teeth 230 of body 232. Body 232 includes an aperture 294 configured to receive toothed shaft 292 therewithin. Aperture 294 is surrounded along its perimeter by teeth 230. Toothed shaft 292 is configured to interface with teeth 236 of frame 220, such that as frame 220 translates within aperture 252 of body 232, toothed shaft 292 is driven to rotate. Likewise, toothed shaft 292 may be driven to rotate to drive frame 200 to translate therewithin aperture 252 of body 232 (e.g., to extend or retract medial arm 218).

Figure 35:
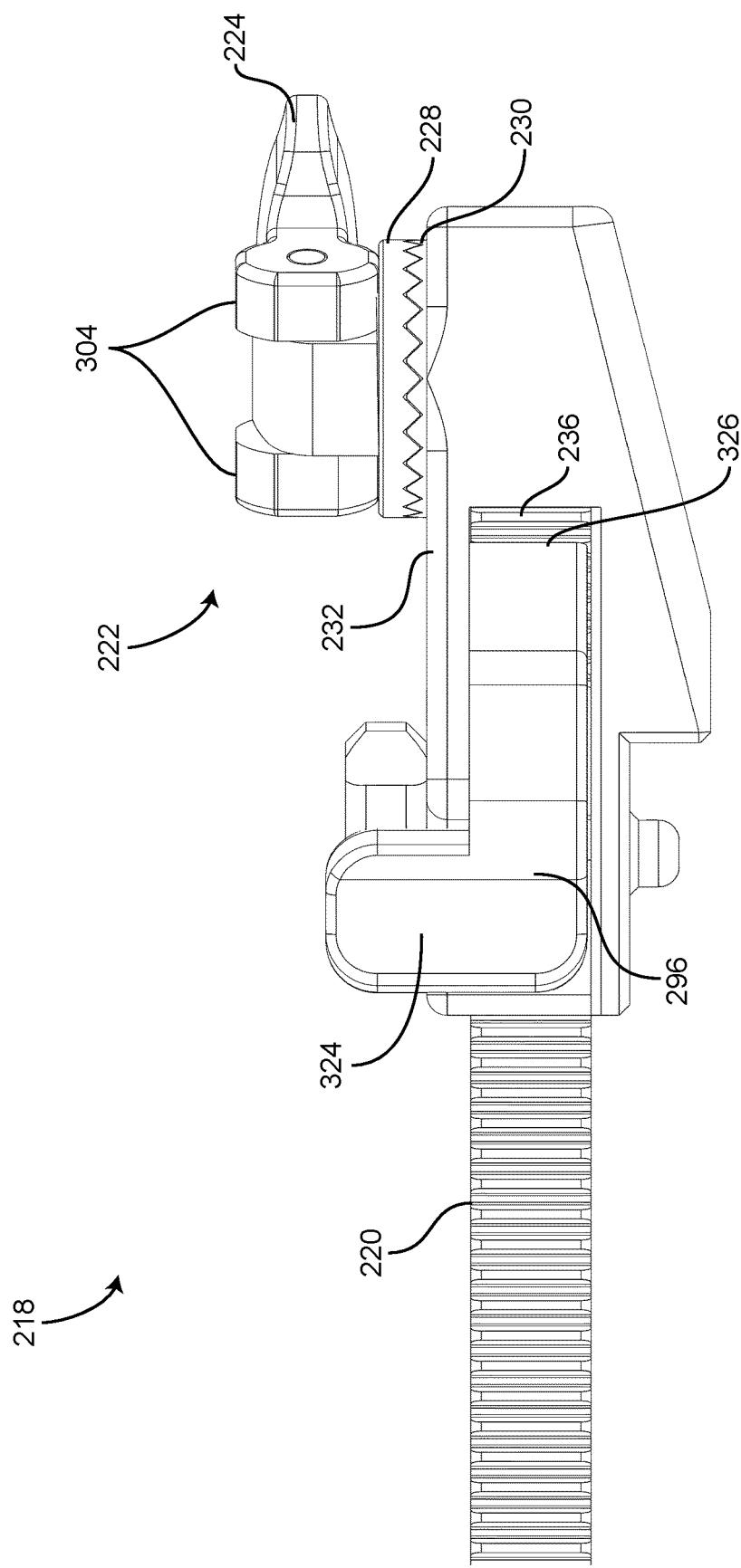
FIG. 35 is a side view of a locking mechanism of the medial arm of FIG. 34 in a locked configuration, according to one embodiment.
Figure 36:
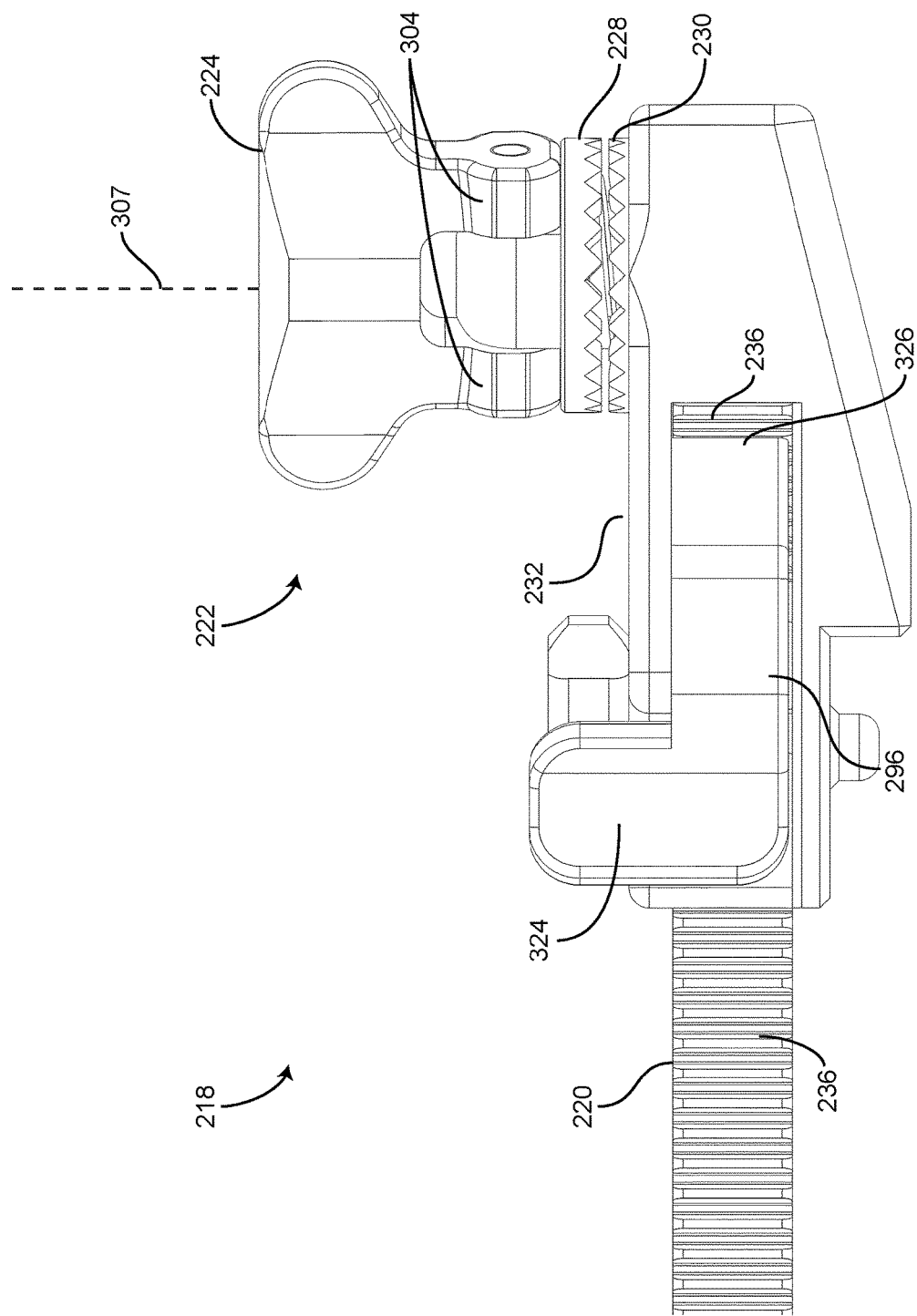
FIG. 36 is a side view of a locking mechanism of the medial arm of FIG. 34 in an unlocked configuration, according to one embodiment.

When locking mechanism 222 is transitioned into a locked position (e.g., by rotating locking lever 224), tabs 304 act as cams to bias toothed disc 228 to interface with teeth 230 of body 232, as shown in FIG. 35. FIG. 35 shows locking mechanism 222 in a locked position with locking lever 224 rotated such that tabs 304 bias toothed disc 228 to interface with teeth 230 of body 232. When locking mechanism 222 is in the locked position as shown in FIG. 35, frame 220 is prevented from translating within aperture 252 of body 232 by the interface between toothed disc 228 and teeth 230 of body 232. However, when locking lever 224 is rotated to the configuration shown in FIG. 36, locking mechanism 222 is transitioned into an unlocked position. When locking mechanism 222 is transitioned into the unlocked position, the interface between toothed disc 228 and teeth 230 of body 232 is removed. When the interface between toothed disc 228 and teeth 230 of body 232 is no longer present, frame 220 can translate within aperture 252 of body 232. Additionally, when locking mechanism 222 is in the unlocked position as shown in FIG. 36, locking lever 224 can be rotated about axis 307 to translate frame 220 relative to body 232. Since there is a toothed (e.g., gear) interface between toothed shaft 292 and teeth 236 of frame 220, rotation of locking lever 224 results in translation of frame 220 within aperture 252 of body 232.

Referring again to FIG. 34, rotational control member 242 is shown to include a threaded portion 268 and a ball portion 266. Ball portion 266 is configured to translate along track 265 of end portion 240 of frame 220. Ball portion 266 translates along track 265 of end portion 240 of frame 220 in response to rotation of rotational control member 242. Rotational control member 242 is configured to threadingly interface with threaded aperture 308 of receiver portion 248 via threaded portion 268. As rotational control member 242 is rotated, rotational control member 242 drives receiver portion 248 to pivot about axis 254 relative to end portion 240 via the threaded interface between threaded portion 268 and threaded aperture 308. As rotational control member 242 is rotated, ball portion 266 translates along track 265 of end portion 240.

Figure 29:
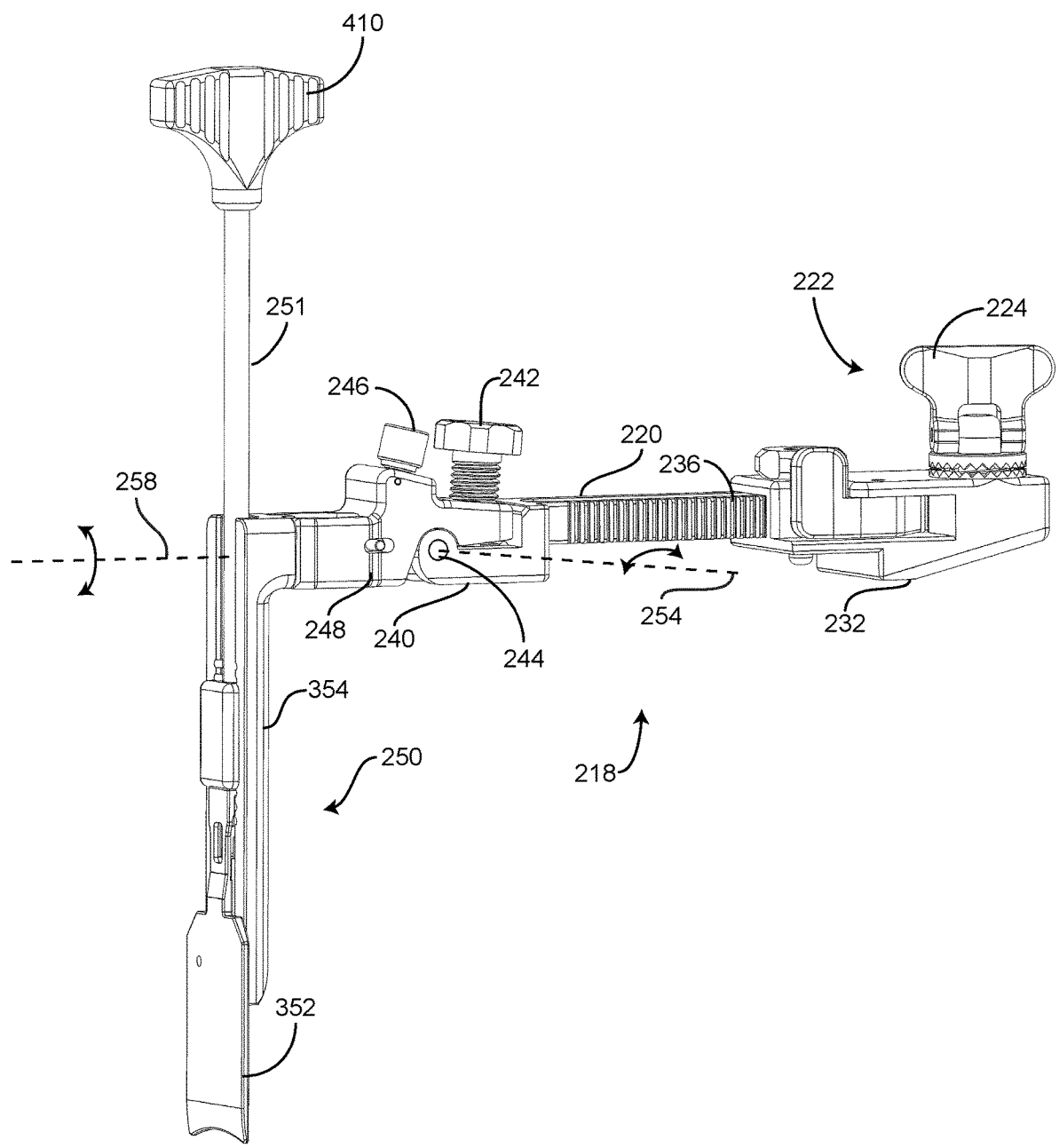
Figure 30:
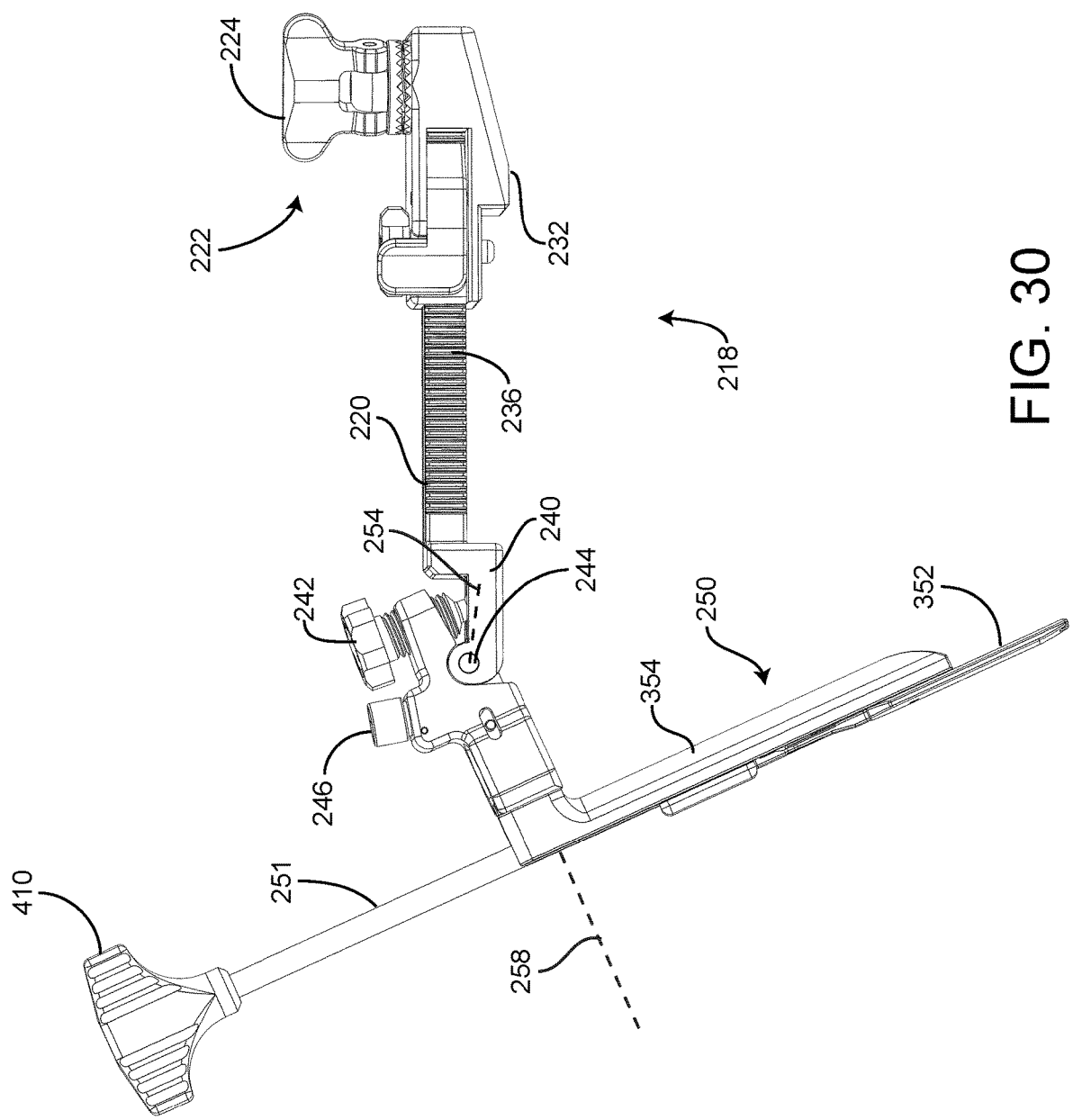

Referring now to FIGS. 29 and 30, the operation of rotational control member 242 is shown. FIGS. 29 and 30 shows medial arm 218 before and after rotational control member 242 has been rotated. After rotational control member 242 has been adjusted (e.g., rotated in a clockwise direction a certain number of revolutions), medial blade assembly 250 has been rotated about axis 254 relative to end portion 240 of frame 200. By adjusting rotational control member 242, medial blade assembly 250 can be reconfigured to various angular positions about axis 254. Advantageously, this provides an additional degree of freedom of medial blade assembly 250 which can be used to increase accuracy and adjustability of medial arm 218.

Referring again to FIG. 34, set screw 246 is shown including a threaded portion 270 and a conical end 272. Set screw 246 is configured to threadingly interface with aperture 310 of receiver portion 248 via threaded portion 270. Set screw 246 is configured to interface with pin (also referred to as cup) 274 to lock rotation of medial blade assembly 250 about axis 258. Conical end 272 of set screw 246 is configured to interface with a corresponding flat-shaped surface 276 of pin 274. For example, if conical end 272 of set screw 246 is angled at 45 degrees, surface 276 of pin 274 is likewise angled at 45 degrees. Pin 274 is configured to translate within an aperture of receiver portion 248. When pin 274 is driven by set screw 246 into contact with ball 260, medial blade assembly 250 is restricted from rotating about axis 258. Likewise, when pin 274 is driven out of contact with ball 260, medial blade assembly 250 can freely rotate about axis 258. Set screw 246 can include a hex-shaped portion configured to interface with a hex bit for adjustment of set screw 246. Pin 274 includes aperture 280 extending therethrough. Aperture 280 is configured to interface with pin 282. Pin 282 is configured to extend through and translate within slot 286 to facilitate translation of pin 274 therein. Receiver portion 248 includes an aperture configured to receive pin 284 therewithin to prevent set screw 246 from being completely removed from aperture 310.

In an exemplary embodiment, surface 275 of pin 274 is configured to interface with ball 260 of medial blade assembly 250. For example, surface 275 may have a profile matching a surface of ball 260. Ball 260 may include a flat portion configured to interface with surface 275. In other embodiments, surface 275 of pin 274 is curved to match an exterior surface of ball 260. When surface 275 is driven into contact with a corresponding surface of ball 260, medial blade assembly 250 is restricted from rotation about axis 258. Advantageously, this facilitates preventing medial blade assembly 250 from rotating about axis 258. A user can loosen set screw 246 such that surface 275 of pin 274 is not in contact with (or slidably contacts) the corresponding surface of ball 260, adjust the orientation of medial blade assembly 250 about axis 258, and then lock the angular position of medial blade assembly 250 about axis 258 by tightening set screw 246 such that surface 275 of pin 274 is in locking contact with ball 260.

Figure 31:
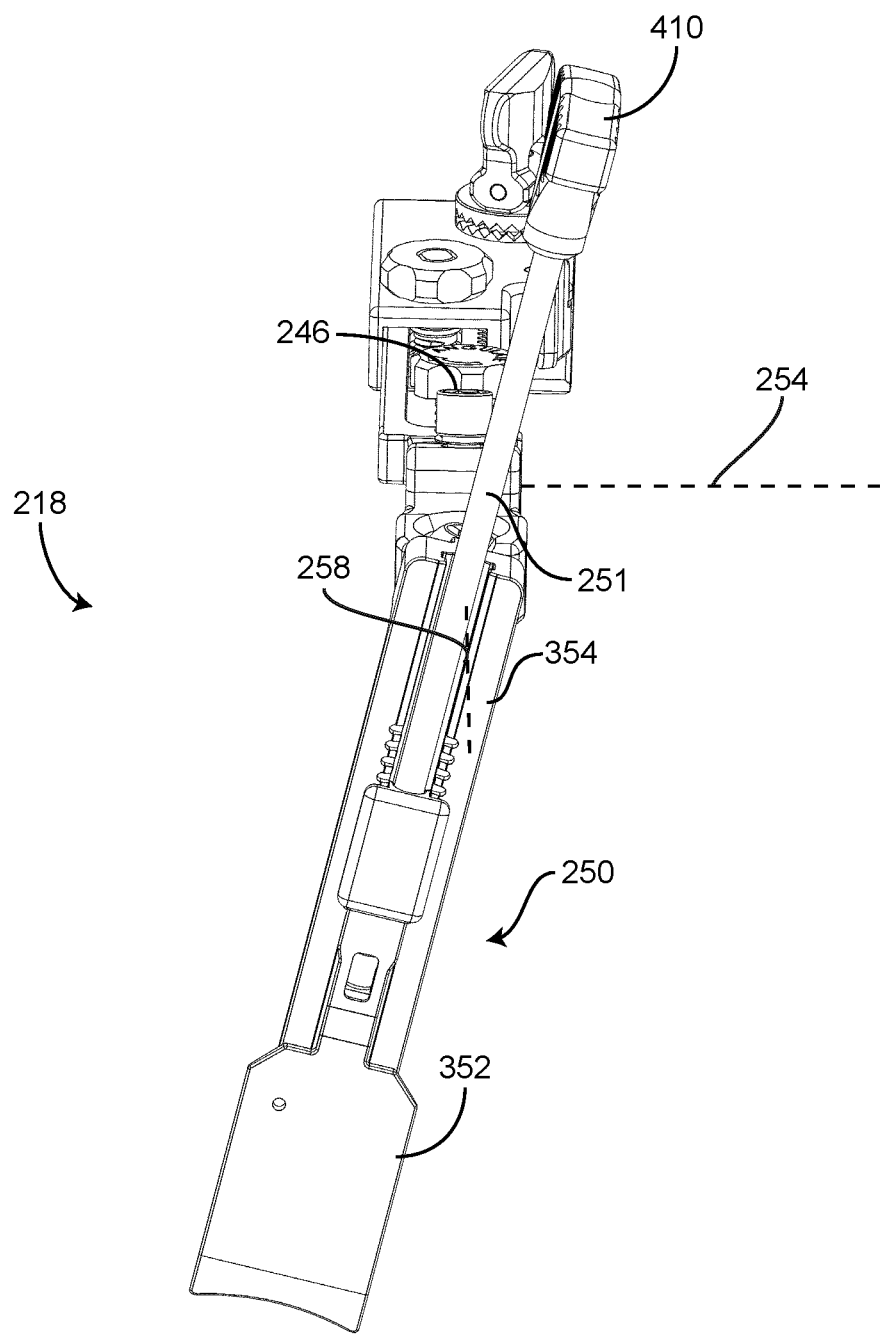
Figure 32:
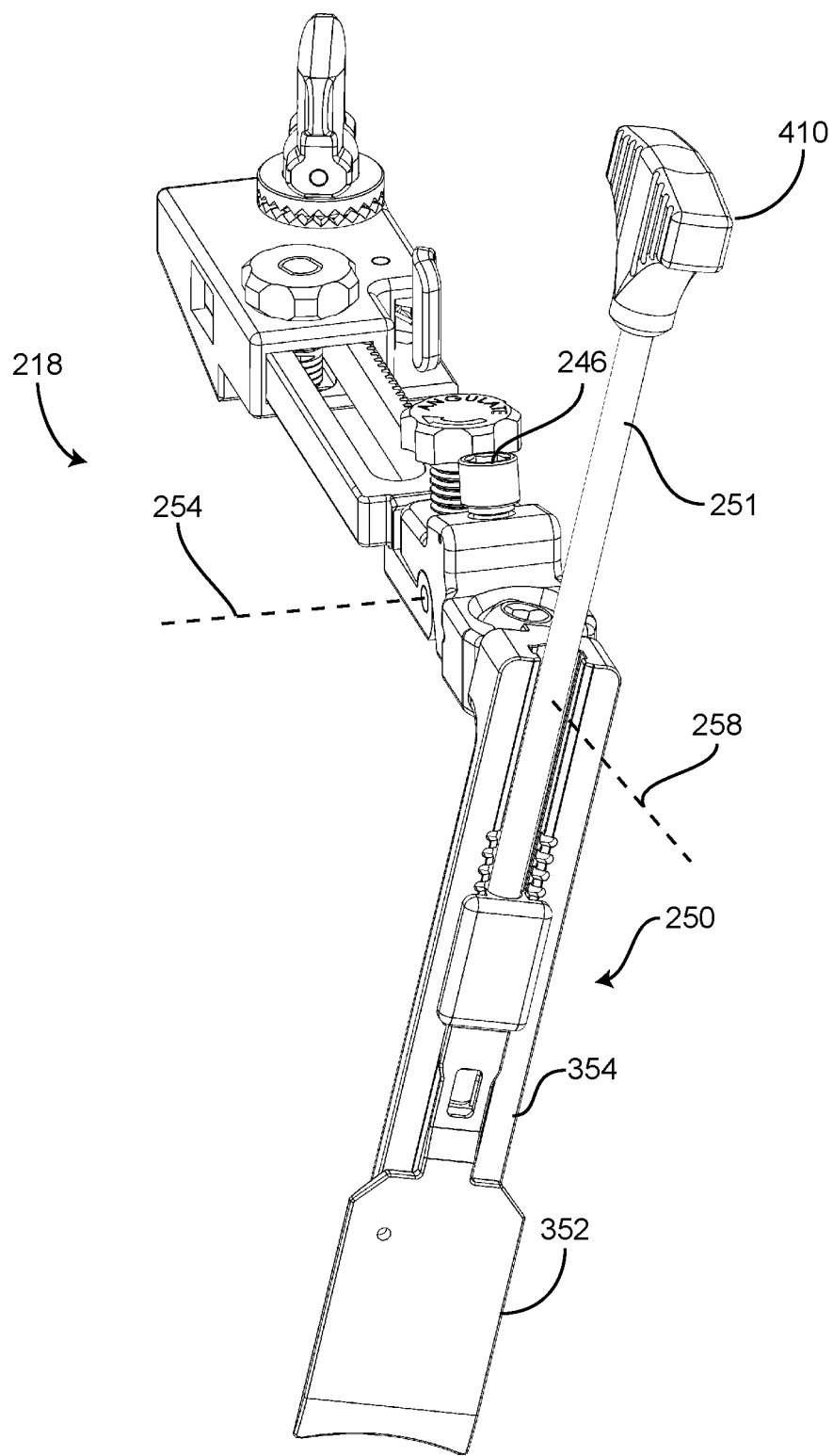
Figure 33:
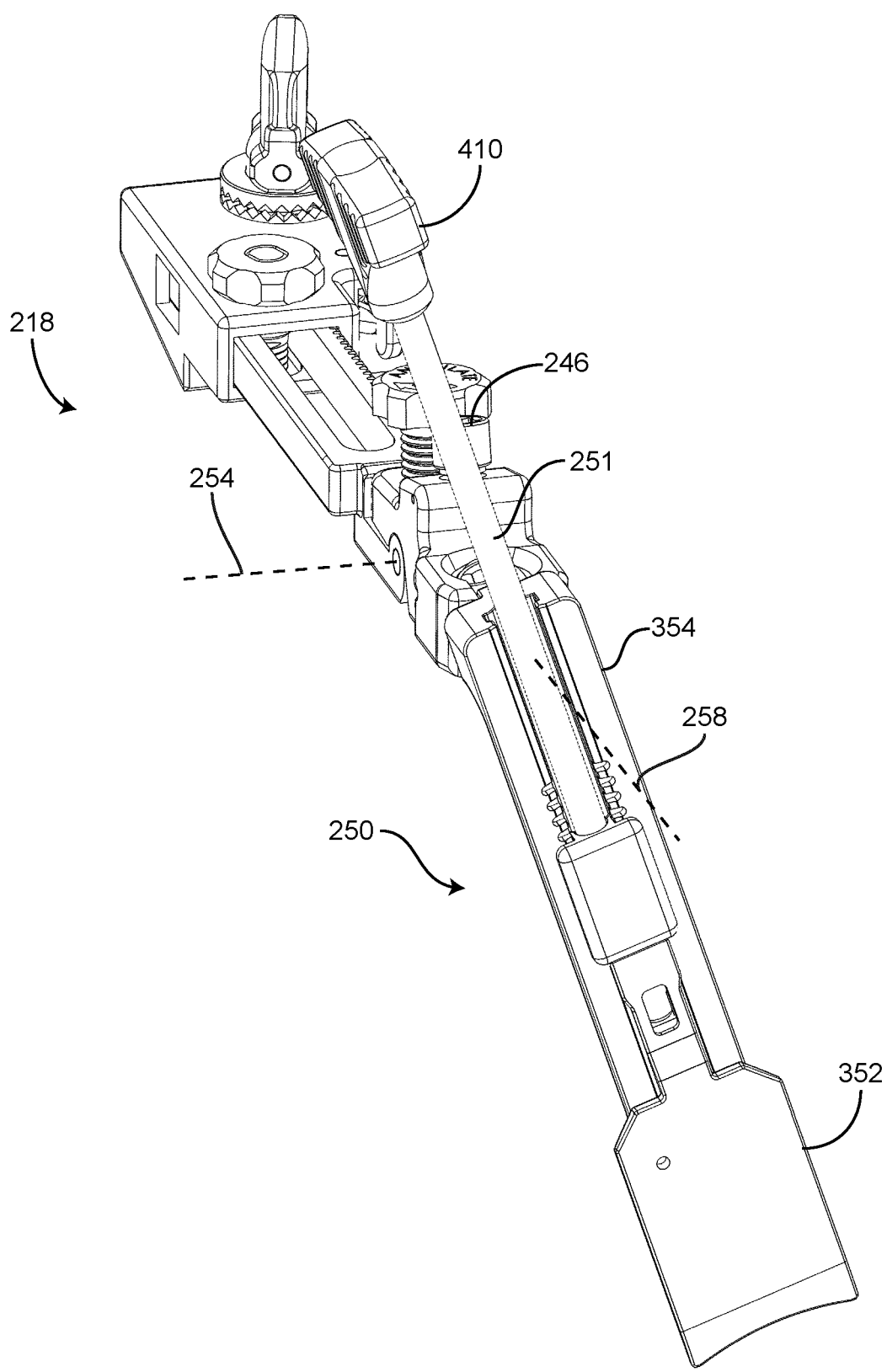

Referring now to FIGS. 31-33, medial arm 218 is shown in various configurations. FIG. 31 shows medial arm 218 with medial blade assembly 250 at a first angular orientation about axis 258. FIG. 32 shows medial blade assembly 250 at a second angular orientation about axis 258. FIG. 33 shows medial blade assembly 250 at a third angular orientation about axis 258. In order to rotate medial blade assembly 250 from the angular position as shown in FIG. 31 to the angular position as shown in FIG. 32 and/or FIG. 33, set screw 246 must first be adjusted (e.g., turned counter clockwise, loosened, etc.) such that surface 275 of pin 274 is not in contact with (or slidably engages) the corresponding surface of ball 260. After set screw 246 has been adjusted, medial blade assembly 250 can be freely rotated from the angular orientation as shown in FIG. 31 to the angular orientation shown in FIG. 32 and/or the angular orientation as shown in FIG. 33. Once medial blade assembly 250 is rotated about axis 258 such that medial blade assembly 250 is in a desired angular orientation, set screw 246 can be adjusted (e.g., turned clockwise, tightened, etc.) such that surface 275 of pin 274 is in locking contact with the corresponding surface of ball 260.

Referring again to FIGS. 34-35, medial arm 218 includes ratcheting mechanism 238. In one embodiment, ratcheting mechanism 238 is configured to restrict translation of frame 220 in one direction but allow translation of frame 220 in an opposite direction. Ratcheting mechanism 238 includes spring 314, pin 318, and a ratcheting member shown as pawl 296. Pawl 296 is configured to interface with teeth 236 of frame 220 at first end 326. Pawl 296 is configured to pivot about pin 318. Pin 318 is configured to interface with aperture 320 of body 232 to provide a pivot point for pawl 296 to rotate about. Spring 314 is configured to interface with pawl 296 to bias pawl 296 to interface with teeth 235 of frame 220. Pawl 296 includes aperture 322 configured to interface with pin 318 to facilitate rotation of pawl 296 about pin 318 thereabout. Pawl 296 is configured to allow retraction of medial arm 218 (e.g., in direction 328) but restrict extension of medial arm 218 (e.g., in direction 330). Pawl 296 is configured to interface with teeth 236 of frame 220 at first end 326. First end 326 is configured to interface between adjacent teeth of teeth 236 to restrict translation of frame 220 in one direction. Pawl 296 may be selectively disengaged from interfacing with teeth 236 of frame 220 by applying a force (e.g., a user may apply a force) at second end 324. Second end 324 may include a paddle configured to receive a force or a pressure from a user. When the user applies a force at second end 324, pawl 296 rotates about pin 318 and first end 326 is disengaged from teeth 236 of frame 220, thereby allowing translation of frame 220 in either direction. When pawl 296 is engaged with teeth 236 of frame 220 at first end 326, frame 220 can translate along direction 328 (e.g., a retraction direction) but is prevented from translating in direction 330 due to the interface of first end 326 and teeth 236 of frame 220. When frame 220 moves in direction 328, pawl 296 rotates about pin 318 and first end 326 is temporarily disengaged from teeth 236 of frame 220. After frame 220 has translated a certain amount in direction 328 (e.g., a width between adjacent teeth of teeth 236), pawl 296 is driven by spring 314 to interface with teeth 236 of frame 220 at first end 326.

Referring still to FIG. 34, medial arm 218 includes an attachment member 298. Attachment member 298 may be configured to couple with one or more attachment devices. In an exemplary embodiment, attachment member 298 includes a threaded portion. Attachment member 298 may be a generally cylindrical component, configured to interface with aperture 316 of body 232. Aperture 316 extends through substantially an entire thickness of body 232. Attachment member 298 may slidably interface with aperture 316 such that attachment member 298 can rotate relative to body 232. Attachment member 298 is configured to interface with adjustment member 312. Adjustment member 312 may be a knob, a handle, etc., for rotating attachment member 298. Adjustment member 312 can include an aperture configured to interface with an upper end of attachment member 298. Attachment member 298 may have an outer diameter less than a width of slot 234 such that frame 220 can translate while attachment member 298 is disposed within slot 234. In some embodiments, attachment member 298 is fixedly coupled with adjustment member 312. Advantageously, additional devices, apparatuses, medical devices, retractor devices, extensions, etc., may be threadingly interfaced with the threaded portion of attachment member 298. Attachment member 298 may be rotated by adjustment member 312 to facilitate threadingly attaching the additional device to attachment member 298. For example, a user may position an additional component, device, extension, etc., at the threaded portion of attachment member 298 and rotate attachment member 298 by rotating adjustment member 312 to threadingly interface the attachment to attachment member 298. In some embodiments, attachment member 298 is configured to releasably couple (e.g., secure) medial arm 218 with frame 212.

Figure 37:
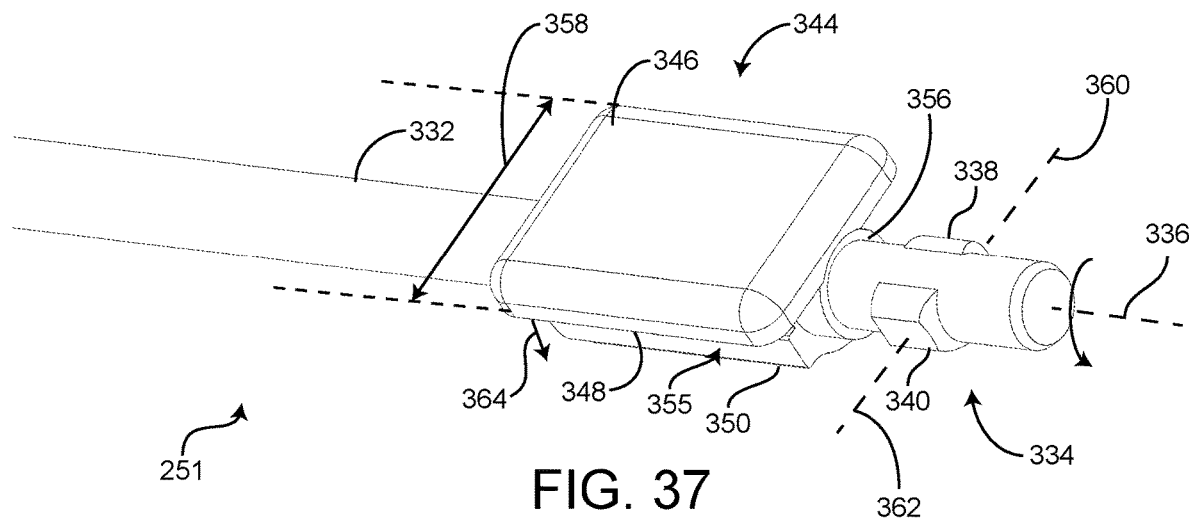
FIGS. 37-38 are perspective views of an end of a blade extension adjuster which may be used to adjust an extension of a medial blade of the spinal retractor of FIGS. 26-27, according to one embodiment.
Figure 38:
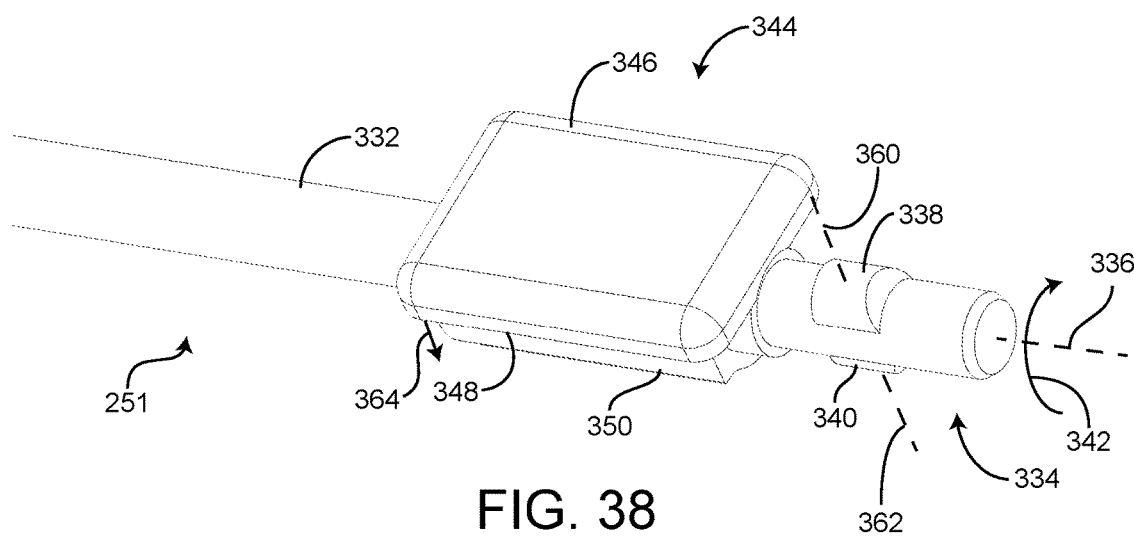

Referring now to FIGS. 37-38, blade extension adjuster 251 is shown in greater detail, according to an exemplary embodiment. Blade extension adjuster 251 is configured to facilitate adjusting an overall length (e.g., an extension, a retraction) of medial blade assembly 250. Blade extension adjuster 251 is configured to be inserted into or interfaced with blade 352. Blade extension adjuster 251 may transition between a locked configuration as shown in FIG. 37 and an extension configuration as shown in FIG. 38. When blade extension adjuster 251 is interfaced with blade 352 in the locked configuration as shown in FIG. 37, blade extension adjuster 251 can be used to rotate medial blade assembly 250 about axis 258 and/or axis 254. When blade extension adjuster 251 is in the extension configuration as shown in FIG. 38, blade extension adjuster 251 can be used to adjust an extension of blade 352 (e.g., to translate blade 352 relative to body 354). When blade extension adjuster 251 is in the extension configuration it can still be used to adjust an orientation of medial blade assembly 250 by rotating medial blade assembly 250 about axis 258 and/or axis 254. Blade extension adjuster 251 is rotated ninety degrees about axis 336 in direction 342 or a direction opposite direction 342 to transition between the extension configuration and the locked configuration as shown in FIGS. 37-38.

Referring still to FIGS. 37-38, blade extension adjuster 251 includes an elongated member 332, an interfacing portion 344, and an engagement portion 334. Elongated member 332 is shown as a generally cylindrical bar. However, elongated member 332 may have a square cross section, a hexagonal cross section, etc. Elongated member 332 has a length to facilitate easy insertion and adjustment of blade extension adjuster 251. The length of elongated member 332 may also facilitate rotation of medial blade assembly 250 about axis 258 and/or axis 254 by providing a longer moment arm (e.g., more leverage) for a user. Axis 336 extends through an entire longitudinal length of blade extension adjuster 251. Axis 336 is a centerline of blade extension adjuster 251 and may extend through a center of elongated member 332.

Blade extension adjuster 251 includes interfacing portion 344. Interfacing portion 344 is configured to interface with a slot, channel, recess, guide, etc., of body 354. Interfacing portion 344 may be configured to guide blade extension adjuster 251 into proper engagement with blade 352 at engagement portion 334. Interfacing portion 344 includes first guide member 346 and second guide member 350. First guide member 346 is generally rectangular and may have rounded edges on an outward side. First guide member 346 includes an inward side, surface, face, edge, etc., shown as inward facing surface 348. Inward facing surface 348 is at a side opposite the outward side of first guide member 346. Inward facing surface 348 is configured to slidably interface with a corresponding surface of body 354. In an exemplary embodiment, first guide member 346 is integrally formed with collar 356. Collar 356 may be rotatably coupled to elongated member 332 but prevented from translating along a length of elongated member 332. First guide member 346 may be positioned at an outward edge of collar 356. First guide member 346 extends tangentially outwards from an outer edge of collar 356. First guide member 346 has an overall width 358. In an exemplary embodiment, overall width 358 is greater than a diameter of elongated member 332.

Interfacing portion 344 includes second guide member 350. Second guide member 350 is configured to slidably interface with a groove, channel, track, recess, etc., of body 354 to slidably engage blade extension adjuster 251 with body 354. In an exemplary embodiment, a centerline extending through second guide member 350 which is perpendicular to axis 336 is substantially parallel to a corresponding centerline which extends through first guide member 346 and is perpendicular to axis 336. First guide member 346 and second guide member 350 define a recess 355 therebetween. Recess 355 may be configured to interface with one or more tracks, protrusions, rails, etc., of body 354 to facilitate a slidable and translatable engagement between blade extension adjuster 251 and body 354.

Referring still to FIGS. 37-38, engagement portion 334 is shown to include first protrusion 338 and second protrusion 340, according to an exemplary embodiment. First protrusion 338 and second protrusion 340 extend radially outwards from an exterior surface of elongated member 332 at engagement portion 334. First protrusion 338 and second protrusion 340 are configured to interface with a spring portion or member of blade 352. When elongated member 332 is rotated ninety degrees or is transitioned between the adjustment configuration and the locked configuration, first protrusion 338 and second protrusion 340 are configured to interface with the spring to transition blade 352 between an adjustable configuration and a locked configuration, respectively. First protrusion 338 has a generally arcuate outermost surface, while second protrusion 340 has a generally flat outermost surface. First protrusion 338 and second protrusion 340 are disposed on opposite sides of elongated member 332. For example, an axis 360 which extends radially outwards from axis 336 through a center of first protrusion 338 is substantially collinear with an axis 362 which extends radially outwards from axis 336 through a center of second protrusion 340. Additionally, centerline/axis 360 and centerline/axis 362 are 180 degrees from each other, where the 180-degree angle is measured about axis 336. Blade extension adjuster 251 is configured to be inserted into blade 352 in the configuration as shown in FIG. 37. In the locked configuration as shown in FIG. 37, axes 362/360 are substantially perpendicular to direction 364 which extends normally outwards from inward facing surface 348. In the adjustment configuration as shown in FIG. 38, axes 360/362 are substantially parallel to direction 364.

Figure 39:
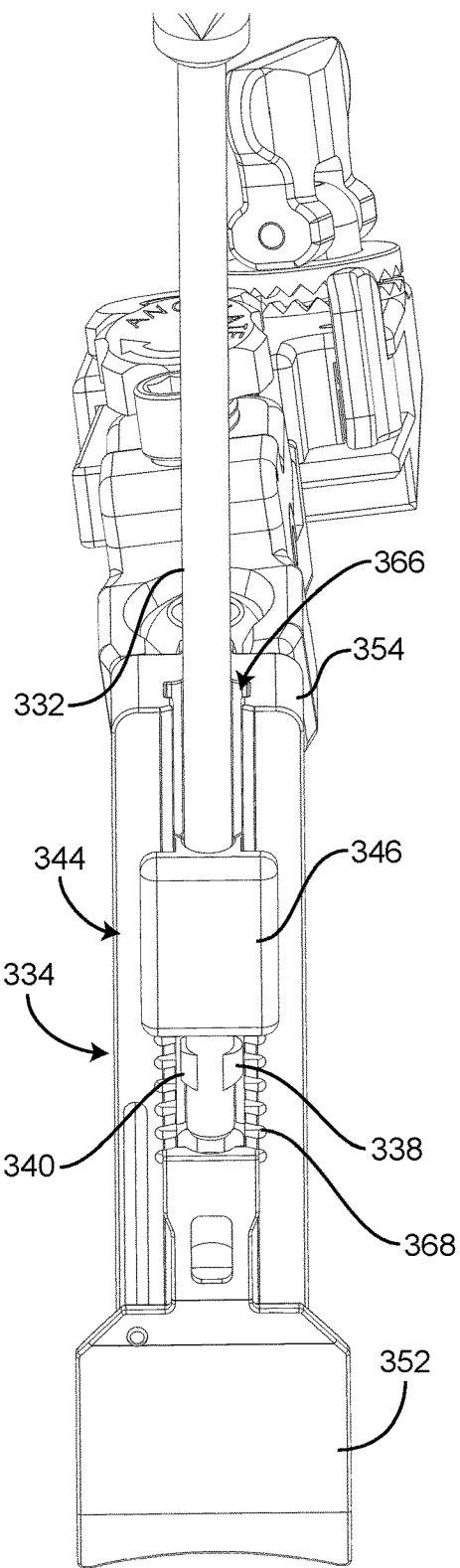
FIG. 39 is a perspective view of the blade extension adjuster of FIGS. 37-38 inserted into a medial arm of the spinal retractor of FIGS. 26-27, according to one embodiment.

Referring now to FIG. 39, blade extension adjuster 251 is shown being inserted into body 354, according to an exemplary embodiment. Blade extension adjuster 251 is configured to slidably interface with channel 366 of body 354. Blade extension adjuster 251 may slidably interface with channel 366 and be inserted a distance until engagement portion 334 of blade extension adjuster 251 interfaces with blade 352. Blade extension adjuster 251 can then be rotated ninety degrees to adjust an extension of blade 352. Blade 352 is configured to slidably interface with channel 366 of body 354. In an exemplary embodiment, blade 352 is configured to interlock with notches 368 of channel 366 at various degrees of extension of blade 352. When blade 352 is interlocked with one of notches 368, blade 352 cannot translate along channel 366 and is fixed. Blade 352 can transition between a locked configuration where blade 352 interfaces with one or more of notches 368 and is prevented from translating and an extension configuration where blade 352 can translate along channel 366. Blade extension adjuster 251 can be configured to transition blade 352 between the locked configuration and the extension configuration such that blade 352 can be extended or retracted. For example, if blade 352 is in a first locked position such that blade 352 interfaces with a first notch of notches 368, a user can transition blade 352 into the extension configuration by inserting blade extension adjuster 251 and rotating blade extension adjuster 251 ninety degrees. The user can then adjust an extension of blade 352 by translating blade 352. Once blade 352 is in a desired position (e.g., a desired amount of extension), the user can rotate blade extension adjuster 251 ninety degrees to transition blade 352 back into the locked configuration. When blade 352 returns to the locked configuration, blade 352 interfaces with a second notch of notches 368. The interface between blade 352 and the second notch prevents blade 352 from extending or retracting (e.g., translating along channel 366).

Figure 40:
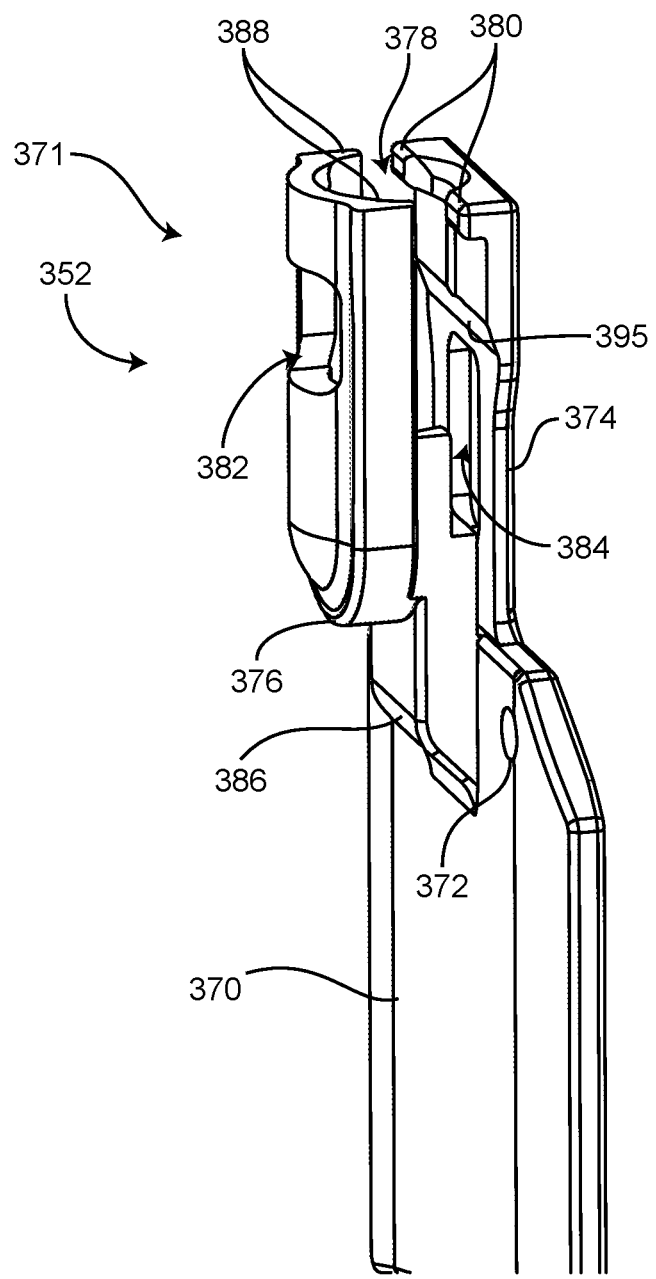
FIG. 40 is a perspective view of a blade of the medial arm of the spinal retractor of FIGS. 26-27, configured to receive the blade extension adjuster of FIGS. 37-38, according to one embodiment.
Figure 41:
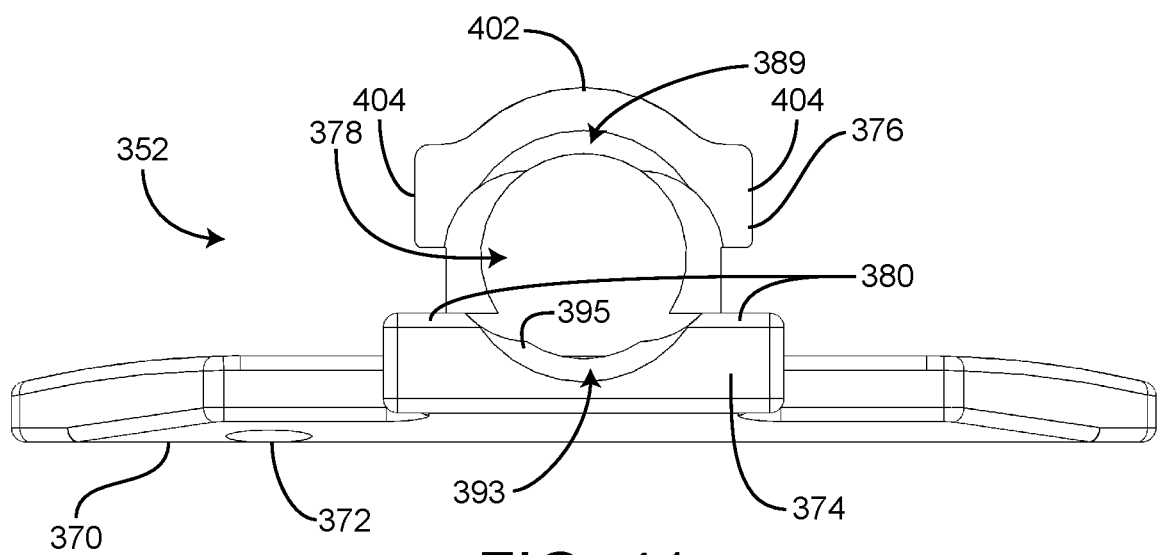
FIG. 41 is a top view of the blade of FIG. 40, according to one embodiment.

Referring now to FIGS. 40-41, blade 352 is shown in greater detail, according to an exemplary embodiment. Blade 352 includes a blade portion 370, and an interfacing portion 371. Blade portion 370 has a generally elongated shape with a relatively small thickness. The thickness of blade portion 370 may be uniform along an entire length of blade portion 370 or may vary along the length of blade portion 370. For example, the thickness may decrease along the length of blade portion 370. Blade portion 370 is configured to be inserted into an area which a user desires to expand. For example, blade portion 370 may be inserted into a surgical area and frame 220 may be retracted to expand the surgical area.

Blade portion 370 includes an aperture 372. Aperture 372 is configured to interface with a corresponding pin 390 (see FIG. 43). Pin 390 is configured to interface with a corresponding track, slot, recess, etc., shown as slot 392 of body 354. This restricts blade 352 such that blade 352 can only translate an entire length of slot 392. Additionally, pin 390 interfaced with slot 392 prevents blade 352 from rotating and facilitates translation-only movement of blade 352.

Interfacing portion 371 of blade 352 is configured to slidably and inter-lockingly interface with channel 366 of body 354. Interfacing portion 371 is also configured to receive blade extension adjuster 351 for adjusting an overall extension of blade 352. Interfacing portion 371 includes a first engagement member 376 and a second engagement member 374. First engagement member 376 is configured to slidably interface with channel 366 of body 354. For example, first engagement member 376 may include a rim, tab, extension, track, etc., shown as protrusions 388 which extend outwards along substantially an entire perimeter of first engagement member 176. Protrusions 388 may be configured to slidably interface with channel 366 of body 354 to slidably interface blade 352 with channel 366 such that blade 352 can translate along body 354. First engagement member 376 includes a window, opening, hole, aperture, etc., shown as aperture 382. First engagement member 376 may be connected to blade portion 370 via connector 386. Connector 386 may have an arcuate portion and a substantially straight portion. Connector 386 may be an elongated thin member (e.g., a panel, a plate, etc.) having uniform thickness along an entire length of connector 386. In an exemplary embodiment, blade portion 370, connector 386, first engagement member 376, and second engagement member 374 are all integrally formed to form blade 352. A cross-sectional shape of first engagement member 376 as shown in FIG. 41 may correspond to or be generally the same as a cross-sectional shape of channel 366 of body 354 such that first engagement member 376 can be received within channel 366.

Interfacing portion 371 of blade 352 includes second engagement member 374. Second engagement member 374 is substantially parallel to first engagement member 376. Second engagement member 374 includes tabs, protrusions, hooks, etc., shown as tabs 380 at an end of second engagement member 374. Second engagement member 374 is configured to ride (e.g., translate) along body 354 outside of channel 366. Tabs 380 of second engagement member 374 are configured to interface with notches 368 of body 354. When tabs 380 of second engagement member 374 interface with notches 368 of body 354, blade 352 is prevented from translating along body 354. Blade extension adjuster 251 is configured to selectably engage or disengage tabs 380 with notches 368 of body 354. When blade extension adjuster 251 is in the locked configuration, tabs 380 engage notches 368 to restrict translation of blade 352. When blade extension adjuster 251 is in the adjustment configuration, tabs 380 are driven to be disengaged from notches 368, thereby allowing blade 352 to be translated along channel 366/body 354.

Figure 42:
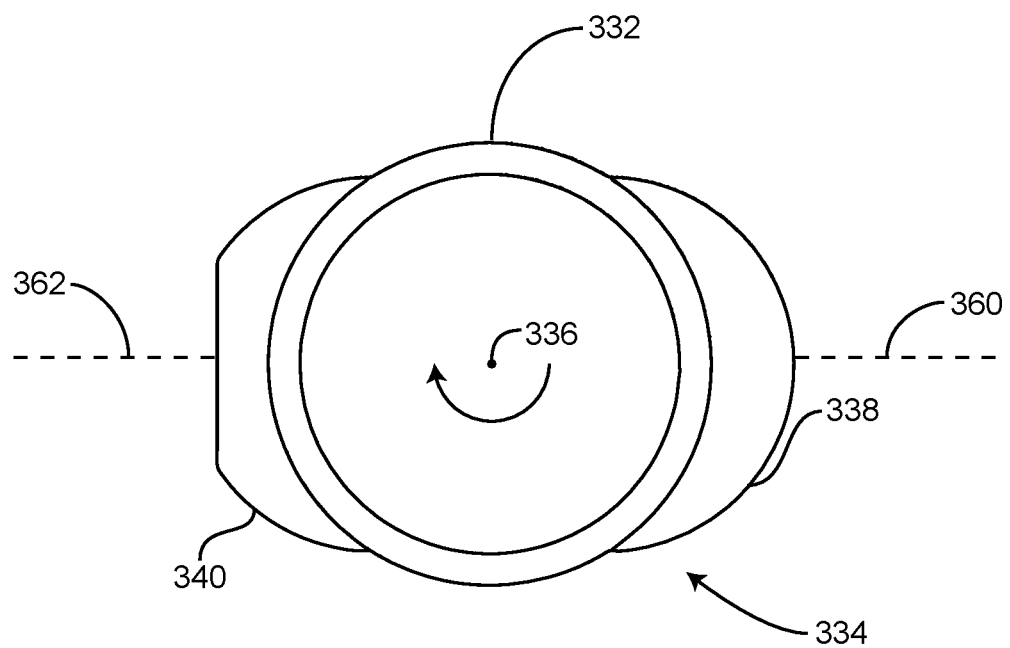
FIG. 42 is a bottom view of the end of the blade extension adjuster of FIGS. 37-38, according to one embodiment.

First engagement member 376 and second engagement member 374 define an opening, aperture, space, recess, etc., therebetween, shown as opening 378. Opening 378 is configured to receive blade extension adjuster 251 therewithin. Opening 378 may be defined by space between first engagement member 376 and second engagement member 374, as well as a cross-sectional shape of each of first engagement member 376 and second engagement member 374. For example, as shown in FIG. 41, first engagement member 376 and second engagement member 374 include aperture 389 and aperture 393, respectively. Aperture 389 and aperture 393 are each a portion of a circle (e.g., a semi-circle). As shown in FIG. 41, aperture 389 and aperture 393 define aperture 378, in addition to the void between first engagement member 376 and second engagement member 374. In an exemplary embodiment, the overall cross-sectional shape of aperture 378 corresponds (e.g., is the same as, is similar to, is similar to and slightly greater than) a cross-sectional shape of blade extension adjuster 251 at a maximum-cross sectional area of engagement portion 334. For example, a maximum cross-sectional area (e.g., a largest perimeter) of engagement portion 334 may be at axis 362 and/or axis 360. FIG. 42 shows the cross-section of engagement portion 334 at axis 362 and/or axis 360. The cross-sectional shape of engagement portion 334 of blade extension adjuster 251 is configured to correspond to aperture 378 such that at least a portion of blade extension adjuster 251 (e.g., at least engagement portion 334) can be inserted into aperture 378 of blade 352.

Engagement portion 334 is inserted into aperture 378 and rotated 90 degrees from the locked configuration to the extension configuration to disengage tabs 380 from notches 368 of body 354. When blade extension adjuster 251 is rotated 90 degrees, second protrusion 340 interfaces with aperture 382 of first engagement member 376. Second protrusion 340 may snap into, or fit into aperture 382 such that blade 352 translates along channel 366 with translation of blade extension adjuster 251. Aperture 382 may have a shape which corresponds to the cross-section of second protrusion 340 such that second protrusion 340 can interface with aperture 378. When second protrusion 340 is interfaced with aperture 378, blade extension adjuster 251 and blade 352 are translatably interlocked such that blade 352 can be adjusted (e.g., extended or retracted).

When blade extension adjuster 251 is rotated 90 degrees such that it is in the extension configuration, first protrusion 338 may function as a cam. First protrusion 338 may interface with second engagement member 374 and drive second engagement member 374 to deflect (e.g., bend). Second engagement member 374 functions as a spring which deflects or bends some amount due to being driven by first protrusion 338. When second engagement member 374 deflects, bends, deforms, etc., tabs 380 disengage notches 368, allowing blade 352 to translate along channel 366. First protrusion 338 may interface with a corresponding inner surface of second engagement member 374. For example, first protrusion 338 may interface with surface 395.

Figure 44B:
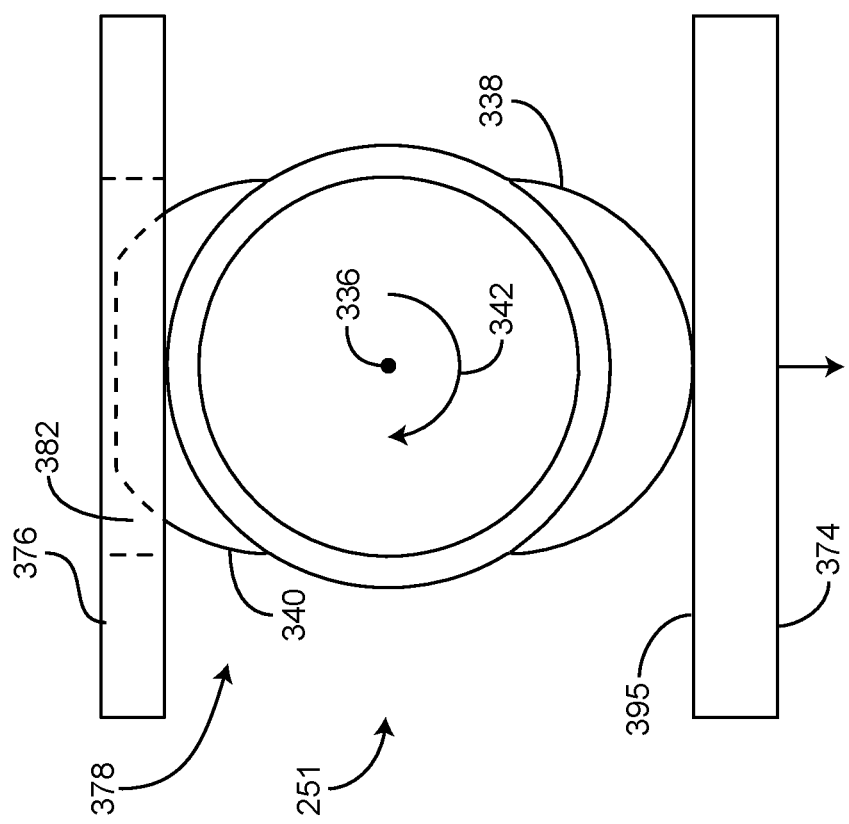
FIGS. 44A-B are drawings illustrating the function of the blade extension adjuster of FIGS. 37-38, according to one embodiment.
Figure 44A:
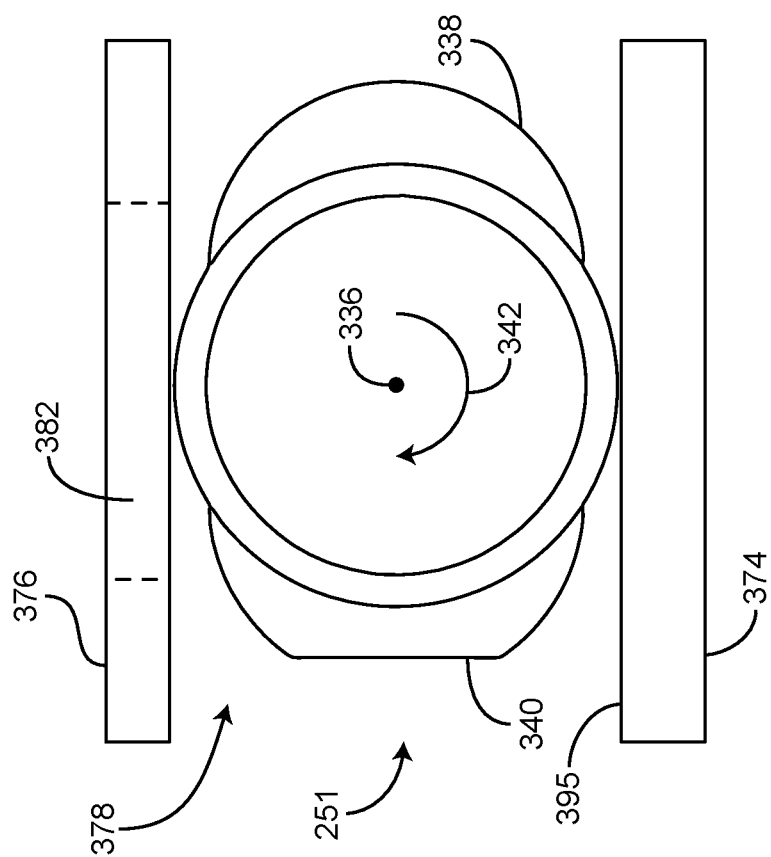
Figure 45:
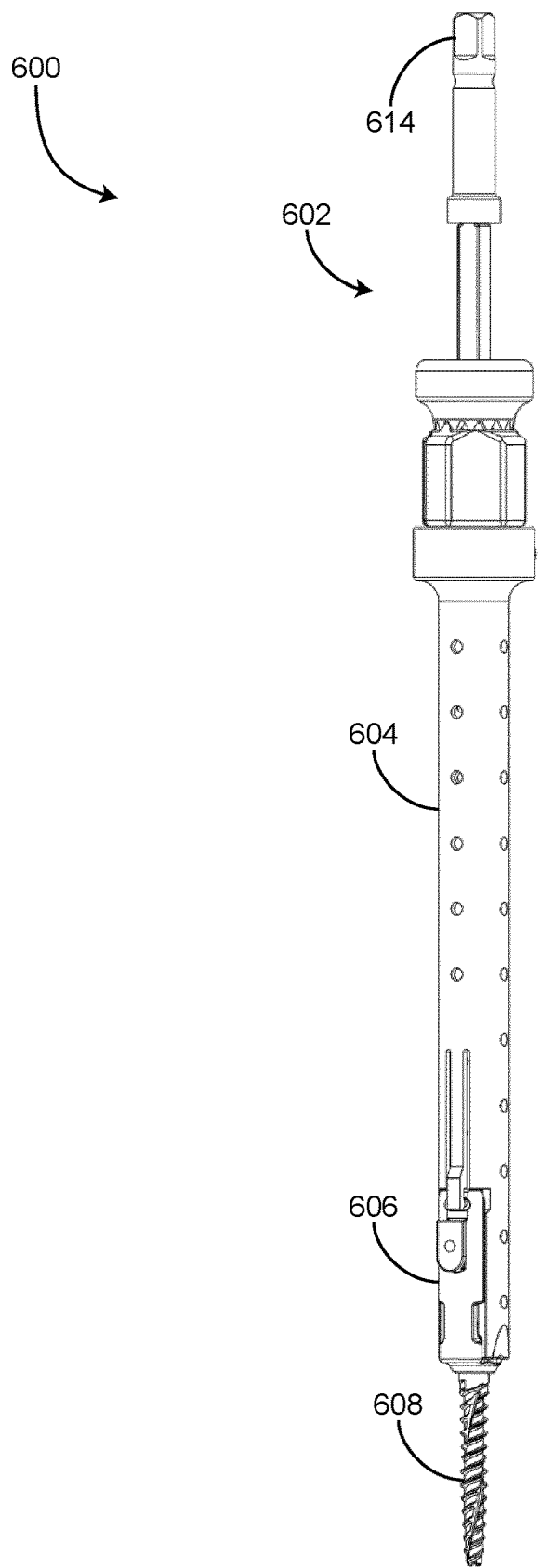
FIGS. 45-46 are side views of a tap and driver assembly, according to one embodiment.

Referring now to FIGS. 44A-B, blade extension adjuster 251 is shown in the locked configuration (FIG. 44A) and the extension configuration (FIG. 44B). It should be noted that the geometry of first engagement member 376 and second engagement member 374 is simplified as shown in FIGS. 44A-B. However, FIGS. 44A-B show the function of blade extension adjuster 251 and deflection/bending of second engagement member 374.

FIG. 44A shows blade extension adjuster 251 in the locked configuration. Blade extension adjuster 251 may be inserted into aperture 378 in the locked configuration. After blade extension adjuster 251 is inserted into aperture 378 as shown in FIG. 44A, blade extension adjuster 251 is rotated 90 degrees about axis 336 in direction 342 (i.e., clockwise) to transition into the extension configuration as shown in FIG. 44B. When blade extension adjuster 251 is transitioned into the adjustment configuration as shown in FIG. 44B, second protrusion 340 cams into engagement with aperture 382. At least a portion of second protrusion 340 extends into aperture 382 to provide the interface between blade extension adjuster 251 and blade 352.

Likewise, when blade extension adjuster 251 transitions into the extension configuration as shown in FIG. 44B, first protrusion 338 drives second engagement member 374 to bend and deflect such that tabs 380 are disengaged from notches 368 of body 354. First protrusion 338 may interface with and be adjacent to surface 395. Surface 395 is an inner surface of second engagement member 374. Tabs 380 may extend from surface 395 of second engagement member 374.

Figure 43A:
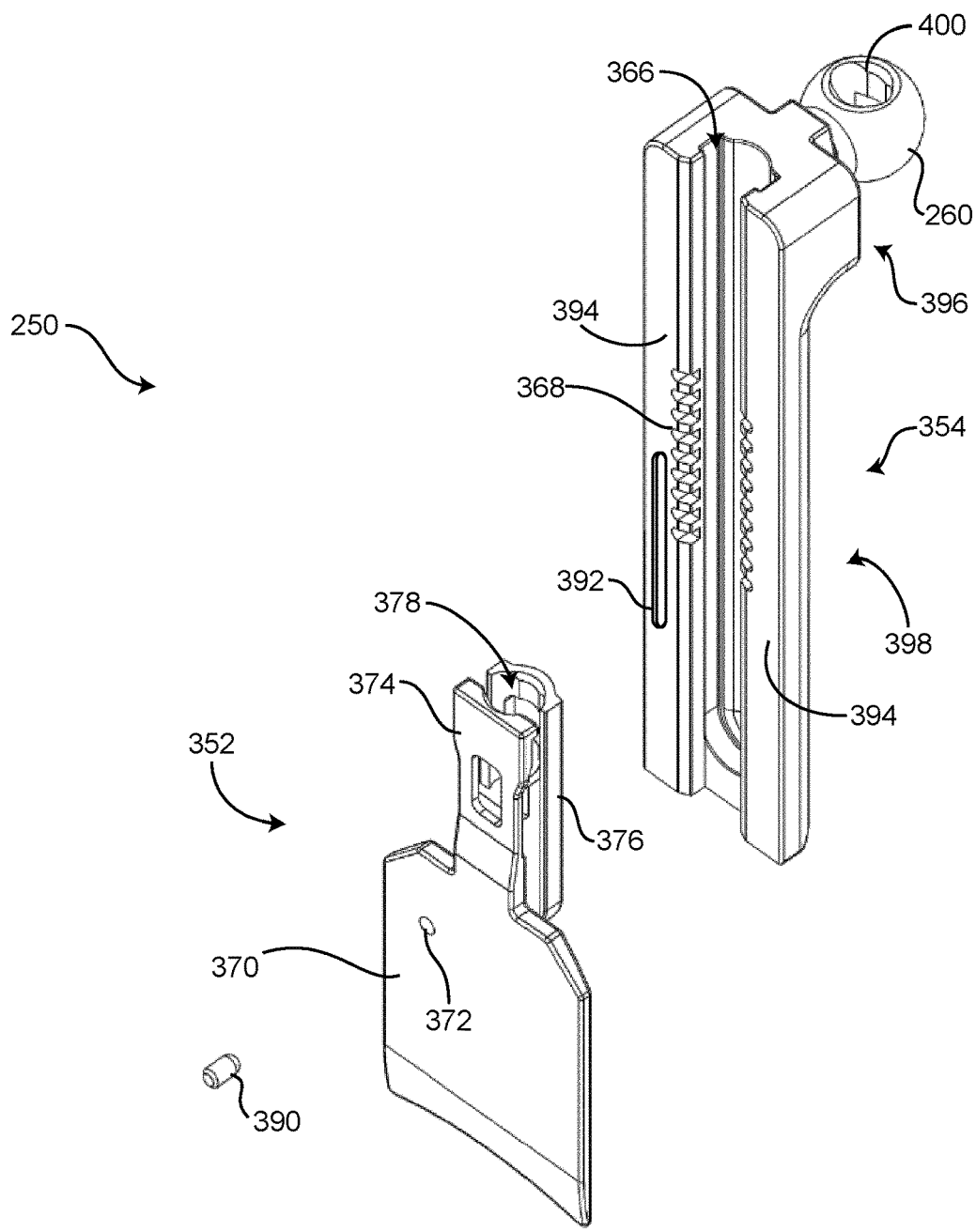
FIG. 43A is an exploded view of the blade of FIG. 40, and a body member of the medial arm of FIGS. 28-33, according to one embodiment.
Figure 43B:
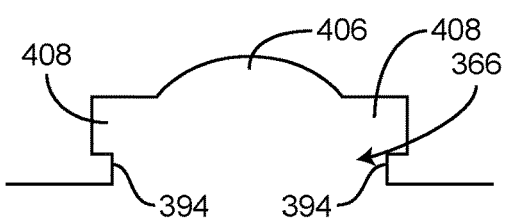
FIG. 43B is a drawing of a cross section of a channel of the body member of FIG. 43A for illustrative purposes, according to one embodiment.

Referring now to FIGS. 43A-B, body 354 and blade 352 are shown in greater detail. Body 354 includes channel 366 configured to receive first engagement member 376 therewithin. First engagement member 376 may translate along at least a portion of the entire length of channel 366. Channel 366 may have a cross-sectional shape as shown in FIG. 43B. The cross-sectional shape of channel 366 may be the same as or correspond to the cross-sectional shape of first engagement member 376. Channel 366 is also configured to interface with second guide member 350 to guide blade extension adjuster 251 into proper connection with blade 352. Channel 366 extends along substantially an entire length of body 354.

Body 354 includes ball 260. Ball 260 may be integrally formed at an upper end 396 of body 354. Ball 260 extends from a rear side 398 of body 354. Ball 260 includes aperture 400 extending at least partially through a center of ball 260. In some embodiments, aperture 400 extends entirely through ball 260. In other embodiments, aperture 400 extends partially through ball 260. Aperture 400 may have a shape corresponding to a cross-section at an end of blade extension adjuster 251. Aperture 400 is configured to receive the end of blade extension adjuster 251 such that blade extension adjuster 251 can be used to adjust an orientation of blade 352. For example, blade extension adjuster 251 may provide a longer moment arm for rotating medial blade assembly 250 about axis 258 and/or axis 254. Advantageously, blade extension adjuster 251 may have a dual-use. For example, blade extension adjuster 251 may be inserted into aperture 378 and used to extend or retract blade 352 and also to rotate medial blade assembly 250 by inserting blade extension adjuster 251 into aperture 400 of ball 260 and rotating medial blade assembly 250.

Body 354 includes track members 394. Track members 394 extend substantially an entire length of body 354. Track members 394 may define at least a portion of channel 366 (e.g., one or more sides of channel 366). Track members 394 are substantially parallel to each other and are offset a distance from each other. Track members 394 include notches 368. Notches 368 extend at least partially into track members 394 on either side of channel 366. Notches 368 are disposed along at least a portion of the length of channel 366 or body 354. Notches 368 are configured to provide predetermined positions of blade 352. In some embodiments, notches 368 include two or more notches. Notches 368 are spaced evenly apart along the length of channel 366 and/or body 354, according to some embodiments. In other embodiments, notches 368 are spaced unevenly along the length of channel 366. For example, notches 368 may each be disposed (e.g., spaced apart) a quarter of an inch from each other. In other embodiments, some of notches 368 are spaced a first distance along the length of channel 366 and/or body 354, while other notches 368 are spaced apart a second distance, where the first distance and the second distance are unequal (e.g., the first distance is greater than the second distance or vice versa). Notches 368 are configured to interface/engage tabs 380 of second engagement member 374. Second engagement member 374 may be selectably disengaged from notches 368 via insertion and rotation of blade extension adjuster 251. Blade 352 can then be translated along channel 366 via moving blade extension adjuster 251 until tabs 380 are adjacent another set of notches 368. Tabs 380 can then be engaged with the other set of notches 368 at a different height (e.g., a different amount of extension or retraction) by rotating blade extension adjuster 251.

Body 354 further includes slot 392. Slot 392 is configured to interface with pin 390. Pin 390 may extend through aperture 372 of blade 352 and translate along slot 392. Slot 392 may prevent blade 352 from rotating. Additionally, pin 390 is restricted to translating along only the entire length of slot 392. This can restrict blade 352 from being translated along channel 366 (e.g., up or down, extended or retracted, etc.) to a position where there are no corresponding notches 368 for tabs 380 to interface with.

Referring now to FIG. 43B, the cross-sectional shape of channel 366 is shown in greater detail. Channel 366 includes an arcuate portion 406, and generally rectangular portions 408. Generally rectangular portions 408 are disposed at opposite sides of arcuate portion 406 and may be at least partially defined by track members 394. The cross-sectional shape of channel 366 as shown in FIG. 43B corresponds to a cross-sectional shape of first engagement member 376, interfacing portion 344, and second guide member 350. For example, second guide member 350 may be configured to interface with at least one of generally rectangular portions 408 such that second guide member 350 can translate along channel 366 within generally rectangular portions 408.

Figure 46:
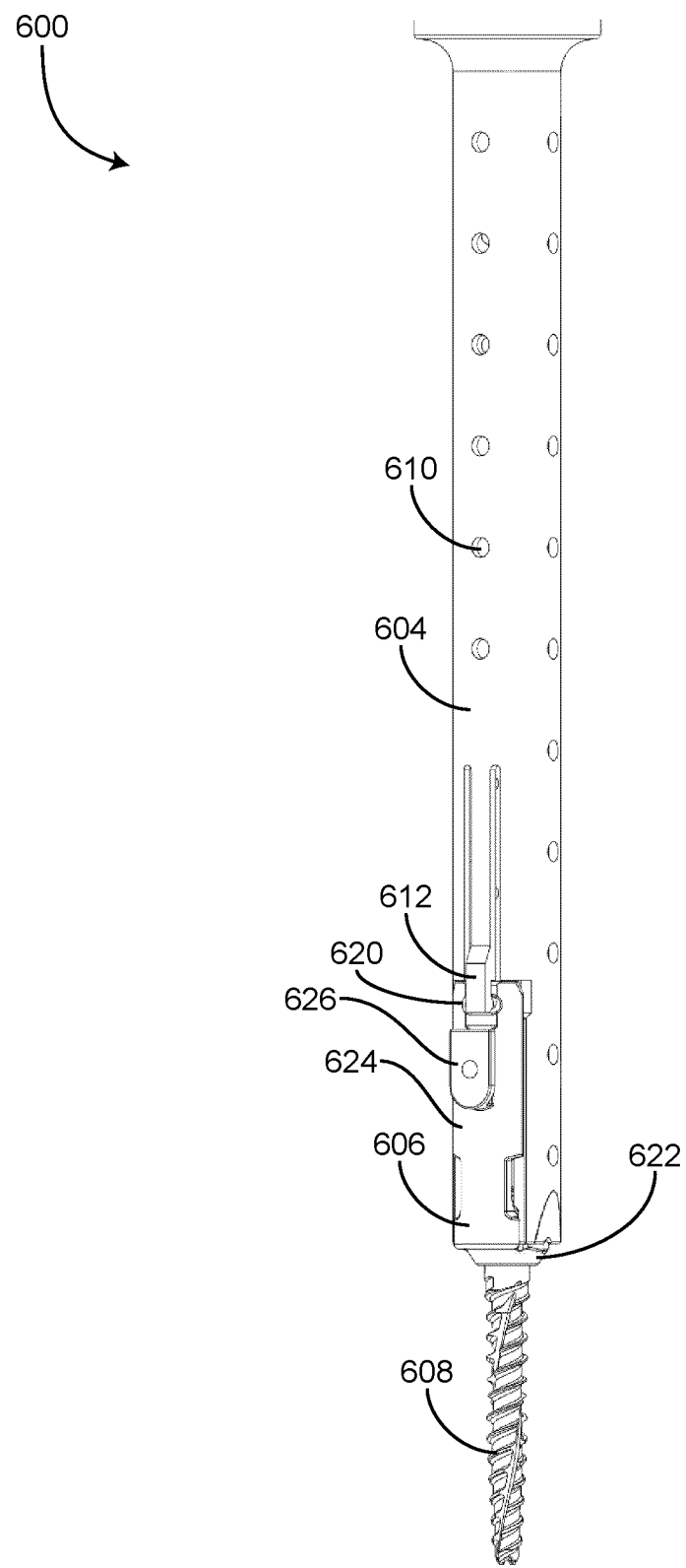
Figure 47:
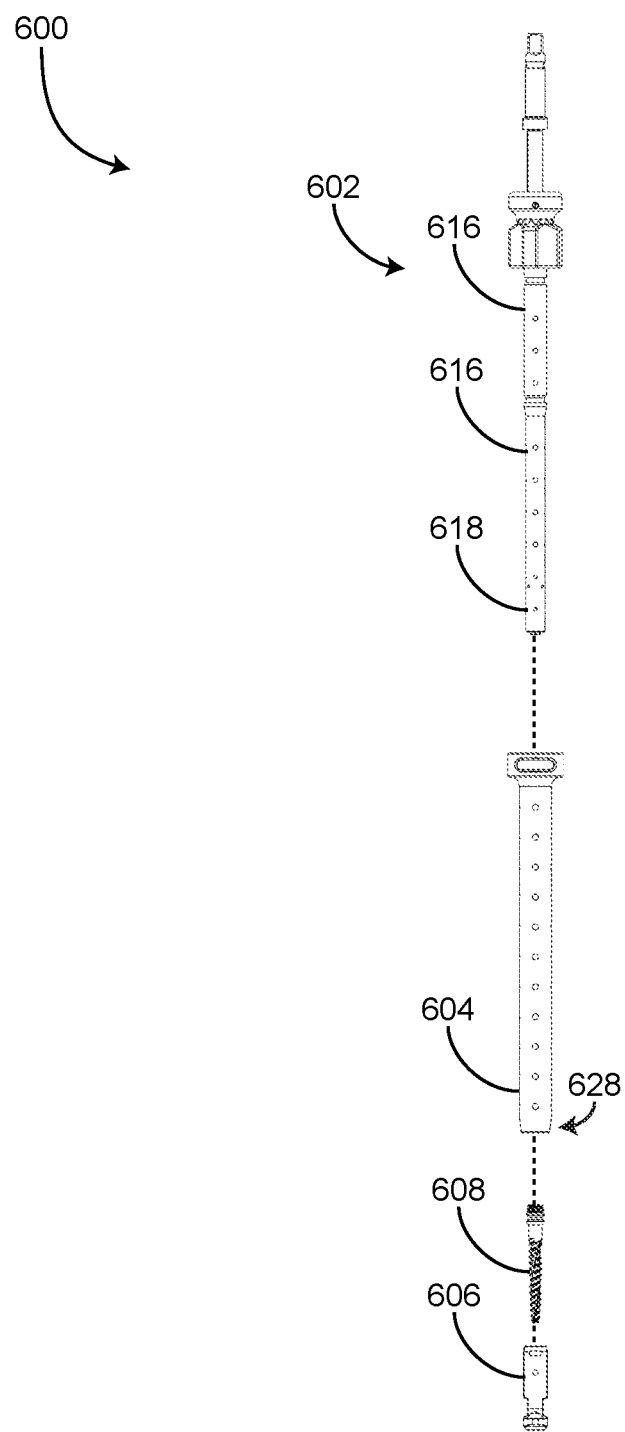
FIG. 47 is an exploded view of the tap and driver assembly of FIGS. 45-46, according to one embodiment.

Referring now to FIGS. 45-47, a tap and driver assembly 600 is shown, according to an exemplary embodiment. Tap and driver assembly 600 may be removably attached to any of first and second side assemblies 214 and 216 or may be removably attached to medial arm 218. For example, tap and driver assembly 600 may be removably attached to blade 352, blade portion 370, or may be configured to interface with and translate along channel 366 similar to blade 352.

Tap and driver assembly 600 includes a driver component 602, a sleeve 604, a hoop 606, and a tap 608. Driver component 602 may be any driver, member, device, etc., configured to drive tap 608 (e.g., to rotate tap 608). Driver component 602 may include a square portion, a hexagonal portion, etc., shown as interfacing member 614. Interfacing member 614 is configured to rotatably couple driver component 602 to a driving device. Interfacing member 614 is configured to be rotated by the driving device and rotate tap 608. Driver component 602 is configured to extend through substantially an entire length of sleeve 604. Driver component 602 may include one or more elongated members 616 configured to extend through sleeve 604 and couple to tap 608. Sleeve 604 may be a generally cylindrical and elongated member having a sidewall with a thickness and an inner volume therewithin. The inner volume of sleeve 604 may receive driver component 602 therewithin. Driver component 602 may include a threaded portion 618 at an end (e.g., at an end of one of elongated members 616). Threaded portion 618 may be a male or female threaded portion. Threaded portion 618 may have clockwise or counterclockwise threads. In an exemplary embodiment, threaded portion 618 include female threads which extend into driver component 602 or one of elongated members 616. The female threads are configured to threadingly interface with male threads of tap 608. In other embodiments, driver component 602 includes an aperture (e.g., a square aperture, a hexagonal aperture) in place of threaded portion 618. The aperture may be configured to interface with an end of tap 608 to transfer rotation of driver component 602 to tap 608.

Hoop 606 is configured to removably connect to sleeve 604, as described in greater detail herein. Hoop 606 is configured to removably couple with any of blade 352, medial arm 218, first and second side assemblies 214 and 216, blade portion 370, etc. Hoop 606 includes receiver 620. Receiver 620 is configured to removably couple hoop 606 with sleeve 604. Receiver 620 may be a slot, an aperture, an opening, etc., configured to receive a hooked end of elongated member 612 of sleeve 604 therewithin. Elongated member 612 of sleeve 604 may function as a spring member. For example, elongated member 612 may deflect, bend, deform, etc., when sleeve 604 is being connected to hoop 606. Elongated member 612 may deflect or bend and snap into receiver 620. For example, sleeve 604 may be inserted downwards into hoop 606 such that elongated member 612 deflects radially outwards from a centerline of sleeve 604. When sleeve 604 has been inserted fully into hoop 606, elongated member 612 returns to its original (e.g., straight) position and the hook at the end of elongated member 612 snaps into receiver 620. Sleeve 604 and hoop 606 may be fixedly coupled via the interface between receiver 620 and elongated member 612. In order to remove sleeve 604 from hoop 606, elongated member 612 must be deflected, deformed, bent, etc., until the hook at the end of elongated member 612 does not engage/interface with receiver 620. When the hook at the end of elongated member 612 is disengaged from receiver 620, sleeve 604 can be removed from hoop 606.

Hoop 606 includes receiving portion 622 and elongated portion 624. Receiving portion 622 and elongated portion 624 may be integrally formed. Receiving portion 622 is configured to receive (e.g., via an aperture, a hole, etc.), sleeve 604. For example, receiving portion 622 may include an aperture configured to receive a stepped portion or a tapered end (e.g., tapered end 628 as shown in FIG. 47) of sleeve 604. The stepped portion or tapered end of sleeve 604 may be at a bottom end of sleeve 604. Elongated portion 624 of hoop 606 extends longitudinally from receiving portion 622. Elongated portion 624 may extend longitudinally upwards along at least portion of sleeve 604 and/or driver component 602. Elongated portion include receiver 620 configured to interface with elongated member 612 of sleeve 604. Elongated portion 624 also includes a hook, connector, interfacing member, etc., shown as hook 626. Hook 626 is configured to removably couple hoop 606 and thereby tap and driver assembly 600 to any of medial arm 218, first and second side assemblies 214 and 216, first or second side blade assemblies 540 and 556, first and second side blade assemblies 40 and 56, center assembly 18, first and second side assemblies 214 and 216, center blade assembly 74, body 354, blade 352, etc. For example, hook 626 may interface with a corresponding slot, recess, groove, aperture, shoulder, step, surface, hole, etc., of any of the hereinabove mentioned elements to removably couple tap and driver assembly 600 with any of the hereinabove mentioned elements.

Tap 608 may have self-tapping threads. Tap 608 may be driven to rotate by rotation of driver component 602. Tap 608 is rotatably coupled with driver component 602 (e.g., via a threaded interface) such that rotation of driver component 602 is transferred to tap 608.

Advantageously, the retractor as shown in FIGS. 26-47 provides a medial arm assembly which may be selectably extended or retracted and locked in place. Additionally, a blade assembly attached to the medial arm can be rotated about several axes (e.g., axis 254, axis 258, etc.) to facilitate more controllability of the medial arm. Advantageously, this can allow a user to access a surgical area with the medial arm. A blade connected to the medial arm can be extended or retracted, and can be locked in place at a desired position. A blade extension adjuster can be inserted into the blade and used to transition the blade between a locked configuration (where the blade cannot extend or retract and is locked in a current position) or an adjustable/extendable configuration where the blade can be It should be understood that the spinal retractors shown herein may share any or all of the features described elsewhere herein or with reference to U.S. application Ser. No. 15/448,010, filed Mar. 2, 2017, the entirety of which is incorporated by reference herein, including blade extenders/supplemental blades, blade locking features, lighting features extending within channels in the blades, and the like. All such combinations of features are to be understood to be within the scope of the present disclosure.

In one embodiment, in operating a spinal retractor such as one described herein, the retractor is placed into a desired position. A first side assembly, a second side assembly, and a center assembly of the retractor are translated along threaded shafts relative to a frame of the retractor. The side and center assemblies may be translated via manipulation of ball joint assemblies that couple adjustment knobs to the respective threaded shafts.

The spinal retractor shown and described herein may provide various benefits over more traditional designs. The support handle provides a modular, ergonomic handle for improved manipulation of the base or frame to ease alignment of the device, and the adjustment handles provide modular ergonomic handles for translation of the side and center assemblies without the need for additional instrumentation. Further, the adjustment handles stabilize the positions of the adjustment knobs for ease of use. The gear ratios of the threaded shafts provide faster translation of components (e.g., twice as fast as certain conventional device) such that each of the side and center assemblies can be completely expanded with 1.5 revolutions of the threaded shafts/adjustment knobs.

Additionally, the frame weight is less compared to more traditional devices (e.g., by 15 percent or more), and the frame geometry is optimized to enable table arm attachment to the center arm assembly while eliminating interference with the base or frame (e.g., in situations when the table arm extends generally parallel to the length of the frame or base). In some embodiments, blade extenders include self-retaining springs to ensure the blade extenders remain captured within the blades, and the blade locking mechanisms provide a spring-activated locking feature requiring only a one quarter turn to lock/unlock the blades. Further, light sources may extend down channels in the blades to provide optimized lighting (e.g., 15 percent or more light output relative to more traditional designs).

While the invention has been illustrated and described in detail in the drawings and foregoing description, the same is to be considered as illustrative and not restrictive in character, it being understood that only a preferred embodiment has been shown and described and that all changes and modifications that come within the spirit of the invention are desired to be protected.

What is claimed is:

1. A retractor assembly, comprising:
    a base;
    a first side assembly coupled to a first side of the base and configured to translate relative to the base along a first direction;
    a second side assembly coupled to a second side of the base and configured to translate relative to the base along the first direction; and
    a medial arm assembly coupled to the base and configured to extend in an extension direction and retract in a retraction direction relative to the base, wherein the extension direction is opposite to the retraction direction and the extension direction and the retraction direction are perpendicular to the first direction, the medial arm assembly comprising:
    a body coupled to the base;
    a receiving portion including a socket with a locking member, wherein the receiving portion is configured to be movable relative to the body; and
    a blade assembly comprising a medial blade including a ball, wherein the receiving portion and the blade assembly are configured to rotatably interface via the ball and the socket, and wherein the locking member includes a set screw configured to selectively engage a pin in the receiving portion and drive the pin into engagement with the ball to restrict rotation of the medial blade relative to the receiving portion.

2. The retractor assembly of claim 1, wherein the medial arm assembly comprises a frame configured to translate relative to the body, wherein the blade assembly is coupled to the frame.

3. The retractor assembly of claim 2, wherein the blade assembly is configured to rotatably interface with the frame via a hinge and pivot about a first axis extending through a center of the hinge.

4. The retractor assembly of claim 1, wherein the medial blade is configured to rotatably interface with the receiving portion about a rotational axis extending outwards from a center of the receiving portion.

5. The retractor assembly of claim 1, wherein the set screw is configured to:
    threadingly interface with an aperture of the receiving portion;
    engage the pin; and
    drive the pin into engagement with a corresponding surface of the ball;
    wherein the pin comprises a surface at one end configured to interface with an end of the set screw and a surface at a second end configured to interface with the corresponding surface of the ball.

6. The retractor assembly of claim 2, wherein the body comprises a locking mechanism configured to selectably transition between a locked mode and an unlocked mode, wherein the locked mode restricts translation of the frame relative to the body and the unlocked mode allows translation of the frame relative to the body.

7. The retractor assembly of claim 2, wherein the body comprises a releasable ratcheting mechanism configured to restrict translation of the frame in at least one of the extension direction and the retraction direction.

8. A retractor assembly, comprising:
    a base;
    a first side assembly coupled to a first side of the base and configured to move relative to the base along a first direction;
    a second side assembly coupled to a second side of the base and configured to move relative to the base along the first direction; and
    a medial arm assembly coupled to the base between the first side assembly and the second side assembly, the medial arm assembly comprising:
    a medial arm body coupled to the base;
    a frame configured to translate relative to the medial arm body through an aperture of the medial arm body along a second direction perpendicular to the first direction;
    a receiving member hingedly coupled to the frame such that the receiving member is rotatable relative to the frame about a first axis; and
    a medial blade assembly including a medial blade and a body rotatably coupled to the receiving member such that the medial blade assembly is rotatable relative to the receiving member about a second axis perpendicular to the first axis and perpendicular to a medial blade axis, the medial blade axis extending along a length of the medial blade, the medial blade comprising a first member configured to slidably interface with a channel of the body, and a second member configured to selectably deflect relative to the first member to enable repositioning of the medial blade along the channel;
    wherein rotation of the receiving member relative to the frame causes rotation of the medial blade relative to the frame about the first axis.

9. The retractor assembly of claim 8,
    wherein the second member comprises one or more tabs configured to interface with one or more of a plurality of notches of the body and at least a portion of the first member is configured to slidably interface within the channel of the body.

10. The retractor assembly of claim 9, wherein the plurality of notches are disposed along an exterior surface of the body and define a plurality of predefined positions of the medial blade with respect to the body.

11. The retractor assembly of claim 10, wherein the second member is configured to selectably deflect between an engaged state to lock the medial blade at a current position relative to the body, and a disengaged state to allow translation of the medial blade relative to the body, wherein in the engaged state at least one of the one or more tabs is engaged with at least one of the plurality of notches, and in the disengaged state the one or more tabs are disengaged from the plurality of notches.

12. The retractor assembly of claim 11, wherein the one or more tabs are disposed at an end of the second member and wherein the first member and the second member are disposed a distance apart to define a space therebetween for receiving an adjustment member to transition the second member between the engaged state and the disengaged state.

13. The retractor assembly of claim 12, wherein the medial blade assembly is configured to receive the adjustment member and the second member is configured to deflect to transition between the engaged state and the disengaged state in response to a rotation of the adjustment member.

14. The retractor assembly of claim 8, wherein the medial blade is configured to releasably interface with a modular tap assembly comprising a driver, a hoop, a sleeve, and a tap.

15. A retractor assembly, comprising:
   a base;
   a first side assembly coupled to a first side of the base and configured to translate relative to the base along a first direction;
   a second side assembly coupled to a second side of the base and configured to translate relative to the base along the first direction; and
   a medial arm assembly coupled to the base and configured to extend relative to the base in an extension direction and retract relative to the base in a retraction direction, wherein the extension direction is opposite to the retraction direction and the extension direction and the retraction direction are perpendicular to the first direction, the medial arm assembly comprising:
      a body coupled to the base;
      a frame coupled to the body and movable in the retraction direction and the extension direction relative to the body and along a longitudinal axis of the frame;
      a receiver portion coupled to the frame, wherein the receiver portion is configured pivot relative to the frame about a first axis perpendicular to the longitudinal axis; and
      a medial blade assembly coupled to the receiver portion via a rotational interface configured to facilitate rotation of the medial blade assembly relative to the receiver portion about a second axis perpendicular to the first axis and perpendicular to a longitudinal axis of the medial blade assembly, wherein the rotational interface is positioned outward from the first axis relative to the base;
   wherein pivoting of the receiver portion relative to the frame causes rotation of the medial blade assembly relative to the frame about the first axis.

16. The retractor assembly of claim 15, wherein the medial blade assembly rotates about the second axis at an upper end portion of the medial blade assembly.

17. The retractor assembly of claim 15, wherein the medial blade assembly is movable through an angular range of motion about the second axis and releasably lockable at any desired position along the angular range of motion.

18. The retractor assembly of claim 15, wherein the rotational interface includes a ball and socket joint.

19. The retractor assembly of claim 15, wherein the medial blade assembly is configured to rotate about the first axis via a hinge element comprising a hinge pin extending along the first axis.

20. The retractor assembly of claim 15, wherein the medial blade assembly further includes a rotational control lever configured to hingedly rotate the medial blade assembly about the first axis in response to actuation of the rotational control lever.

* * * * *